(12) United States Patent
Grunwald

(10) Patent No.: US 9,446,121 B2
(45) Date of Patent: *Sep. 20, 2016

(54) CLONING OF HONEY BEE ALLERGEN

(75) Inventor: Thomas Grunwald, Hamburg (DE)

(73) Assignee: PLS-DESIGN GMBH, Hamburg (DE)

(*) Notice: Subject to any disclaimer, the term of this patent is extended or adjusted under 35 U.S.C. 154(b) by 653 days.

This patent is subject to a terminal disclaimer.

(21) Appl. No.: 12/404,168

(22) Filed: Mar. 13, 2009

(65) Prior Publication Data

US 2010/0015122 A1 Jan. 21, 2010

Related U.S. Application Data

(63) Continuation-in-part of application No. 11/301,329, filed on Dec. 13, 2005, now Pat. No. 7,846,690.

(60) Provisional application No. 60/635,479, filed on Dec. 14, 2004.

(51) Int. Cl.

| | |
|---|---|
| *A61K 38/00* | (2006.01) |
| *A61K 38/04* | (2006.01) |
| *A61K 39/00* | (2006.01) |
| *A61K 39/35* | (2006.01) |
| *A61K 39/36* | (2006.01) |
| *C07K 1/00* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 14/435* | (2006.01) |

(52) U.S. Cl.
CPC .......... *A61K 39/35* (2013.01); *C07K 14/43572* (2013.01)

(58) Field of Classification Search
None
See application file for complete search history.

(56) References Cited

U.S. PATENT DOCUMENTS

| | | | | |
|---|---|---|---|---|
| 5,304,631 A * | 4/1994 | Stewart et al. | ................ | 530/323 |
| 6,812,339 B1 | 11/2004 | Venter et al. | | |
| 7,365,185 B2 | 4/2008 | Boukharov et al. | | |
| 2004/0023291 A1 | 2/2004 | Spertini | | |
| 2004/0034888 A1* | 2/2004 | Liu et al. | ....................... | 800/289 |

FOREIGN PATENT DOCUMENTS

| | | | | |
|---|---|---|---|---|
| GB | 2341389 A | | 3/2000 | |
| WO | WO 00/55174 | * | 9/2000 | ............. C07K 14/47 |
| WO | WO 02/77183 | * | 3/2002 | ............ C07K 14/195 |

OTHER PUBLICATIONS

Georgieva et al. '3-D Model of the bee venom acid phosphatase: Insights into allergenicity.' Biochemical and Biophysical Research Communications 378:711-715, 2009.*

Accession No. AF205594—Nov. 16, 1999.*

Grunwald et al. 'Molecular cloning and expression in insect cells of honeybee venom allergen acid phosphatase (Api m 3).' J. Allergy Clin. Immunol. 117:848-854, 2006.*

Metzler et all "Solution structure of human CTLA-4 and delineation of a CD80/CD86 binding site conserved in CD28." Nature Structural Biol. 4:527-531,1997.

Bork et al. "Powers and Pitfalls in Sequence Analysis: The 70% Hurdle." Genome Research. 10:398-400, 2000.

Doerks et al. 'Protein annotation: detective work for function prediction.' Trends in Genetics. 14:248-250, 1998.

Smith et al. The challenges of genome sequence annotation or "The devil is in the details". Nat. Biotech. 15:1222-1223, 1997.

Brenner S. 'Errors in Genome Annotation.' Trends in Genetics 15:132-133, 1999.

Bowie et al. "Deciphering the Message in Protein Sequences: Tolerance to Amino Acid Substitutions". Science 247: 1306-1310, 1990.

Lerner et al. 'Tapping the immunological repertoire to produce antibodies of predetermined specificity.' Nature. 299:593-596, 1982.

Arbesman et al., "Allergenic potency of bee antigens measured by RAST inhibition", Clinical Allergy, vol. 6, pp. 587-594 (1976).

Barboni et al., "The Purification of Acid Phosphatase from Honey Bee Venom (Apis Mellifica)", Toxicon, vol. 25, No. 10, pp. 1097-1103 (1987).

Castro et al., "Biochemical properties and study of antigenic cross-reactivity between Africanized honey bee and wasp venom", J. Invest AllergoL Clin. Immunol., vol. 4(1), pp. 37-41 (1994).

Dotimas and Hider, "Honeybee Venom", Bee World, vol. 68(2), pp. 51-70 (1987).

Eich-Wanger and Muller, "Bee sting allergy in beekeepers", Clinical and Experimental Allergy, vol. 28, pp. 1292-1298 (1998).

Elbein, "The role of N-linked oligosaccharides in glycoprotein function", TIBTECH, vol. 9, pp. 346-352 (1991).

Gmachl and Kreil, "Bee venom hyaluronidase is homologous to a membrane protein of mammalian sperm", Proc. Natl. Acad. Sci. USA, vol. 90, pp. 3569-3573 (1993).

Grunwald et al., Database EMBL (Online), Accession No. DQ058012 (Jun. 5, 2005) (XP-002370247).

Grunwald et a/., Database UniProt (Online), Accession No. Q4TUB9 (Jul. 19, 2005) (XP-002370414).

Habermann, "Bienen- und Wespenstiche aus medizinischer Sicht", Allgemeine Deutsche Imkerzeitung (ADIZ), vol. 11, p. 301-304 (1974).

(Continued)

*Primary Examiner* — Nora Rooney
(74) *Attorney, Agent, or Firm* — Ann Wieczorek; Mayer & Williams PC

(57) ABSTRACT

The present invention relates to a recombinant polypeptide capable of binding to IgE from subjects allergic to venom of an insect from the order Hymenoptera having a homology of more than 70% to the amino acid sequence of SEQ ID NO: 2, which is the honey bee allergen Api m3 (acid phosphatase). The invention further relates to nucleic acid encoding the polypeptide, expression vectors, host cells and methods of preparing the polypeptide, as well as diagnostic and pharmaceutical uses thereof.

14 Claims, 15 Drawing Sheets

(56) References Cited

OTHER PUBLICATIONS

Helbling et al., "Incidence of anaphylaxis with circulatory symptoms: a study over a 3-year period comprising 940000 inhabitants of the Swiss Canton Bern", Clin. Exp. Allergy, vol. 34, pp. 285-290 (2004).
Hoffman et al., Database UniProt (Online), Accession No. Q5BLY5 (Apr. 12, 2005) (XP-002370416).
Hoffman et al., Database EMBL (Online), Accession No. AY939855 (Mar. 19, 2005) (XP 002370415).
Hoffman et al., "Allergens in Hymenoptera venom XXI. Cross-reactivity and multiple reactivity between fire ant venom and bee and wasp venoms", J. Allergy Clin. Immunol., vol. 82, No. 5, Part 1, pp. 828-833 (1988).
Hoffman, "Hymenoptera Venom Proteins" in Natural Toxins 2, Eds. Singh and Tu, Plenum Press, New York and London (1996).
Hoffman and Shipman, "Allergens in bee venom", J. Allergy Clin. Immunol., vol. 58, No. 5, pp. 551-562 (1976).
Hoffman et a/., "Allergens in bee venom II. Two new high molecular weight allergenic specificities", J. Allergy Clin. Immunol., vol. 59, No. 2, pp. 147-153 (1977).
Hunt et a/., "A Controlled Trial ofImmunotherapy in Insect Hypersensitivity", The New England Journal of Medicine, vol. 299, No. 4, pp. 157-161 (1978).
International Search Report from International Application No. PCT/EP2005/013397, issued Apr. 6, 2006.
Jacobsen and Hoffman, "Honey-bee venom acid phosphatase is a member of the prostatic acid phosphatase family", J. Allergy Clin. Immunol., vol. 95, pp. 372 (1995).
Kettner et al., "Api m 6: A new bee venom allergen", J. Allergy Clin. Immunol., vol. 107, No. 5, pp. 914-920 (2001).
Kettner et al., "IgE and T-cell responses to high-molecular weight allergens from bee venom", Clinical and Experimental Allergy, vol. 29, pp. 394-401 (1999).
King, "Insect Venom Allergens", Allergy, vol. 28, pp. 84-100 (1990).
King and Spangfort, "Structure and Biology of Stinging Insect Venom Allergens", Int. Arch. Allergy Immunol., vol. 123, pp. 99-106 (2000).
Kuchler et al., "Analysis of the cDNA for phospholipase A2 from honeybee venom glands. The deduced amino acid sequence reveals homology to the corresponding vertebrate enzymes", Eur. J. Biochem, vol. 184, pp. 249-254 (1989).
Kulike, "Zur Struktur und Funktion des Hymenopterenstachels", Amts- und Mitteilungsblatt der Bundesanstalt fur Materialprufung, vol. 16, pp. 519-550 (1986).
Muller, "New Developments in the Diagnosis and Treatment of Hymenoptera Venom Allergy", Int. Arch. Allergy Immunol., vol. 124, pp. 447-453 (2001).
Muller, "Recombinant Hymenoptera venom allergens", Allergy, vol. 57, pp. 570-576 (2002).
Schiavino et al., "Specific ultrarush desensitization in Hymenoptera venom-allergic patients", Anals of Allergy, Asthma, & Immunology, vol. 92, pp. 409-413 (2004).
Sobotka et af., "Honeybee venom: Phospholipase A as the major allergen", J. Clin. Allergy Clin. Immunol., vol. 53, p. 103, Abstract No. 96, (1974).
Sobotka et al., "Allergy to insect stings II. Phospholipase A: The major allergen in honeybee venom", J. Allergy Clin. Immunol., vol. 57, No. 1, pp. 29-40 (1976).
Soldatova et al., Database EMBL (Online), Accession No. AF205594 (Nov. 8, 2005) (XP-002370417).
Soldatova et al., Database UniProt (Online), Accession No. Q336K2, (Dec. 6, 2005) (XP-002370418).
Soldatova, "Biological Activity of Recombinant Bee Venom Allergens Expressed in Baculovirus-infected Cells", Arbeiten Aus Dem Paul-Ehrlich-Institut, 9th International Paul-Ehrlich-Seminar, No. 9, pp. 189-193 (1999).
Soldatova et al., "Superior biologic activity of the recombinant bee venom allergen hyaluronidase expressed in baculovirus-infected insect cells as compared with *Escherichia coli*", J. Allergy Clin. Irnmunol., vol. 101, No. 5, pp. 691-698 (1998).
Soldatova et al., "Molecular Cloning of a New Honeybee Venom Allergen, Acid Phosphatase", J. Allergy Clin. Irnmunol., Abstracts, p. S378, Abstract No. 1105 (2000).
Sudowe et al., "Efficacy of recombinant adenovirus as vector for allergen gene therapy in a mouse model of type I allergy", Gene Therapy, vol. 9, pp. 147-156 (2002).
Vlasak et al., "Nucleotide sequence of cloned cDNA coding for honeybee prepromelittin", Eur. J. Biochem., vol. 135, pp. 123-126 (1983).
Wypych et al., "Analysis of Differing Patterns of Cross-Reactivity of Honeybee and Yellow Jacket Venom-Specific IgE: Use of Purified Venom Fractions", Int. Arch. Allergy. AQQI. Irnmunol., vol. 89, pp. 60-66 (1989).
Friedrich Altmann, The Role of Protein Glycosylation in Allergy Divison of Biochemistry, Department of Chemistry, University of Natural Resources and Applied Life Sciences, Vienna , Austria, Int Arch Allergy Immunol 2007;142:99-115.
Terry M. Fieser, Influence of protein flexibility and peptide conformation on reactivity of monoclonal anti-peptide antibodies with a protein a-helix (protein antigenicity/peptide antigens/atomic mobility/myohemerythrin) Proc. Natl. Acad. Sci. USA vol. 84, pp. 8568-8572, Dec. 1987.
Christoph Geisler and Don Jarvis, Insect Cell Glycosylation Patterns in the Context of Biopharmaceuticals, Copyright ! 2009 WILEY-VCH Verlag GmbH & Co. KGaA, Weinheim ISBN: 978-3-527-32074-5.
Thomas Grunwald, PhD, , Molecular cloning and expression in insect cells of honeybee venom allergen acid phosphatase (Api m 3) J Allergy Clin Immunol vol. 117, No. 4, p. 848-854, 2006.
Robert G. Hamilton, PhD, D (ABMLI), Proficiency Survey-Based Evaluation of Clinical Total and Allergen-Specific IgE Assay Performance, Arch Pathol Lab Med—vol. 134, Jul. 2010, p. 975-982.
Tsu-An Hsu, Differential N-Glycan Patterns of Secreted and Intracellular IgG Produced in Trichoplusia ni Cells* The Journal of Biological Chemistry vol. 272, No. 14, Issue of Apr. 4, pp. 9062-9070, 1997.
Wolfgang Kabsch and Christian Sander, On the use of sequence homologies to predict protein structure: Identical pentapeptides can have completely different conformations (cooperativity/protein folding/amino acid sequence homology), Proc. Natl. Acad. Sci. USA vol. 81, pp. 1075-1078, Feb. 1984.
R. M. O'Brien, An immunogenetic analysis of the T-cell recognition of the major house dust mite allergen Der p 2: identification of high- and low-responder HLA-DQ alleles and localization of T-cell epitopes Immunology 1995 86 176-182.
Erika Staudacher, Distinct N-glycan fucosylation potentials of three lepidopteran cell lines, Eur. J. Biochem. 207,987-993 (1992) 0 FEBS 1992.
Noriko Takahashi, N-glycan structures of murine hippocamps serine protease, neuropsin, produced in Trichoplusia ni cells, Glycoconjugate Journal 16, 405-414 (1999).
Ian A. Wilson, et al., Identical short peptide sequences in unrelated proteins can have different conformations: A testing ground for theories of immune recognition (protein structure/sequence comparisons/antipeptide antibodies), Proc. Natl. Acad. Sci. USA vol. 82, pp. 5255-5259, Aug. 1985.
Thomas M. Li, Development and Validation of a Third Generation Allergen-Specific IgE Assay on the Continuous Random Access IMMULITE® 2000 AnalyzerAnnals of Clinical & Laboratory Science, vol. 34, No. 1, 2004, pp. 67-74.
Arbesman, et al. "Allergenic potency of bee antigens measured by RAST inhibition" Clinical Allergy (1976) vol. 6, pp. 587-594.
Barbee et al. "Immediate Skin-Test Reactivity in a General Population Sample" Annals of Internal Medicine Feb. 1976, vol. 84, No. 2, 5 pages.
Barboni et al. "The purification of Acid Phosphatase from Honey Bee Venom" Toxicon, vol. 25, No. 10, pp. 1097-1103, 1987.
L. Bauer, "Modulation of the allergic immune response in BALB/c mice by subcutaneous injection of high does of the dominant T cell epitope from the major birch pollen allergen Bet v 1", Clin Exp Immunol 1997; 107:536-541.

(56) References Cited

OTHER PUBLICATIONS

Benjamin, "The Antigenic Structure of Proteins:a Reappraisal" Ann, Rev. Immunol. 1984.2:67-101.
Boel, Functional human monoclonal antibodies of all isotypes constructed from phage display library-derived singleahain Fv antibody fragments, Journal of Immunological Methods 239 (2000) 153-166.
Briner, "Peripheral T-cell tolerance induced in naive and primed mice by subcutaneous injection of peptides from the major cat allergen Fel d I" Proc. Natl. Acad. Sci. USA, vol. 90, pp. 7608-7612, Aug. 1993.
Carballido, "T Cell Epitope Specificity in Human Allergic and Nonallergic Subjects to Bee Venom Phospholipase A21" The Journal of Immunology, vol. 150, 3582-3591, No. 8, Apr. 15, 1993.
Castro, Biochemical properties and study of antigenic cross-reactivity between Africanized honey bee and wasp venom J Invest Allergol Clin Immunol, Jan.-Feb. 1994; vol. 4(1): 37-41.
Dhillon M. et al. Mapping human T cell epitopes on phospholipase A2: The major bee-venom allergen. J. Allergy Clin. Immunol. 90, 42-51 (1992).
Dotimas et al., "Honeybee Venom", Department of Chemistry, University of Essex, 1987, pp. 51-70.
Edwards M.R. et al. Analysis of IgE Antibodies from a Patient with Atopic Dermatitis: Biased V Gene Usage and Evidence for Polyreactive IgE Heavy Chain Complementary-Determining Region 3. J Immunol 168, 6305-6313 (2002).
Eich-Wanger et al. "Bee sting allergy in beekeepers" 1998 Blackwell Science Ltd. pages 1292-1298.
Elbein, "The role of N-linked oligosaccharides in glycoprotein function" Tritech Oct. 1991 (vol. 9) pp. 346-352.
Fratemali F. and Cavallo L. Parameter optimized surfaces (POPS): analysis of interactions and conformational ahanges in the ribosome. Nucleic Acids Res. 30, 2950-2960 (2002).
Ganglberger E. et al. Allergen mimotopes for 3-dimensional epitope search and induction of antibodies inhibiting iuman IgE FASEB J. 14, 2177-2184 (2000).
Gmachi "Bee venom hyaluronidase is homologous to a membrane protein of mammalian sperm" Proc. Natl. Acad. Sci. USA vol. 90, pp. 3569-3573, Apr. 1993.
Hamilton RG. Diagnosis of Hymenoptera venom sensitivity, Curr Opin Allergy Clin Immunol 2, 347-351 (2002).
Helbling "Incidence of anaphylaxis with circulatory symptoms: a study over a 3-year period comprising 940 000 inhabitants of the Swiss Canton Bern" Clin Exp Allergy 2004; 34:285-290.
Hemmer W et al. Identification by immunoblot of venom glycoproteins displaying immunoglobulin E-binding N-glycans 3s cross-reactive allergens in honeybee and yellow jacket venom, Clin Exp Allergy 34, 460-469 (2004).
Hoffman "Separation and identification of the major allergens" J. Allergy Clin. Immunol. Nov. 1976, vol. 58, No. 3, pp. 551-562.
Hoffman "Allergens in bee venom" J. Allergy Clin. Immunol. Feb. 1977, vol. 59, No. 2, pp. 147-153.
Hoffman, "Cross-Reactivity and multiple reacivity between fire ant venom and bee and wasp venoms" J. Allergy Clin, Immunol. Nov. 1988, vol. 82, No. 5, part 1, pp. 828-834.
Hoffman, Hymenoptera Venom Proteins, exert from National Toxins 2, 11 pages, 1996.
Hoyne GF et al. Inhibition of T Cell and Antibody Response to House Dust Mite Allergen by Inhalation of the Dominant T Cell Epitope in Naive and Sensitized Mice. J. Exp. Med. 178, 1783-1788 (1993).
Huby RDJ et al. Why are Some Proteins Allergens ? Tox Sci 55 235-246 (2000).
Hunt "A Controlled Trial of Immunotherapy in insect Hypersensitivity", The New England Journal of Medicine, vol. 299, No. 4, Jul. 27, 1978 pp. 157-161.
Jacobson, Honey-bee Venom Acid Phosphatease is a member of the prostatic acid phosphatase family, J. Allergy Clin Immunol, Jan. 1995, Abstract, one page.

Jenkins N et al. Getting the glycosylation right: Implications for the biotechnology industry, Nature Biotech 14, 975-981 (1996).
Jutel M. et al. Mechanism of allergen specific immunotherapy — T-cell tolerance and more. Allergy 61, 796-807 (2006).
Karamloo F. et al. Prevention of allergy by a recombinant multi-allergen vaccine with reduced IgE binding and preserved T cell epitopes. Eur. J. Immunol. 35, 3268-3276 (2005).
Kemeny DM, MacKenzie-Mills M, Harries MG, Youlten LJ, Lessof MH. Antibodies to purified bee venom proteins and peptides. II. A detailed study of changes in IgE and IgG antibodies to individual bee venom antigens. J Allergy Clin Immunol 72, 376-85(1983).
Kettner "Api m 6: A new bee Venom allergen" J Allergy Clin Immunol vol. 107, No. 5, 2001, pp. 914-920.
King, "Structure and Biology of Stinging Insect Venom Allergens" Int Arch Allergy Immunol 2000;123:99-106.
King, "Insect Venom Allergens", Monogr Allergy, 1990, vol. 28, pp. 84-100.
Kuchler, "Analysis of the cDNA for phospholipase A2 from honeybee venom glands the deduced amino acid sequence reveals homology to the corresponding vertebrate enzymes" Eur J Riocheni. 184, 249-254 (1989).
Lebecque "Immunologic characterization of monoclonal antibodies that modulate human IgE binding to the major birch pollen allergen Bet v 1" J Allergy Clin Immunol vol. 99, No. 3, pp. 374-3841977.
MacKenzie T and Dosch H-M. Clonal and Molecular Characterization of the Human IgE-Committed B Cell Subset. J. Exp. Med. 169, 407-430 (1989).
Mirza O et al. Dominant Epitopes and Allergic Cross-Reactivity: Complex Formation Between a Fab Fragment of a Monoclonal Murine IgG Antibody and the Major Allergen from Birch Pollen Bet v 1. J. Immunol. 165, 331-338 (2000).
Muller U et al. Successful immunotherapy with T-cell epitope peptides of bee venom phospholipase A2 induces specific T-cell anergy in patients allergic to bee venom. J. Allergy Clin. Immunol. 101, 747-754 (1998).
Muller "New Developments in the Diagnosis and Treatment of Hymenoptera Venom Allergy", Int Arch Allergy Immunol 2001; 124:447-453, 2001.
Muller "Reombinant Hymenoptera venom allergens" Allergy 2002, 57: 570-576.
Niederberger V et al. Vaccination with genetically engineered allergens prevents progression of allergic disease. Proc. Natl. Acad. Sci. USA 101, 14677-14682 (2004).
Petersen A, Mundt C. Investigations on the carbohydrate moieties of glycoprotein allergens, J Chromat B 756, 141-150 (2001).
Poulsen LK. In-vitro diagnosis: serum-based methods used for risk assessment in allergenic food, Curr. Opin. Allery Clin. Immunol. 1, 249-254 (2001).
Powers D.B. et al. Expression of single-chain Fv-Fc fusions in Pichia pastoris J. Immunol Meth. 251, 123-135 (2001).
Schiavino, "Specific ultrarush desensitization in Hymenoptera venom-allergic patients", vol. 92, Apr. 2004, Annals of Allergy, Astmas and Immunology, pp. 409-413.
Schmid-Grendelmeier P, Cameri R, Recombinant Allergens for Skin Testing, Int Arch Allergy Immunol 125, 96-111 (2001).
Sobotka "Honeybee venom: Phospholipase A as the major allergen", Abstract of Papers, vol. 53, No. 2, 1974, 1 page.
Sobotka "Allergy to insect stings" J. Allergy Clin. Immunol. Jan. 1976, vol. 57, No. 1, pp. 29-40.
Soldatova, "Molecular Cloning of a New Honeybee Venom Allergen, Acid Phosphatase", J Allergy Clin Immunol Jan. 2000, Abstract 1 page.
Steinberger P. et al. Construction of a Combinatorial IgE Library from a Allergic Patient.J. Biol. Chem. 271, 10967-10972 (1996).
Sudowe, "Efficacy of recombinant adenovirus as vector for allergen gene therapy in a mouse model of type I allergy", Gene Therapy (2002) 9, 147-156.

(56) References Cited

OTHER PUBLICATIONS

Tretter Vet al. Fucose alpha1,3-Linked to the Core Region of Glycoprotein N-Glycans Creates an Important Epitope for IgE from Honeybee Venom Allergic Individuals, Int Arch Allergy Immunol 102, 259-266 (1993).

Valenta R. et al. The Immunoglobulin E-Allergen Interaction: A Target for Therapy of Type I Allergic Diseases. Int. Arch. Immunol. 116, 167-176 (1998).

Varney V.A. et al. Usefulness of immunotherapy in patients with severe summer hay fever uncontrolled by antiallergic drugs. British Medical J. 302, 265-269 (1991).

Vlasak, "Nucleotide sequence of cloned cDNA coding for honeybee prepromelittin", Eur. J. Biochem. 135, 123-126 (1983).

Williams LW, Bock S.A. Skin Testin and Food Challenges in Allergy and Immunology Practice, Clin. Rev. Allergy Immunol. 17, 323-338 (1999).

Wypych, "Analysis of Differing Patterns of Cross-Reactivity of Honeybee and Yellow Jacket Venom-Specific IgE: Use of Purified Venom Fractions" Int Arch Allergy Appl Immunol 1989; 89: 60-66.

Zhang Q. Immune epitope database analysis resource (IEDB-AR) Nucleic Acid Res. 36, W513-W518 (2008).

Habermann et al. "Bienen—und Wespenstiche aus medizinischer Sicht", 4 pages, 1979 (Brief description enclosed).

Kulike, "Zur Struktur und Funktion des Hymenopterenstachels" 1986, 32 pages. (English summary on p. 519).

\* cited by examiner

Fig. 1

```
LOCUS      Api m 3    1122 bp   DNA
SOURCE     Tissue, venom gland
ORGANISM   Apis mellifera
BASE COUNT   362 a    214 c    238 g    308 t
ORIGIN
    1 gaacttaaac aaataaatgt gatattccgg cacggcgata ggatacccga tgagaaaaac
   61 gaaatgtatc cgaagatcc ttatttgtat tatgattttt atccactgga gcgtggcgaa
  121 ttgactaact caggtaaaat gcgagaatat caattggggc aattcttgag agagagatat
  181 ggtgactttt tgggagacat ttacacggaa gaatccgtct cggctctcag ctcgttctac
  241 gataggacga aaatgtctct gcaactcgta ctcgcggcgc tctatccgcc aaataaattg
  301 caacaatgga acgaagatct gaactggcaa ccgatcgcca cgaaatattt gcgccgctac
  361 gaggacaata tcttttttgcc agaagattgt ttgttattta ccatcgaact tgatagagta
  421 tggaatcac cgcgtggaaa gtatgaattc tcgaaatatg acaaattgaa gaaaaaattg
  481 gaagaatgga ccggaaaaaa tatcactacg ccatgggatt attattacat atatcataca
  541 ctggtggctg aacaatcgta cggtcttact ctgccatctt ggacaaataa tatattcccg
  601 agaggagaat tgttcgatgc gacggtattt acgtacaaca taaccaattc gactccttg
  661 ttgaaaaaac tttatggagg tccgcttctt cgaatattca ccaagcatat gttagacgtg
  721 gtatcgggta cgcaaaagaa aaagcgaaag atatacttgt tcagtggaca tgaaagtaat
  781 atcgcctctg tgttgcacgc tcttcaactt tattatcctc acgttcctga atattccagt
  841 tctattataa tggagcttca caatatcgaa ggcactcact acgtaaagat cgtttactac
  901 ttgggtatcc cgtctgaagc gagagaactt caattacccg gctgcgaggt actttgccct
  961 ttgtacaaat atttacaatt gatagagaac gtgataccat cgaacgaaga gttgatctgc
 1021 gataaaagat tcgtcgacga atcggcaaac aatttgtcga tcgaagaatt agatttcgtg
 1081 aaattgaacc taataaggat agcgggtact gagaataagt aa
//
```

Fig 2:

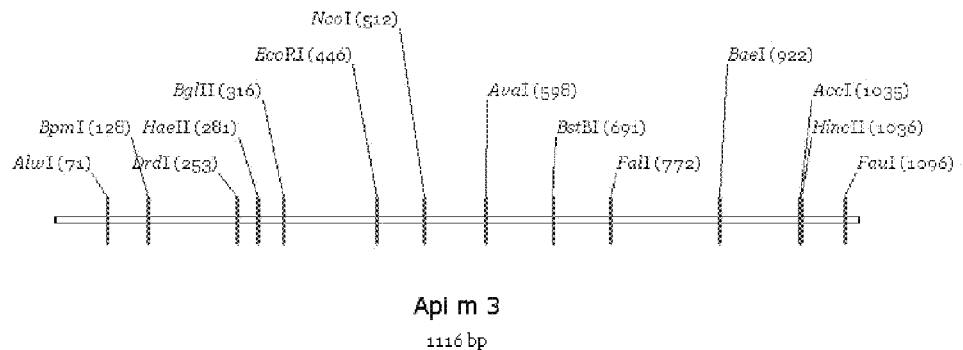

Api m 3
1116 bp

Fig. 3

```
LOCUS       Translatio    374 aa
DEFINITION  Translation of cloned Api m 3
KEYWORDS    TRANSLATED.
SOURCE      Tissue, venom gland
ORIGIN
        1 ELKQINVIFR HGDRIPDEKN EMYPKDPYLY YDFYPLERGE LTNSGKMREY QLGQFLRERY
       61 GDFLGDIYTE ESVSALSSFY DRTKMSLQLV LAALYPPNKL QQWNEDLNWQ PIATKYLRRY
      121 EDNIFLPEDC LLFTIELDRV LESPRGKYEF SKYDKLKKKL EEWTGKNITT PWDYYYIYHT
      181 LVAEQSYGLT LPSWTNNIFP RGELFDATVF TYNITNSTPL LKKLYGGPLL RIFTKHMLDV
      241 VSGTQKKKRK IYLFSGHESN IASVLHALQL YYPHVPEYSS SIIMELHNIE GTHYVKIVYY
      301 LGIPSEAREL QLPGCEVLCP LYKYLQLIEN VIPSNEELIC DKRFVDESAN NLSIEELDFV
      361 KLNLIRIAGT ENK*
```

Fig. 4A

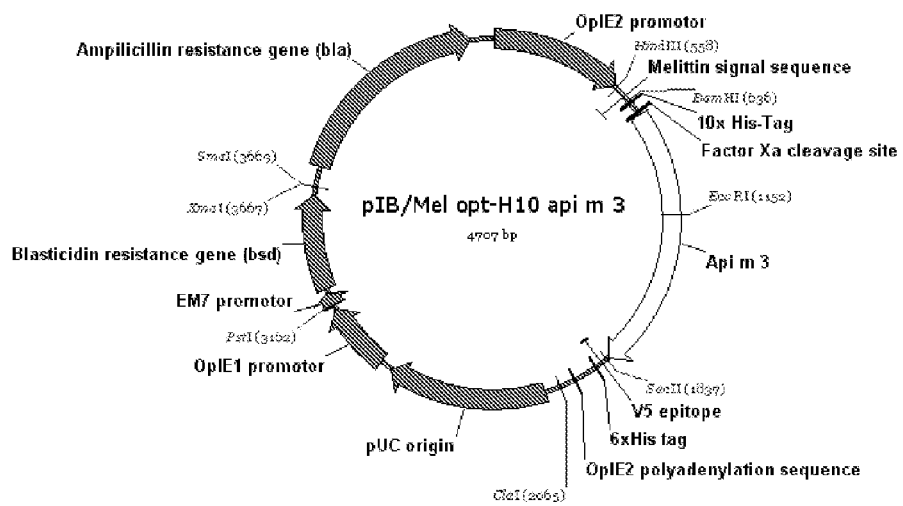

Fig. 4B a) AAGCTTATGAAATTC (SEQ ID NO:14)

```
               M   K   F
b) AAGCTTTCCGCCATGGCGAAATTC (SEQ ID NO:15)
               M   A   K   F  (SEQ ID NO:16)
```

Fig. 5A

| Order of alignment positions (Hoffman) | Order of alignment positions (this invention) | Sequences of published peptide fragments | AA length |
|---|---|---|---|
| 1 | 1,4 | ELKQINVIFRHGDRIPDEKNEMYPKKLEEWTDK (SEQ ID NO: 17) | 33 |
| 2 | 8 | FVDESANNLSIEEIDFVK (SEQ ID NO: 18) | 18 |
| 3 | 2 | LQQWNEDLNWQPIATK (SEQ ID NO: 19) | 16 |
| 4 | 3 | GKYEFSKR (SEQ ID NO: 20) | 8 |
| 5 | - | YNIFAGTWK (SEQ ID NO: 21) | 9 |
| 6 | 6 | LYGGPLLRDNYVGDER (SEQ ID NO: 22) | 16 |
| 7 | 5,7 | DITTPKDYYYIYHTLVAENEYSSCIIMEYHNIEGTHYVKIVYY LGIPSEARELQLPGCEVLCPLEKYLQLIENVIPSNEELICDKR (SEQ ID NO: 23) | 86 |

Fig. 5B

```
                      *        20         *        40         *
Api m 3 : ELKQINVIFRHGDRIPDEKNEMYPKDPYLYYDFYPLERGELTNSGKMREY :  50   (SEQ ID NO: 24)
Hoffman : ELKQINVIFRHGDRIPDEKNEMYPKDPLEWIDK           (SEQ ID NO: 17)
Revised : ELKQINVIFRHGDRIPDEKNEMY                     (SEQ ID NO: 35)

60        *        80         *       100
Api m 3 : QLGQFLRERYGDFLGDIYTEESVSALSSFYDRTKMSLQLVLAALYPPNKL : 100
Hoffman :               DESAN..TEIDEVK    (SEQ ID NO: 18)
Revised :

*       120         *       140         *
Api m 3 : QQWNEDLNWQPIATKYLRRYEDNIFLPEDCLLFTIELDRVLESPRGKYEF : 150
Hoffman : QQWNEDLNWQPIATK   (SEQ ID NO: 19)              (SEQ ID NO: 20)
Revised : QQWNEDLNWQPIATK   (SEQ ID NO: 36)              (SEQ ID NO: 37)

160        *       180         *       200
Api m 3 : SKYDKLKKKLEEWTGKNITTPWDYYYIYHTLVAEQSYGLTLPSWTNNIFP : 200
Hoffman :                         (SEQ ID NO: 21)
Revised :       (KITEWT)  (PDYYYIYHTLVAE)   (SEQ ID NO: 38)

*       220         *       240         *
Api m 3 : RGELFDATVFTYNITNSTPLLKKLYGGPLLRIFTKHMLDVVSGTQKKKRK : 250
Hoffman :                        YGGPLLRIFTKHMLDVVSGTE    (SEQ ID NO: 22)
Revised :                        YGGPLL                   (SEQ ID NO: 39)

260        *       280         *       300
Api m 3 : IYLFSGHESNIASVLHALQLYYPHVPEYSSSIIMELHNIEGTHYVKIVYY : 300
Hoffman :         DYYIYHTLVAENEYSSSIIMELHNIEGTHYVKIVY      (SEQ ID NO: 23)
Revised :                        SSSIIMELHNIEGTHYVKIV      (SEQ ID NO: 40)

*       320         *       340         *
Api m 3 : LGIPSEARELQLPGCEVLCPLYKYLQLIENVIPSNEELICDKRFVDESAN : 350
Hoffman : LGIPSEARELQLPGCEVLCPLEKYLQLIENVIPSNEELICDK
Revised : LGIPSEARELQLPGCEVLCPLEKYLQLIENVIPSNEELICDKRFVDESAN 360        *
Api m 3 : NLSIEELDFVKLNLIRIAGTENK-- : 373
Hoffman :
Revised : NLSIEELDFVK    (SEQ ID NO: 18)
```

Fig 8

Api m 3 (A. mellif.) (SEQ ID NO. 24)

Acph 1 (D. melanog.) (SEQ ID NO. 25)

CG7899-PA (D. melanog.) (SEQ ID NO. 26)

Acph 1: Acph 1 (D. suboscura) (SEQ ID NO. 27)

CG9451-PA (D. melanog.) (SEQ ID NO. 28)

| residues | mass calculated | measured | sequence | |
|---|---|---|---|---|
| 28-34 | 889.52 | 889.55 | QINVIFR | (SEQ ID NO: 29) |
| 50-62 | 1753.81 | 1753.85 | DPYLYYDFYPLER | (SEQ ID NO: 30) |
| 73-81 | 1153.60 | 1153.64 | EYQLGQFLR | (SEQ ID NO: 31) |
| 248-255 | 888.53 | 888.54 | LYGGPLLR | (SEQ ID NO: 32) |
| 260-270 | 1214.62 | 1214.65 | HMLDVVSGTQK | (SEQ ID NO: 33) |
| 321-332 | 1380.75 | 1380.82 | IVYYLGIPSEAR | (SEQ ID NO: 34) |

A. Fig 11
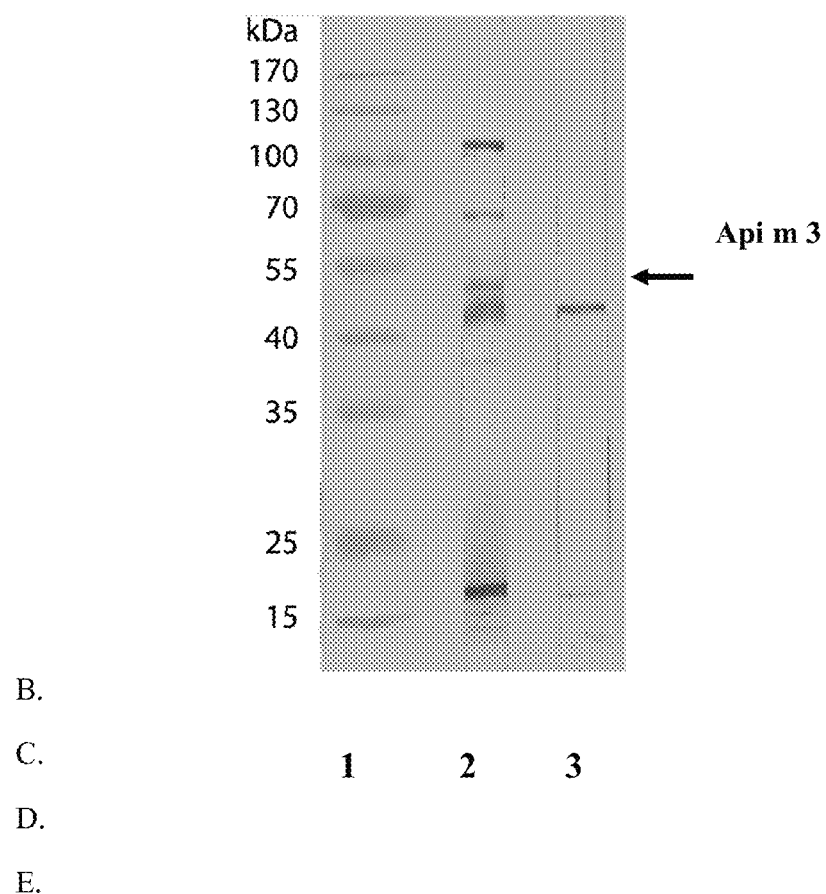
B.
C.
D.
E.

F. Fig 12A
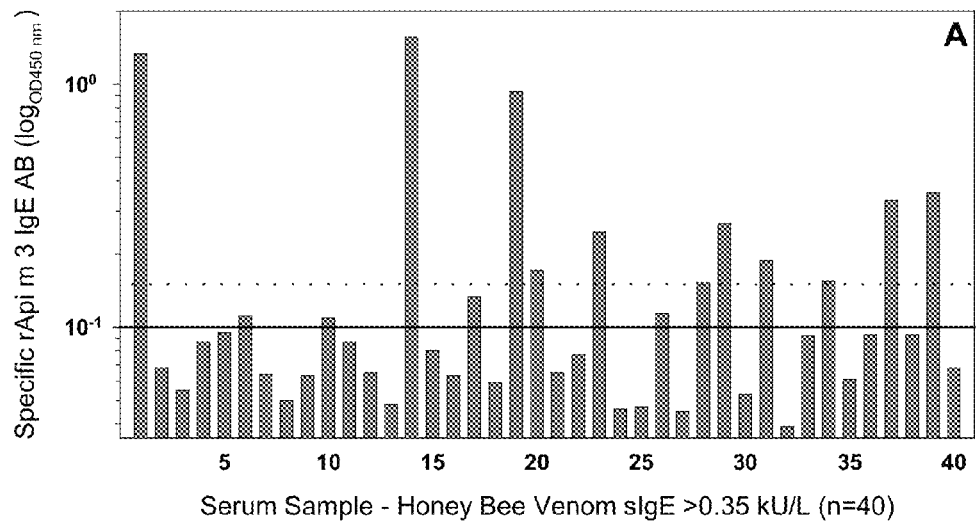
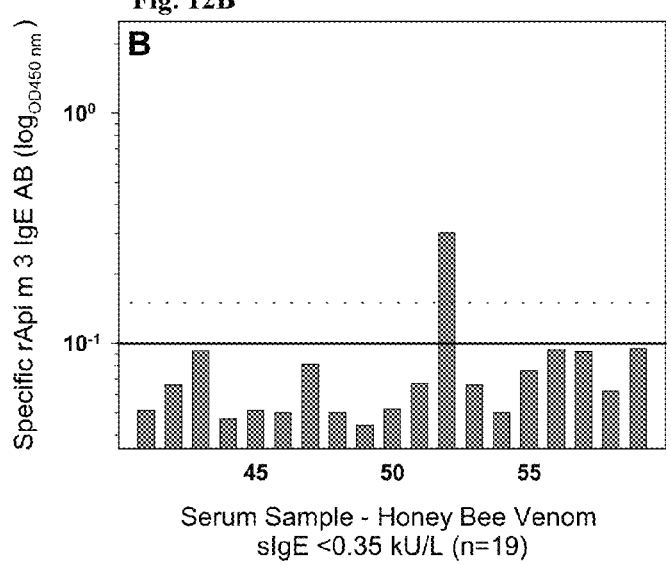
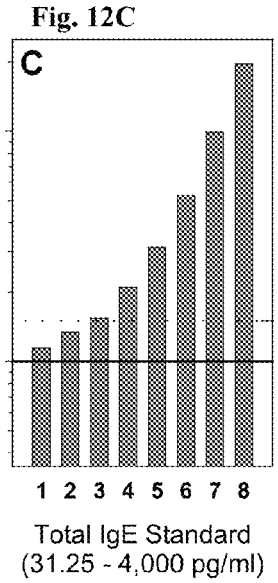

CLONING OF HONEY BEE ALLERGEN

RELATED APPLICATIONS

This application is a continuation-in-part of U.S. patent application Ser. No. 11/301,329 filed Dec. 13, 2005, which claims the benefit under 35 USC 119(e) of U.S. provisional application 60/635,479, filed Dec. 14, 2004.

FIELD OF THE INVENTION

The present invention relates to a recombinant polypeptide capable of binding to IgE from subjects allergic to venom of an insect from the order Hymenoptera having a homology of more than 70% to the amino acid sequence of SEQ ID NO: 2, which is the honey bee allergen Api m3 (acid phosphatase). The invention further relates to nucleic acid encoding the polypeptide, expression vectors, host cells and methods of preparing the polypeptide, as well as diagnostic and pharmaceutical uses thereof.

SUMMARY OF THE INVENTION

It has long been recognised that allergies against insect venoms are relatively common 4-5% of the German population react allergic to insect venoms. In Europe the relevant stinging insects are honey bees (Apis mellifera), wasps (Vespula spp.), bumble bees (Bombus spp.), hornets (Vespa crabo), midges, and horse flies (Helbing et al 2004, Eich-Wanger and Müller 1998). Bees, bumble bees, wasps, and hornets belong to the order Hymenoptera.

These social insects do not normally attack people, but will sting them in self defence if disturbed. Once stung, if the stinger remains in the skin, a honey bee is responsible, while, if no stinger is present, a wasp is likely to be the culprit. The female worker honey bee carries the stinger and dies soon after discharging a sting.

If a bee stings a vertebrate, the stinger will be detached from the insect, but the venom sack will still be attached to the stinger and if not removed, the whole venom volume (up to 50 µl) will be injected into the victim. Wasps can retract the stinger, and only inject about 20 µl venom.

The differences in stinging behaviour are based on natural evolution. Bees collect nectar, whereas wasps and hornets are insect hunters. Therefore, bees need to protect the hive, even against vertebrates like mice or larger animals. The insect dies upon the sting, but will inject the maximum volume of venom, if the stinger is not removed. Wasps and hornets do not have such natural enemies.

Since it is easy to obtain sufficient quantities of material, honey bee venom has been well studied. Honey bee venom contains at least 18 active substances. Melittin, the most prevalent substance, is one of the most potent anti-inflammatory agents known (100 times more potent than hydrocortisone). Adolapin is another strong anti-inflammatory substance, and inhibits cyclooxygenase; it thus has analgesic activity as well. Apamin inhibits complement C3 activity, and blocks calcium-dependent potassium channels, thus enhancing nerve transmission. Other substances, such as Compound X, Hyaluronidase, Phospholipase A2, Histamine, and Mast Cell Degranulating Protein (MSDP), are involved in the inflammatory response to venom, with the softening of tissue and the facilitation of flow of the other substances. Finally, there are measurable amounts of the neurotransmitters Dopamine, Norepinephrine and Serotonin. The water content varies between 55-70%. The pH range is between 4.5-5.5. A summary of the components of bee venom is given in Table 1 (Dotimas and Hider 1987).

The LD50 dose, i.e., the amount of bee venom which causes 50% of the tested individuals to die, is 6 mg venom/kg body weight for mice and rats. This equals 40 stings/kg body weight. For hornets, this factor is around 154-180 stings/kg body weight. Bee venom is 1.7-1.5 more effective than those of hornets (Habermann 1974, Kulike 1986).

Honey bees and wasps of the Hymenoptera order are by far the most frequent cause of serious allergic reactions. Normally, at least more than 50 stings of a bee per children or 100 per adult are necessary to induce life threatening conditions (see above). In case of allergic persons, one sting can be enough to cause death by adverse immunological reactions.

This type of allergy is mediated by IgE antibodies which react to venom components. The possibility, therefore, exists that desensitisation therapy by repeated and progressively increased doses of bee venom components would be successful. Several polypeptides from bee venom have been cloned and expressed as recombinant molecules (Sobotka et al 1974, Sobotka et al 1976, Hoffman and Shipman 1976, Kuchler et al 1989, Gmachl and Kreil 1993, Vlasak et al 1983, Hoffman et al 1977, Kettner et al 1999, King and Spangfort 2000). One component of bee venom, acid phosphatase, is one of the more potent allergic proteins (Arbesman et al 1976). Until now, no information about the complete gene sequence has been published and only initial studies on protein level have been made (Soldatova et al 2000, Barboni et al 1987, Hoffman 1996, Jacobsen and Hoffman 1995).

Barboni et al. (1987) describe two different proteins with acid phosphatase activity from honey bee venom, having a molecular weight of 45 and 96 kDa. Enzymatic activity is partly lost during purification in the gel filtration step. Other publications (Soldatova et al 2000, Barboni et al 1987, Jacobsen and Hoffman 1995) report contrasting data, teaching different fragments of the protein and the corresponding nucleic acid, and coming to different conclusions about the family of phosphatases that honey bee venom acid phosphatase might belong to, either prostatic phosphatases or lysosomal phosphatases. Soldatova et al. (2000) describe the incomplete cloning of a partial cDNA possibly encoding an acid phosphatase from honey bee venom. They report difficulties in cloning and obtaining the full length sequence and do not teach the sequence they seem to have cloned.

In light of the prior art, the person skilled in the art is therefore faced with the problem of providing a nucleic acid suitable for recombinant production of acid phosphatase (api m3) from the venom of an insect from the order Hymenoptera, in particular the honey bee, which can be used in such desensitisation therapy as well as in diagnostic tests for the detection of allergy.

BRIEF DESCRIPTION OF THE DRAWINGS

FIG. 1 shows the nucleotide sequence of the isolated cDNA for Api m 3 in FASTA format (SEQ ID NO: 1).

FIG. 2 shows the predicted restriction enzyme pattern of the isolated cDNA for Api m 3.

FIG. 3 shows the predicted translated amino acid sequence of the isolated cDNA for Api m 3 (SEQ ID NO:2). The underlined peptides can be aligned to prior published fragments. See FIGS. 5A, 5B, and 6.

FIG. 4A shows a vector map of a preferred insect cell expression vector, pIB/Mel opt-H10 Api m 3. The vector was modified to include a N-terminal 10× histidine-tag, cleavable with factor Xa protease as well as the signal sequence of bee melittin for secreted expression. The gene of interest was cloned between the EcoR V and Sac II site. The gene comprises a stop codon at the 3'-end. The expressed protein should be secreted and will have a factor Xa cleavable 10× histidine-tag at the N-terminus.

FIG. 4B shows optimisation of the Kozak sequence for insect cell expression. The former sequence a) was changed into b) to be in accordance with the preferred translation initial sequence (G/A)NNATGG adding an alanine to the N-terminal sequence.

FIG. 5A shows the sequence information of potential peptide fragments of acid phosphatase publicly known prior to this invention. Peptide fragments are listed in order of alignment to human and rat prostate phosphatase as published by Hoffman (1996). The alignment order of fragments to derived sequence is given in the second column. Positions of aligned peptide segments can be taken from FIG. 3 and FIG. 5B, as well as FIG. 6. Highlighted sequence segments in the third column show amino acids present in the Api m 3 sequence. The forth column shows the length of the published peptide fragments.

FIG. 5B shows the corrected alignment of peptides originally postulated by Hoffmann (1996) to Api m 3 and as seen in SEQ ID NOs 17-23.

FIG. 8 Alignment of Api m 3 to acid phosphatase sequences. Shown is the alignment of cloned Api m 3 to different insect acid phosphatases with significant homology. The highest homology with 35% is found for Acph-1 from *D. melanogaster*. Amino acids necessary for acid phosphatase activity and for glycosylation are shaded in grey. The sequence motif 'RHGXRXP' is listed as SEQ ID NO: 41.

FIG. 11 shows an IgE immunoblot of pooled honey bee venom-reactive patient serum with recombinant Api m 3. Lane 1, protein molecular weight standards; lane 2, diluted bee venom; lane 3, purified recombinant Api m 3 derived from insect cell expression.

FIG. 12A Immunoreactivity of 59 individual patient sera with recombinant Api m 3. Shown are the results of an ELISA assay measuring the IgE antibody reactivity with Api m 3. FIG. 12A shows the results for an ELISA assay measuring the IgE antibody reactivity with Api m3 for 40 honey bee venom-sensitized patients (1-40; sIgE to honey bee venom >0.35 kU/L).

FIG. 12B shows the results for an ELISA assay measuring the IgE antibody reactivity with Api m 3 for 19 honey bee venom-negative patients (41-50; sIgE to honey bee venom <0.35 kU/L and to vespid venom >50 kU/L) (51-59; sIgE to honey bee and vespid venom <0.35 kU/L).

FIG. 12C shows an 8-point calibration ELISA standard for total human IgE (31.25; 62.5; 125; 250; 500; 1,000; 2,000; 4,000 pg/ml) for an ELISA assay measuring the IgE antibody reactivity with Api m 3.

DETAILED DESCRIPTION

Figure 4C:
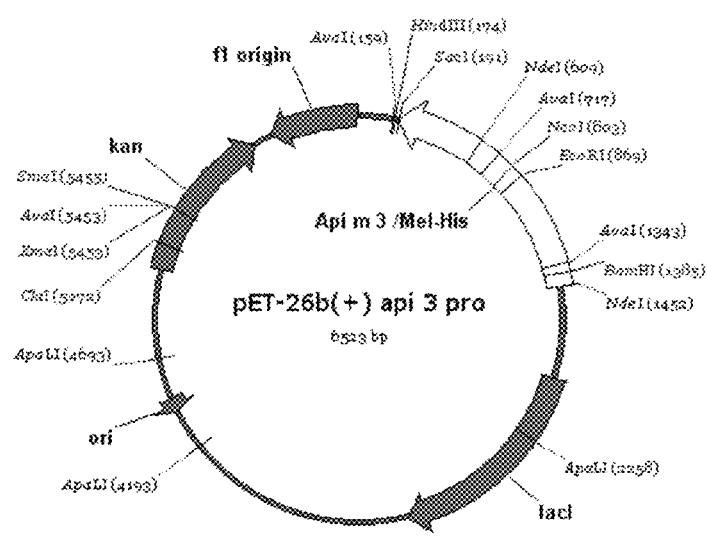
FIG. 4C shows a vector map of a preferred bacterial expression vector, pET26b(+) api 3 pro. The vector was modified to contain the gene of interest between the Sac I and Nde I site. The protein sequence was taken from the verified mammalian expression vector pIB/Mel opt-H10 api m 3.

This problem is solved by the subject matter of the claims.

Specific immunotherapy (desensitization) approaches are well known in the state of the art. In principle, repeated treatments of allergic individuals with suitable, normally progressively increased doses of allergen diverts the immune response to one dominated by T cells that favour the production of IgG and IgA antibodies over production of IgE antibodies. The IgG and IgA antibodies are thought to desensitise the subject by binding to the small amounts of allergen normally encountered, and preventing the allergen from binding to IgE. Desensitisation to honeybee venom is relatively successful (e.g., Hunt et al 1978).

However, there are serious limitations to the use of currently available allergen preparations for specific immunotherapy. While multiple studies have demonstrated that successful SIT requires administration of high doses of allergens, effective dosages are limited by potential systemic reactions. As a result, specific immunotherapy usually requires a treatment period of 2 to 3 years, over which the allergen preparation is administered at slowly increasing dosages followed by several injections of the final maintenance dose. Since the compliance of patients and doctors is very low due to the tedious and potentially harmful procedure, there is a need in the field for modified allergens capable of providing protection without the danger of serious side-effects.

In order to avoid undesirable systemic reactions on specific immunotherapy with natural allergens, there has been continued interest in the development of modified allergens with reduced allergenic activities for immunotherapy. In one approach T cell epitopes are used to modulate allergen-specific immune responses. It has been observed in vivo in mice for the allergen Fel d 1 (cat hair), Der p 1 (acarian: *Dematophagoides pterissimus*) and Bet v 1 (birch pollen) that the nasal, oral or subcutaneous administration of peptides carrying T cell epitopes of these allergens inhibits the activation of the specific T lymphocytes (Briner et al 1993; Hoyne et al 1993; Bauer et al 1997). Based on these results allergen peptide fragments capable of stimulating T lymphocytes in allergic patients were evaluated in clinical sudies. In the case of the major honeybee venom allergen Api m 1 fragments 50-69 and 83-97 have been described as being active during a study comprising a single patient (Dhillon et al. 1992). In a study comprising forty patients (Carballido et al 1993) Api m 1 fragments 45-62, 81-92 and 113-124 proved to be active. However, these three fragments proved to be T cell epitopes for only 25 to 45% of the patients, pointing to the existence of other epitopes. Nevertheless, the three peptides have been used successfully for desentization of five allergic patients whose T lymphocytes proliferated in the presence of these peptides (Müller et al 1998). No serious systemic effect was observed and the patients became tolerant to honeybee stings. This demonstrates the benefit of using peptides for desensitization. Therefore, there is a need in the field to identify peptide fragments of Api m 3 capable of stimulating T lymphocytes in patients allergic to honeybee venom.

In another approach, B cell epitopes of allergens are modified to decrease the risk of potential systemic reactions. B cell epitopes of poteinaceous allergens can include native protein structures (conformational or discontinuous or topographic epitopes), linear peptides (linear epitopes) and carbohydrates. The conformational type consists of amino acid residues which are spatially adjacent but may or may not be sequentially adjacent. The vast majority of IgE epitopes has been reported to be of the conformational type (King 1990). The linear type consists of only sequentially adjacent residues. However, even linear B cell epitopes are often conformation-dependent, and antibody-antigen interactions are improved when the epitope is displayed in the context of the folded protein. It is believed that the entire accessible surface of a protein molecule can be recognized as epitopes by the antigen receptor of B cells, although all epitopes are not necessarily recognized with equal likelihood (Benjamin et al 1984).

The aim of modification of B cell epitopes is to decrease the allergenicity while retaining its immunogenicity. Since allergenicity depends on the interaction of a multivalent allergen with basophil- or mast cell-bound IgE antibodies, allergenicity can be reduced by decreasing the density of B cell epitopes. One approach is by partial or complete denaturation of allergens on chemical modification because the vast majority of B cell epitopes are of the discontinuous type, being dependent on the native conformation of proteins. However, there are serious limitations to the use of such molecules. While linear T cell epitopes are preserved, the surface structure is not maintained and, thereby, the capacity of such molecules to stimulate an allergen-specific non IgE antibody response is severely limited. Similar considerations apply to an approach in which the accessibility of B cell epitopes is reduced by polymerization on formaldehyde or glutaraldehyde treatment or by attachment of non-immunogenic polymers. Usually near-complete loss of the discontinuous B cell epitopes occurs when allergens are modified with >100-fold reduction in allergenicity.

A more promising approach is to modify by site-directed mutagenesis identified discontinuous B cell epitopes recognized by IgE antibodies. While several IgE epitopes could be determined by mapping with synthetic overlapping peptides synthesized according to the allergen amino acid sequence, many relevant IgE epitopes could not be identified because peptides frequently fail to display conformations mimicking discontinuous epitopes. Programs have been developed for the prediction of both linear and conformational B cell epitopes (Zhang et al 2008). For example, DiscoTope is a method for discontinuous epitope prediction that uses protein 3D structural data as input. It is based on amino acid statistics, spatial information and surface accessibility for a set of discontinuous epitopes determined by X-ray crystallography of antibody-proteinaceous antigen-complexes. However, available data are limited and not suited for a reliable identification of epitopes of the conformational type on the Api m 3 molecule. There is no doubt that naturally occurring IgE antibodies represent ideal tools for structural analyses of IgE epitopes. However, the number of monoclonal allergen-specific IgE antibodies isolated from blood lymphocytes of allergic patients so far is extremely limited. In an alternative approach, animal derived monoclonal allergen-specific antibodies can be useful to identify IgE epitopes. For example, from a panel of mouse monoclonal antibodies that effectively inhibited binding of birch pollen allergen Bet v 1 to specific IgE, several monoclonal antibodies identified a continuous epitope within an exposed surface area of Bet v 1 that could be part of a discontinuous IgE epitope (Lebecque et al 1997) Provided such antibodies bind to Bet v 1 with high affinity, they represent useful tools for further structural analyses by X-ray diffraction of crystals obtained from allergen-antibody complexes. Although the surface area recognized by animal-derived allergen-specific antibodies may not be identical with that recognized by human IgE antibodies, both areas are closely related as indicated by the inhibition experiments. Therefore, structural information obtained from the analysis of such allergen-antibody complexes provide a valuable basis for the modification of IgE epotopes by site-directed mutagenesis. One problem of this approach, however, is the need of a panel of high affinity antibodies with different epitope specificities for each allergen to allow for a detailed analysis of the total spectrum of potential IgE epitopes. Assuming that a B cell epitope takes up an area of approximately 900 $A^2$, the vast majority of allergens is likely to display more than one IgE epitope. Therefore, there is a need in the field to develop high affinity Api m 3-specific antibody panels that are capable of inhibiting IgE binding.

Another serious problem associated with the design of a hypoallergenic Api m 3 molecule for an improved immunotherapy is the lack of understanding of the immune response that guarantees a lasting protection after specific immunotherapy. The aim to decrease the allergenicity of a given allergen while retaining its immunogenicity is widely accepted, but the term immunogenicity remains to be defined. Evaluation of modified recombinant allergens with a strongly reduced IgE reactivity that display the full spectrum of linear T cell epitopes but a different surface structure as compared to the corresponding natural allergen, have demonstrated that such molecules are capable of reducing specific IgE development towards the native allergen (Niederberger et al 2004; Karamloo et al 2005) However, a long lasting protective effect after treatment with these molecules has not been demonstrated. Apparently, the capacity of recombinant allergens to stimulate a long lasting protective allergen-specific non IgE antibody response requires also a surface structure that is closely related to that of the corresponding natural allergen. Since disruption of IgE epitopes is associated with a significant alteration of the surface structure, there is a need in the field to identify those surface structures of allergens that mediate an appropriate non-IgE response for a long lasting protection. There is a particular need in the field to identify those surface structures of Api m 3 that mediate an appropriate non-IgE response for a long lasting protection.

In particular, the present invention provides a nucleic acid encoding a polypeptide capable of binding to IgE from subjects allergic to venom of an insect from the order Hymenoptera wherein the polypeptide has a homology of more than 70% to the amino acid sequence of SEQ ID NO: 2 (note: "SEQ ID NO" relates to code <400> in the attached sequence listing under WIPO standard ST.25).

In one embodiment, the nucleic acid comprises a sequence homologous to the sequence of SEQ ID NO: 1 (derived from *Apis mellifera*), which is a naturally occurring homologous sequence from an other insect from the order Hymenoptera. The invention also refers to the recombinant proteins encoded by the nucleic acids of the invention.

Preferentially, the degree of homology to the amino acid sequence of SEQ ID NO: 2 is more than 75%, more than 80%, more than 85%, more than 90%, more than 95% or more than 99%. The sequence homology is determined using the clustal computer program available from the European Bioinformatics Institute (EBI). Most preferentially, the polypeptide encoded by the nucleic acid has the amino acid sequence of SEQ ID NO: 2. This polypeptide is designated Api m 3. In particular, the nucleic acid comprises or has the nucleotide sequence of SEQ ID NO: 1.

In the context of this application, sequence identity is used interchangeably with homology.

In the context of the present invention, the terms "polypeptide" and "protein" are used interchangeably, without any limitation as to the number of amino acids linked. The polypeptides may also comprise non-naturally occurring amino acids.

Throughout this specification, the polypeptides encoded by the nucleic acid of the invention have to be capable of binding to IgE from subjects allergic to venom of an insect from the order Hymenoptera. Of course, the skilled person understands that this binding takes place in the area of sequence identity or homology.

Following unsuccessful attempts to clone the full length sequence of Api m 3 following the common deduced primer strategy (cf. Soldatova et al., 2000) based on the peptide fragments found by Hoffmann, 1996, and their postulated sequence (Hoffmann, 1996). A completely different approach was chosen in the present invention. Using nucleic acid sequences derived from the peptide sequences published by Hoffman, small virtual probes of partial deduced sequences were constructed, which were used to scan the published bee genome for targets. Two regions on different truncated chromosome 16 sequences matched the probes. Scanning of these regions with bioinformatic tools revealed possible open reading frames and gene sequences. Scanning for a potential sequence cleavage site led to the putative N-terminus of the Api m 3 gene. Primers were then designed according to the proposed protein N- and C-terminus. These primers were used to amplify the gene from bee venom gland cDNA synthesized from total RNA with oligodT(20) primers. The amplification was successful and resulted in a DNA fragment of the expected size. The identity of the DNA was verified by sequencing, molecular weight calculation and alignment to the homologous acid phosphatases of human as well as rat sequences and the proposed peptide fragments. The protein identity was also verified.

From the resulting full length cDNA sequence, it is clear the classical approach had to fail, as Hoffman erred in several points. For example, he chose an incorrect alignment of the peptide fragments (cf. FIG. 5), erroneously thought that several peptides that are in fact separated by other peptides were contiguous, and postulated existence of a fragment that does not belong to the acid phosphatase. In fact, using primers based on peptides 1 and 7, as proposed by Hoffman, one would expect to amplify a short fragment covering only the peptide sequence around amino acids 200 and 230 of the consensus sequence.

The social insects from the order Hymenoptera that commonly interact with man are members of the superfamilies Apoidea and Vespoidea, bees and wasps (Hoffman 1996). The Vespoidea include the social wasps and hornets, Vespidae, as well as ants, Formicidae. Important wasps comprise yellowjackets of the genus *Vespula*, hornets of the genera *Dolichovespula* and *Vespa* and paper wasps of the genus *Polistes*. Bees comprise, e.g., honey bees, *Apis mellifera*, and bumble bees of the species *Bombus terrestris*. In the context of the present invention, an insect from the order Hymenoptera can be from any of these species, but according to a particular embodiment, the insect is a bee from the genus *Apis*. Most preferably, the bee is the honey bee, *Apis mellifera*.

Other species from the order Hymenoptera produce similar allergens with antigenic cross reactivity and a high degree of amino acid homology (Wypych et al 1989, Castro et al 1994, Hoffman et al 1988). Thus the present invention not only extends to the Api m3 allergen from *Apis mellifera* but also to homologous Hymenoptera allergens.

In particular, the polypeptides encoded by the nucleic acids of the invention have to be capable of binding to IgE from subjects allergic to venom of *Apis mellifera*. The subjects are commonly reactive to the Api m3 antigen, acid phosphatase from bee venom. For the purpose of testing, serum or purified IgE from such allergic subjects are contacted with the polypeptide, and specific binding of the polypeptide to the antibodies is detected. Such a test can, e.g., be an ELISA. For verifying the reactivity of the polypeptides with IgE antibodies, serum or IgE from several subjects are pooled, preferentially, from 5 to 20 subjects.

The nucleic acids of the invention can be either DNA or RNA.

In one embodiment, the invention also provides a nucleic acid, which is a fragment having a length of more than 255 nucleotides of a nucleic acid encoding a polypeptide having a homology of more than 70% to the amino acid sequence of SEQ ID NO: 2, wherein the fragment encodes a polypeptide capable of binding to IgE from subjects allergic to venom of an insect from the order Hymenoptera. Preferably, the nucleic acid is a fragment having a length of more than 255, more preferably of more than 600, more than 700 or more than 800 nucleotides of a nucleic acid encoding a polypeptide having the amino acid sequence of SEQ ID NO: 2.

In another embodiment, a nucleic acid fragment (polynucleotide) is provided that comprises at least 15 contiguous nucleotides of the nucleic acid encoding a polypeptide having the amino acid sequence of SEQ ID NO: 2, wherein the polynucleotide is selected from the group consisting of nucleotides 78 to 299, 348 to 437, 459 to 476, 555 to 671, 696 to 830 or 1086 to 1121 of said nucleic acid, wherein the numbering corresponds to the region encoding said polypeptide. Specifically, said nucleic acid has the nucleotide sequence shown in SEQ ID NO: 1. Preferentially, the nucleotides are from the region of nucleotides 555 to 671 or 696 to 830. Alternatively, the nucleic acids encode polypeptides that are capable of binding to IgE from subjects allergic to venom of an insect from the order Hymenoptera, and comprise at least 15, preferably at least 18, 21, 24, 27, 30, 45, 60 or more nucleotides of a nucleic acid more than 70%, more than 80% or more than 90% homologous or identical to the nucleic acid shown in SEQ ID NO: 1, except for the nucleic acids from the group consisting of nucleotides 1 to 104, 189 to 142, 300 to 347, 426 to 449, 504 to 530, 672 to 719 and 774 to 1031 of the nucleic acid shown in SEQ ID NO: 1 or except for the nucleic acids encoding the polypeptides shown in FIG. 5. Additionally, such nucleic acids consisting of nucleotides 1 to 77, 438 to 458, 477 to 494, 504 to 554, 672 to 695, and 831 to 1085 of the nucleic acid shown in SEQ ID NO: 1 are provided.

Preferentially, the nucleic acid comprises 15 to 240, 15 to 90, 18 to 60, 21 to 30, more preferably at least 18, 21, 24, 27, 30, 60, 90 or more contiguous nucleotides from the above regions.

Alternatively, a nucleic acid is provided which encodes a polypeptide having more than 70% homology to the polypeptide encoded by said at least 15 contiguous nucleotides, wherein the polypeptide is capable of binding to IgE from subjects allergic to venom of an insect from the order Hymenoptera. In particular, this polypeptide comprises at least 5, preferably at least 6, 7, 8, 9, 10, 15, 20 or more amino acids of a polypeptide more than 70%, more than 80% or more than 90% homologous or identical to a polypeptide selected from the group consisting of amino acid 26 to 99, 116 to 145, 153 to 158, 185 to 223, 232 to 276 or 362 to 373 of the polypeptide shown in SEQ ID NO: 2. Alternatively, the polypeptides encoded by the nucleic acids are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2, except for the polypeptides from the group consisting of amino acids 1 to 34, 63 to 80, 100 to 115, 142 to 149, 168 to 176, 224-239 and 258 to 343 of the polypeptide shown in SEQ ID NO: 2 or except for the polypeptides shown in FIG. 5. Additionally, such polypeptides consisting of amino acids 1 to 25, 146 to 152, 159 to 164, 168 to 184, 224 to 231, and 277 to 361 are encoded by the nucleic acids.

In one embodiment, the invention also provides a polypeptide encoded by a nucleic acid of the invention. Preferentially, the polypeptide is a full length acid phosphatase from the venom of an insect from the order Hymenoptera. In particular, the polypeptide has an homology of more than 70%, more than 75%, more than 80%, more than 85%, more than 90%, more than 95% or more than 99% to the amino acid sequence of SEQ ID NO: 2. Most preferred is a polypeptide having the amino acid sequence of SEQ ID NO: 2. Although not essential, it is preferred that the polypeptide has acid phosphatase activity. This activity can be tested, e.g., according to the method described by Barboni et al 1987.

Alternatively, the polypeptide is a fragment of the full length protein capable of binding to IgE from subjects allergic to venom of an insect from the order Hymenoptera having a length of more than 85, more than 200 or more than 250 amino acids. Other fragments are provided, wherein the polypeptides are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to a polypeptide selected from the group consisting of amino acid 26 to 99, 116 to 145, 153 to 158, 185 to 223, 232 to 276 or 362 to 373 of the polypeptide shown in SEQ ID NO: 2. Alternatively, the polypeptides are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2, except for the polypeptides from the group consisting of amino acids 1 to 34, 63 to 80, 100 to 115, 142 to 149, 168 to 176, 224-239 and 258 to 343 of the polypeptide shown in SEQ ID NO: 2 or except for the polypeptides shown in FIG. 5. Additionally, such polypeptides consisting of amino acids 1 to 25, 146 to 152, 159 to 164, 168 to 184, 224 to 231, and 277 to 361 are provided.

In a preferred embodiment, the invention provides T-cell epitope-containing oligopeptides of at least 9 amino acids corresponding to a consecutive amino acid sequence within the Api m 3 molecule wherein the peptides are capable of stimulating T-cells of subjects allergic to Api m 3. Such peptides of the invention are preferably immunomodulatory peptides as well in that they induce T-cell anergy when administered to a subject allergic to Api m 3, or otherwise affect the immune response of the subject. Preferably, the amino acid sequence of the T-cell epitope-containing oligopeptide corresponds to a consecutive amino acid sequence of a polypeptide having the amino acid sequence of SEQ ID NO: 2, wherein the T-cell epitope-containing oligonucleotide is selected from the group consisting of 15 contiguous amino acid residues as defined in Tables 3 and 4 of said polypeptide, wherein the numbering corresponds to the region of said polypeptide.

T-cell stimulating activity can be tested by culturing T-cells obtained from an individual sensitive to the Api m 3 polypeptide, fragments, and analogs thereof described herein, with the Api m 3 polypeptide, fragments, and analogs thereof, and determining the presence or absence of proliferation by the T-cells in response to the peptide as measured by, for example, uptake of tritriated thymidine. Stimulation indices for responses by T-cells to peptides useful in methods of the invention can be calculated as the maximum counts per minute (cpm) taken up in response to the peptide divided by the cpm of the control medium. For example, a peptide derived from a protein allergen may have a stimulation index of about 2.0. As a result, a stimulation index of at least 2.0 is generally considered positive for purposes of defining peptides useful as immunotherapeutic agents. Preferred peptides have a stimulation index of at least 2.5, more preferably at least 3.5 and most preferably at least 5.0.

Preferably, the polypeptide of the invention is recombinantly expressed. This has the advantage, e.g., that the polypeptide can be expressed as a fusion protein linked to an additional polypeptide. For example, the polypeptide or fusion protein is attached to a signal sequence ensuring its secretion into the extracellular space or supernatant of the cultured cells, where appropriate. Due to novel techniques in molecular biology, the use of recombinant proteins in therapy and diagnostics is expected to increase the efficiency and diagnostic value in these medical applications (King 1990, Müller 2001, Müller 2002).

Depending on the host cell producing the recombinant protein, the protein is glycosylated (after expression in mammalian or yeast cells) or non-glycosylated (after expression in bacterial cells). The glycosylation pattern can vary depending on the host cell used, and can thus differ from the glycosylation pattern of natural acid phosphatase isolated from bee venom. In one alternative, the glycosylation pattern is identical to the glycosylation pattern of acid phosphatase isolated from bee venom. Glycosylation can have profound effects on the binding of specific antibodies.

When expressed in bacterial cells, the polypeptide of the invention lacks glycosylation. The protein thus differs from the native protein in respect to epitope presentation, and potentiality for folding and functionality. It was shown that carbohydrates can represent IgE epitopes and contribute to observed non-specific cross-reactivity of allergens, e.g., between bee and wasp proteins, due to similar features of the carbohydrate chains (Huby et al 2000, Tretter et al 1993, Hemmer et al 2004). The cross-reactivity is one reason for false positive results in in vitro immunological tests (Petersen and Mundt 2001). Expression of the non-glycosylated polypeptide eliminates these false positives, and can therefore be used to advantage in diagnostic and therapeutic applications.

The glycosylation pattern in eukaryotic cells other than insect cells, e.g., in mammalian cells, also varies from the glycosylation pattern of the native protein (Jenkins et al 1996). Even in insect cells, the glycosylation pattern is likely to be different due to overexpression of the protein.

Sequence analysis of Api m 3 shows that the protein comprises three putative glycosylation sites of the sequence Asn-Xaa-Ser/Thr. In one embodiment, the polypeptides of the invention comprise mutated glycosylation sites instead of glycosylation sites. In particular, in a mutated glycosylation site, the Asparagine (Asn) in the glycosylation site(s) can be exchanged against any other amino acid, preferably against Glutamine (Gln) (Elbein et al 1991). Alternatively, in a mutated glycosylation site, the Serine (Ser) can be exchanged against another amino acid or deleted. Accordingly, the invention also provides a nucleic acid encoding a polypeptide of the invention comprising at least one, preferably 2, or 3 mutated glycosylation sites instead of glycosylation sites. Most preferably, all glycosylation sites are mutated.

Using native Api m 3 in diagnostic assays for detecting allergy, e.g., to bee or wasp venom, cross-reactivity is a big problem. Based on the state of the art using native purified Api m 3 as an antigen in diagnostic tests, the skilled person was unable to differentiate between patients that had been sensitized to bee venom, patients that had been sensitized to wasp venom, and patients that had been sensitized to both. This differentiation is important, because, in case, e.g., a bee allergy is incorrectly diagnosed, a desensibilization therapy might be prescribed which then in fact serves to sensitize the patient to epitopes of bee allergen he was not previously allergic to.

The present invention now allows preparation of recombinant proteins that are useful in diagnostic tests to differentiate between such patients, because it provides recombinant antigens that are not bound by sera of some patients previously diagnosed as allergic to native Api m3 of honey bee venom. The expressed proteins exhibit epitopes that react with IgE antibodies to native Api m 3, but they do not react with all IgE antibodies that bind to native Api m 3.

As mentioned above, cross-reactivity is mainly due to the glycosylation of the bee protein, the sugar patterns being similar to glycosylation of e.g., wasp proteins.

Figure 14:
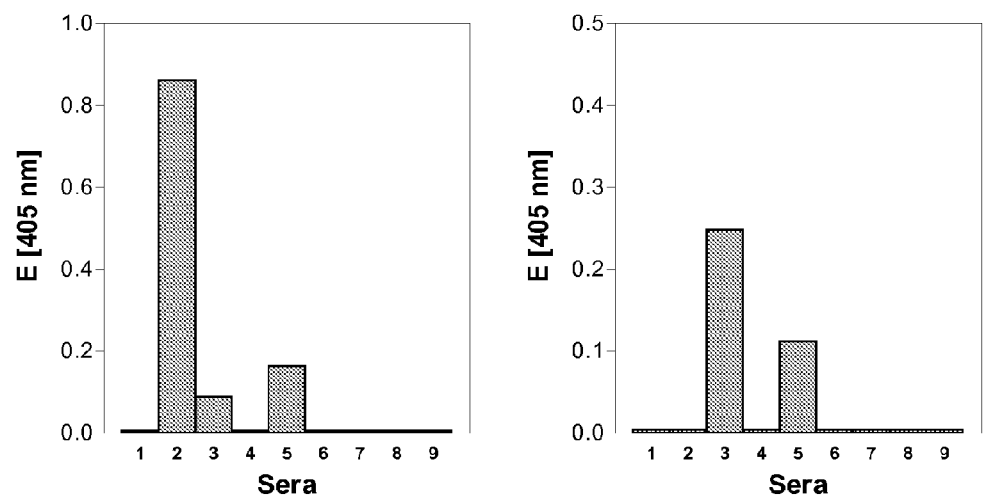
FIG. 14 shows the detection of prokaryotically produced Api m 3 with IgE from sera of honeybee venom-allergic individuals. Experimental conditions are described in Example 6. Shown are data after subtraction of background values.

The inventors have shown that unglycosylated Api m 3, e.g., expressed in procaryotes, provides IgE epitopes as the proteinaceous part of native Api m 3. Furthermore, as shown in FIG. 14, both prokaryotic Api m 3-fusion constructs exhibit a different reactivity to IgE in sera from patients with honeybee venom allergy. Based on these data both constructs provide a different set of IgE epitopes indicating a different folding structure. Such fusion proteins are extremely valuable in assessing sensitization of patients to the proteinaceous part of Api m 3. The differential reactivity of both fusion proteins to IgE antibodies as compared to the reactivity of native Api m 3 purified from bee venom, clearly demonstrates that recombinant, e.g., non-glycosylated Api m 3 fusion proteins provide novel means to eliminate carbohydrate mediated cross-reactivity, thereby eliminating potentially false positives in the diagnosis of honeybee venom allergy.

The results shown in the examples also demonstrate, that, similarly, recombinant Api m 3 molecules expressed in HighFive and SF9 insect cells are recognized to a different extent by IgE in sera from patients allergic to both honeybee and wasp venom.

Figure 15:
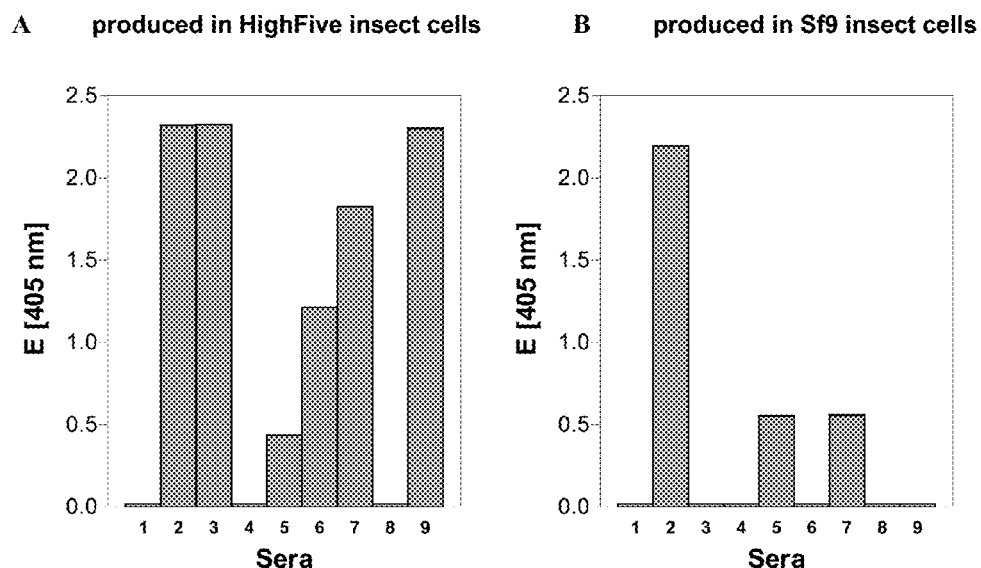
FIG. 15 shows the detection of Api m 3 produced in insect cells (HighFive insect cells in A and Sf9 insect cells in B) with IgE from sera of honeybee venom-allergic individuals. Experimental conditions are described in Example 6. Shown are data after subtraction of background values.

As explained above, recombinant Api m 3 molecules expressed in insect cells (e.g., HighFive cells and SF9 cells) are glycosylated, but the glycosylation pattern provided by both insect cell lines to Api m 3, exhibits significant differences. As shown in FIG. 15, the two glycosylated Api m 3 molecules expressed in HighFive insect cells and SF9 insect cells exhibit a different reactivity to IgE in sera from patients with honeybee venom allergy. Furthermore, FIG. 16 demonstrates that both molecules are recognized to a different extent by IgE in sera from patients allergic to both honeybee and wasp venom. This observation is important, since both molecules allow an improved evaluation of carbohydrate based cross-reactivity of IgE antibodies.

Figure 16:
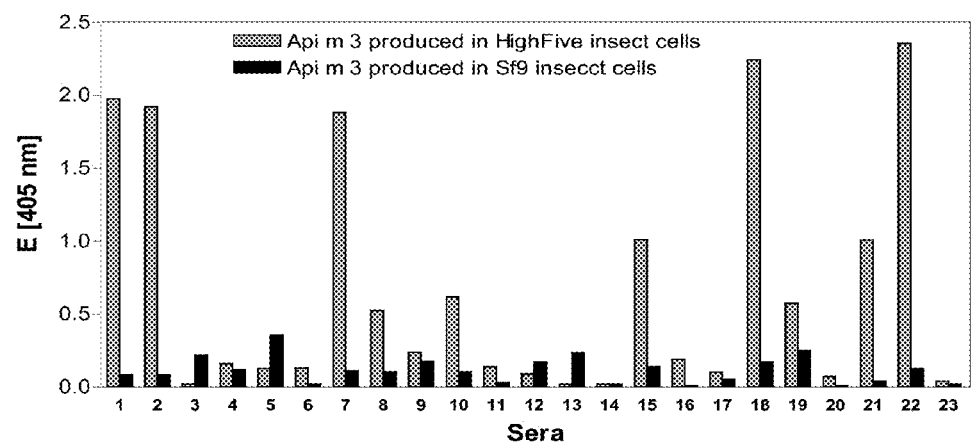
FIG. 16 shows the detection of Api m 3 produced in Sf9 and HighFive insect cells with IgE from sera of patients allergic to both honeybee and wasp venom. Experimental conditions are described in Example 6. Shown are data after subtraction of background values.

In contrast to the data obtained with Api m 3 produced in HighFive insect cells, IgE antibodies in sera from patients allergic to both honeybee and wasp venom recognize Api m 3 produced in SF9 insect cells to a much lesser extent (see FIG. 16). Although Api m 3 produced in SF9 insect cells is also recognized by IgE in 15 of 23 (65%) of these sera, the IgE reactivity is very low as compared to the IgE reactivity towards Api m 3 produced in HighFive insect cells. The residual reactivity of IgE antibodies in sera from patients allergic to both honeybee and wasp venom could be due to those patients possessing IgE antibodies recognizing the proteinaceous part of Api m 3. The recombinant proteins produced according to the invention thus for the first time allow differentiation between allergic patients having antibodies binding to different epitopes of the antigen, which can lead to clearer diagnosis of allergies and potential cross-reactivity.

The present invention also relates to an expression vector comprising a nucleic acid of the invention operationally linked to an expression control sequence. In one alternative, the nucleic acid is linked in frame to a nucleic acid encoding an additional polypeptide, so the expression vector can be used for expression of a fusion protein. The additional polypeptide can be selected from the group comprising a poly-Histidine tag (His tag), glutathione-S-transferase, β-galactosidase, a cytokine, and an IgG-Fc. In particular, tags that simplify purification of the recombinant protein, e.g., a His tag, are employed. Such a tag may be cleaved off after purification of the protein.

Alternatively, it can be beneficial for therapeutic applications to express the polypeptide of the invention linked to a therapeutic polypeptide, e.g. a cytokine. For example, a fusion protein with a cytokine enhancing $T_H1$ and down-regulating $T_H2$ responses or inducing class switch to IgG, such as IFN-γ, IL-10, IL-12 or TGF-β, can improve efficiency of desensitisation. If the expression vector is used for gene therapy, it is envisaged to use sequences rich in CpG (unmethylated cytosine guanidine dinucleotides), which promote $T_H1$ responses. Additionally or alternatively, the polypeptide of the invention can be linked to another polypeptide or protein, such as in the form of a fusion protein or as separate proteins expressed by the same vector. Preferably, the further polypeptides or proteins are other Hymenoptera venom proteins or antigenic fragments thereof.

The expression vector can be suitable for expression in different cell types, such as bacterial, yeast or mammalian cells. Preferentially, the vector is suitable for expression in insect cells, e.g., HighFive insect cells (Invitrogen, Karlsruhe, Germany). Alternatively, especially for gene therapy applications, the vector is suitable for expression in human cells. In this context, the expression of the encoded polypeptide can be directed by the choice of a suitable expression control sequence, e.g., an expression control sequence mainly or specifically operational in different cell types, such as lymphoid cells, for example dendritic cells, B cells or macrophages.

In one embodiment of the invention, the expression vector is pIB/V5-His (Invitrogen, Karlsruhe, Germany, Invitrogen Manual: InsectSelect BSD System with pIB/V5-His, Version G, 30 May 2003).

In particular, the vector can be pIB/Mel opt-H10-Api m3, comprising the Api m3 cDNA sequence (SEQ ID NO: 1), which was modified to facilitate isolation and purification. A melittin signal sequence for secretion of the recombinant protein was added and the Kozak sequence was optimised for higher expression rates in insect cells (see FIG. 4 and Example 2). Alternatively, other signal sequences can be used for secretion of the protein. The expression vector can also be a different plasmid or a viral, e.g., baculoviral or adenoviral, vector. The expression vector further comprises a stop codon and a polyadenylation signal.

The present invention further relates to a host cell comprising said expression vector. This host cell can be a bacterial, yeast or mammalian cell, in particular an insect cell.

A method of producing a polypeptide encoded by a nucleic acid of the invention is provided, wherein the host cell is cultured under appropriate conditions for expression of said polypeptide and said polypeptide is purified. If the polypeptide is a fusion protein with a fusion partner facilitating purification, e.g., a His Tag or a GST-tag, a corresponding affinity column can be used for purification, e.g., a $Ni^{2+}$ or glutathione affinity column. For purification of an IgG fusion protein, a protein A or protein G column is suitable.

The expression vector of the invention can be used for the preparation of a pharmaceutical composition for treating subjects allergic to the venom of an insect from the order Hymenoptera. Treatment regimens using gene therapy approaches to desensitisation are known in the state of the art (e.g., Sudowe et al 2002).

The present invention also relates to a mutant Api m 3 molecule comprising a reduced IgE binding capacity with limited impairment of the residual surface structure important for IgG and IgA immunological responses.

In one embodiment, the present invention provides methods for identification and modification via site-directed mutagenesis of those amino acid residues involved in the interaction of the polypeptides of this invention with human IgE, IgG and IgA antibodies. In particular, the present invention provides compositions comprising recombinant antibodies wherein each composition is capable of binding to all epitopes recognized by human IgE, IgG (including IgG4) and IgA antibodies, a method of obtaining such a composition and the use of individual antibodies of such a composition as tools for the design of a hypoallergenic Api m 3 molecule for specific immunotherapy.

In a specific embodiment, antibody compositions capable of binding to all epitopes of the Api m 3 polypeptide, fragments and analogs thereof that are recognized by human IgE antibodies, are utilized to identify and modify by site-directed mutagenesis those amino acid residues involved in the interaction with allergen-specific human IgE antibodies, thereby eliminating or decreasing the allergenicity of the Api m 3 polypeptide, fragments and analogs thereof in a structure-based approach. By site-directed mutagenesis of amino acid residues essential for the allergen-IgE antibody interaction, IgE epitopes are eliminated with minimal impairment of the residual surface structure important for a non-IgE immunological response.

In another specific embodiment, antibody compositions capable of binding to all epitopes of the Api m 3 polypeptide that are recognized by human IgG antibodies, including IgG4 antibodies, and IgA antibodies are utilized to maintain those structures that mediate an appropriate non IgE response for a long lasting protection after specific immunotherapy (SIT). This rational is based on the recent observation that immune deviation towards T regulatory (Treg) cells is an essential step in successful SIT (for a review, see Jutel et al 2006). Treg cells are defined by their ability to produce high levels of IL-10 and TGF-β and to suppress naive and memory T helper type 1 and 2 responses. There is now clear evidence that IL-10- and/or TGF-β-producing type 1 T regulatory cells are generated in humans during the early course of SIT. Since Treg cells have been shown to differentiate from naive T cells in the periphery upon encountering antigens present at high concentrations, it can be assumed that Treg cells are also induced by high and increasing doses of allergens. Most important is the fact that IL-10 and TGF-β suppress directly or indirectly effector cells of allergic inflammation such as basophils and mast cells, induce the production of non-inflammatory immunoglobulin isotypes (IgG and IgA) and suppress IgE production. Based on these observations, antibody compositions capable of binding to all epitopes of the Api m 3 polypeptide, fragments and analogs thereof that are recognized by human IgG, particularly by human IgG4, and by IgA antibodies are utilized to identify and maintain those amino acid residues involved in the interaction with allergen-specific human IgG and IgA antibodies.

In the context of this invention, the term "epitope recognized by human IgE (IgE epitope), human IgG (IgG epitope), including human IgG4 (IgG4 epitope), or human IgA (IgA epitope)", or relates to the surface area of an allergen that is in contact to these antibodies upon binding to the allergen. It also relates to the surface area of the allergen that is in contact with an antibody construct comprised in the composition of the invention, that overlaps with the first-mentioned IgE epitope, IgG epitope, including IgG4 epitope, or IgA epitope", so binding of the antibody construct can inhibit binding of the human IgE, human IgG, including human IgG4; or human IgA from the sera of patients allergic to the allergen (IgE related epitopes, IgG-related epitopes, IgG4 related epitopes, IgA-related epitopes). Preferably, the epitopes overlap by 20% or more, 50% or more, 60% or more, 70% or more, or 80% or more. Most preferably, the epitopes overlap by 90 or 95% or more or are identical. With reference to the number of epitopes of an allergen, the first-mentioned epitopes and the related epitopes are considered to represent the same epitopes.

For an estimation of the number of antibodies sufficient for binding to all epitopes recognized by human IgE, human IgG (including human IgG4), or human IgA antibodies on the Api m 3 polypeptide, it is important to know the approximate number of possible B cell epitopes per allergen. Therefore, methods for estimating the number of B cell epitopes per allergen have been developed. These methods are based on the following parameters:

a) Calculation of the surface of structurally characterized allergens in $A^2$: The solvent accessible surfaces of proteins can be calculated with the aid of POPS (parameter optimized surfaces) according to Fraternali and Cavallo (2002).

b) Surface area of B-cell epitopes in $A^2$: At the moment, one co-crystallization of allergen and antibody is available only, namely for the allergen Bet v 1 and a murine allergen-specific Fab-fragment. The surface area of this discontinuous epitope is 931 $A^2$ (Mirza et al 2000). This correlates well with the area of other B cell epitopes (circa 2×3 nm).

In Table 5, the surface of allergens for which structural data is available in the protein data bank (PDB) was calculated with the aid of a molecule of water. Under the assumption that a B cell epitope takes up an area of 950 $A^2$, the maximal possible number of B cell epitopes for an allergen (without differentiation for IgE epitopes, IgG epitopes, or IgA epitopes) was determined. The number calculated in this way is much too high, but can be considered to provide an upper limit for the number of necessary antibody constructs for an allergen. On the basis of this data, an approximate relation between molecular weight and potential B cell epitopes was calculated. The mean value of the upper limit for potential B cell epitopes is approx. 0.5 B cell epitopes per 1 kDa.

Table 6 summarizes allergens that have been examined for IgE binding structures with overlapping oligopeptides. Utilizing overlapping oligopeptides (e.g., decapeptides), more potential IgE epitopes are identified than exist in reality, as the majority of IgE epitopes are discontinuous epitopes composed of at least two different areas of the molecule brought together by folding. Different relevant allergens, such as Phospholipase A2 and the birch pollen allergens Bet v1, Bet v3 and Bet v4 exclusively have discontinuous epitopes (Valenta et al 1998). Since the identified linear epitopes probably only form part of these discontinuous epitopes, for estimation of the number of epitopes it is supposed that at least three linear IgE binding epitopes are, as partial structures, involved in forming a discontinuous IgE epitope. Therefore, the number of identified IgE binding peptides has been divided by three and related to the molecular weight of the allergen. A number of 0.06 to 0.19 epitopes per 1 kDa calculated on the basis of linear IgE binding peptides is preferred. The best estimation is possible on the basis of the number of 0.12 IgE epitopes per 1 kDa, which is possibly still too high but could be considered realistic. The preferred compositions correlate well with known data for Bet v 2 (17.4 kDa), which can be bound by three different monoclonal Fab fragments (without differentiating between IgG epitopes, IgE epitopes, or IgA epitopes; Valenta et al 1998). Bet v 2 has at least two IgE epitopes, since it can induce in vivo cross-linking of surface-bound IgE antibodies.

The plurality of Api m 3-specific monoclonal antibodies can be generated from different sources. Naturally occurring IgE antibodies represent ideal tools for structural analyses of IgE epitopes, but their availability is limited. Cloning and selecting allergen-specific IgE antibodies from the immune repertoire of peripheral blood mononuclear cells of allergic donors is extremely difficult. The low number of IgE-secreting B cells in the peripheral blood of allergic patients (MacKenzie and Dosch 1989) seriously hampers this approach for generating monoclonal IgE antibodies. Cloning and selecting Api m 3-specific IgG antibodies, including IgG4 antibodies, or IgA antibodies from the immune repertoire of peripheral mononuclear cells of allergic donors may be less difficult due to the significantly higher number of IgG- or IgA-secreting B cells in the peripheral blood of allergic patients as compared to IgE-secreting B cells. Currently, however, the availability of human monoclonal allergen-specific IgG4 or IgA antibodies is limited.

Semisynthetic or synthetic immunolibraries (e.g., scFv or Fab format) provide a high degree of variability and, thereby, a valuable alternative for generating the required plurality of Ves v 4-specific monoclonal antibody fragments. However, newly generated immunolibraries derived from animals (mammalian species as well as avian species) after immunization with the Api m 3 polypeptide or fragments thereof provide a significantly higher number of Api m 3-specific variable antibody domains and, thereby, an increased probability for the selection of the required plurality of Api m 3-specific high affinity monoclonal antibody fragments. In a preferred embodiment a combination of immunolibraries derived from avian and mammalian species after immunization with the Api m 3 polypeptide or fragments thereof are used. The phylogenetic difference between avian and mammalian species provides access to a different antibody repertoire than the traditional mammalian antibodies. IgY antibodies recognize other epitopes than mammalian antibodies. Therefore, a combination of immunolibraries from avian and mammalian species provides a significant advantage for generating a plurality of Ves v 4-specific high affinity monoclonal antibodies. If it should—unexpectedly—be found that the combination of all antibodies capable of binding to the Api m 3 polypeptide is not sufficient to effect essentially complete inhibition of binding of Api m 3 to antibodies in a pool serum of patients allergic to said allergen or obtained from said sera, it is recommended to additionally use further antibodies from a different library. Methods for generating immunolibraries are known in the art (e.g., Steinberger et al 1996; Edwards et al 2002; Powers et al 2001; Boel et al 2000).

Each antibody composition is obtainable by a method for generating a composition comprising recombinant antibodies, comprising steps of a) Generation a plurality of allergen-specific antibodies capable of binding to the Api m 3 polypeptide, b) combining all generated antibodies and testing whether essentially complete inhibition of binding of the Api m 3 polypeptide to IgE, IgG (including IgG4), and IgA antibodies; in a pool serum of patients allergic to said allergen or obtained from said serum is achieved, c) in case essentially complete inhibition is not achieved in step b), steps a) and b) are repeated;

d) in case essentially complete inhibition is achieved, the number of antibodies is reduced to the minimal number of antibodies sufficient for essentially complete inhibition by a method wherein i) groups of the antibodies obtained in step a) are generated, comprising different numbers and combinations of antibodies;

ii) said groups are tested for essentially complete inhibition of binding of the Api m 3 polypeptide to IgE, IgG (including IgG4), and IgA antibodies, in a pool serum of patients allergic to said allergen or obtained from said sera;

iii) wherein, in case one or more group effects essentially complete inhibition in step ii), steps i) and ii) are repeated with sub-combinations of the antibodies from said group or groups until the minimal number of antibodies in said group or groups is identified which effects essentially complete inhibition;

iv) wherein, in case essentially complete inhibition is not achieved in step ii) or iii), steps i), ii) and iii) are repeated with different groups of antibodies;

and wherein the group identified in step d), iii) is said composition. It is preferred that the composition comprises the minimal number of antibodies necessary and sufficient for binding to all epitopes recognized by human IgE, human IgG (including human IgG4), and human IgA antibodies; on the Api m 3 polypeptide. Additional antibodies may, however, be added.

In the method of the invention, inhibition of binding of the Api m 3 polypeptide to IgE can be determined by incubating IgE antibodies in a pool serum of patients allergic to the Api m 3 polypeptide or antibodies obtained from said serum with human basophils after stripping of said basophils, and with or without preincubation of the Api m 3 polypeptide with the recombinant antibodies or recombinant antibody fragments or, for comparison, antibodies in a pool serum of patients allergic to said allergen or obtained from said serum, contacting said basophils with said allergen, and detecting release of histamine.

Alternatively, inhibition can be determined by contacting anti IgE antibodies immobilized on a carrier with antibodies in a pool serum of patients allergic to the Api m 3 polypeptide or obtained from said serum, and, with or without preincubation of labelled Api m 3 polypeptide with the recombinant antibodies or recombinant antibody fragments or, for comparison, antibodies in a pool serum of patients allergic to said allergen or obtained from said serum, contacting the carrier with said allergen and detecting binding of the labelled Api m 3 polypeptide to the carrier. For this purpose, the Api m 3 polypeptide can be labelled with an enzyme, a radioisotope, biotin or a fluorescent marker.

In the method of the invention, inhibition of binding of the Api m 3 polypeptide to IgG can be determined by contacting anti IgG antibodies immobilized on a carrier with antibodies in a pool serum of patients allergic to the Api m 3 polypeptide or obtained from said serum, and, with or without preincubation of labelled Api m 3 polypeptide with the recombinant antibodies or recombinant antibody fragments or, for comparison, antibodies in a pool serum of patients allergic to said allergen or obtained from said serum, contacting the carrier with said allergen and detecting binding of the labelled Api m 3 polypeptide to the carrier. For this purpose, the Api m 3 polypeptide can be labelled with an enzyme, a radioisotope, biotin or a fluorescent marker.

In the method of the invention, inhibition of binding of the Api m 3 polypeptide to IgG4 can be determined by contacting anti IgG4 antibodies immobilized on a carrier with antibodies in a pool serum of patients allergic to the Api m 3 polypeptide or obtained from said serum, and, with or without preincubation of labelled Api m 3 polypeptide with the recombinant antibodies or recombinant antibody fragments or, for comparison, antibodies in a pool serum of patients allergic to said allergen or obtained from said serum, contacting the carrier with said allergen and detecting binding of the labelled Api m 3 polypeptide to the carrier. For this purpose, the Api m 3 polypeptide can be labelled with an enzyme, a radioisotope, biotin or a fluorescent marker.

In the method of the invention, inhibition of binding of the Api m 3 polypeptide to IgA can be determined by contacting anti IgA antibodies immobilized on a carrier with antibodies in a pool serum of patients allergic to the Api m 3 polypeptide or obtained from said serum, and, with or without preincubation of labelled Api m 3 polypeptide with the recombinant antibodies or recombinant antibody fragments or, for comparison, antibodies in a pool serum of patients allergic to said allergen or obtained from said serum, contacting the carrier with said allergen and detecting binding of the labelled Api m 3 polypeptide to the carrier. For this purpose, the Api m 3 polypeptide can be labelled with an enzyme, a radioisotope, biotin or a fluorescent marker.

The inhibition by recombinant antibodies or recombinant antibody fragments is considered essentially complete if it is comparable to the inhibition by IgE, IgG (including IgG4), or IgA antibodies in a pool serum of patients allergic to the Api m 3 polypeptide or obtained from said serum, i.e. if it varies from that inhibition by 20% or less, preferably by 10% or less, or most preferably, by 5% or less.

The pool serum used in the present invention comprises serum from several patients allergic to the Api m 3 polypeptide. Preferably, said pool serum comprises the antibodies from the sera of at least 5 patients, at least 10 patients or at least 15 patients allergic to said allergen. For IgE inhibition experiments, patients are preferred that are highly sensitized to the allergen. For IgG, IgG4, and IgA inhibition experiments, patients after successful SIT are preferred.

IgE antibodies can be obtained from the pool serum, e.g., by affinity chromatography using anti-human IgE antibodies. Preferably, IgG antibodies are removed from the pool serum, e.g. by pre-treatment with a protein A matrix, such as a protein A column. This step, however, is not essential, as sera of allergic patients in all probability only contain relatively low amounts of allergen-specific IgG antibodies, even though the serum level of IgG is about 10.000 times higher than the serum level of IgE. For example, serum obtained fom a birch pollen allergic patients which was purified by affinity chormatography on immobilized Bet v 1, did not contain significant quantities of allergen specific IgG antibodies (Ganglberger et al 2000). Human IgG4 and human IgA antibodies can also be obtained from the pool serum by affinity chromatography using anti-human IgG4 or anti-human IgA antibodies.

The individual antibodies of a generated composition are used for structural analyses of IgE, IgG (including IgG4), and IgA epitopes. Since each composition effects essentially complete inhibition of binding of the Api m 3-polypeptide to patient-derived IgE, IgG (including IgG4), and IgA antibodies, the individual antibodies of each generated composition are capable of identifying all epitopes on the Api m 3 polypeptide that are accessible for patient-derived IgE, IgG (including IgG4), and IgA antibodies.

According to the present invention the most potent Api m 3-related hypoallergenic molecule for specific immunotherapy is an allergen that does not exhibit allergenicity, contains an array of T cell epitpes that is comparable to that of the corresponding natural allergen, and displays a surface structure that is recognized by human IgG, particularly by human IgG4, and IgA antibodies with specificity for the corresponding natural allergen. For the design of such a molecule, the individual antibodies of the different antibody compositions are essential to maintain IgG epitopes and IgA epitopes upon modification of the IgE epitopes by a structure-based approach.

In specific embodiments, the present invention provides methods for decreasing the allergenicity (IgE reactivity) of the polypeptides of this invention in a structure-based approach via mutagenesis of IgE epitopes with limited impairment of the residual surface structure important for IgG and IgA immunological responses. In a preferred embodiment, the allergenicity of the polypeptides of this invention is reduced by at least 50% while at least 50% of IgG epitopes and IgA epitopes are maintained. In a more preferred embodiment, the allergenicity of the polypeptides of this invention is reduced by at least 70% while at least 50% of IgG epitopes and IgA epitopes are maintained. In a most preferred embodiment allergenicity is reduced by at least 90% while at least 50% of IgG epitopes are maintained.

In the context of this invention, allergenicity is defined as the capability of a proteinaceous allergen to bind human IgE antibodies. Antigenicity in the context of this invention is defined as the capability of a proteinaceous allergen to bind human IgG (including IgG4) and IgA antibodies.

The invention thus also provides a method of treating subjects allergic to the venom of an insect from the order Hymenoptera comprising administering to a subject with such an allergy a protein/polypeptide of the invention.

As used herein, "subject" encompasses human subjects (patients), grown-ups as well as children, and animals.

A pharmaceutical composition comprising a protein of the invention, and, optionally, comprising a suitable adjuvant or expedient, can be employed for this purpose.

The polypeptide of the invention is used for the preparation of a pharmaceutical composition for treating subjects allergic to the venom of an insect from the order Hymenoptera. The invention thus provides a method of treating subjects allergic to the venom of an insect from the order Hymenoptera, comprising administering a polypeptide of the invention to a subject having such an allergy.

Desensitisation approaches are well known in the state of the art. In principle, repeated treatments of allergic individuals with suitable, normally progressively increased doses of allergen diverts the immune response to one dominated by T cells that favour the production of IgG and IgA antibodies over production of IgE antibodies. The IgG and IgA antibodies are thought to desensitise the subject by binding to the small amounts of allergen normally encountered, and preventing the allergen from binding to IgE. Desensitisation to insect or bee venom is almost universally successful (Hunt et al 1978). Different protocols and time schedules can be used, from traditional protocols, rush protocols to ultra-rush protocols (e.g., Schiavino et al 2004), all of which are incorporated herein by reference. The efficacy of such protocols can be evaluated by testing the adjustment of IgE and IgG (different isotypes) and/or IgA levels in the subject's blood or by challenging the subject in a controlled manner and determining the allergic response.

The Api m 3 polypeptide, a fragment, a derivative or an analog thereof is administered over a period of time in gradually increasing doses effective to reduce the allergic response of the individual to the protein allergen. Examples of routes of administration include parenteral (e.g., intravenous), intradermal, subcutaneous, oral (e.g., sublingual or via inhalation), transdermal (topical), and rectal administrations. The effective amount of the Api m 3 polypeptide, a fragment, a derivative and an analog thereof will vary according to factors such as the degree of sensitivity of the individual to Api m 3, the age, sex, and weight of the individual, and the ability of the fragment, derivative, or analog thereof to elicit an antigenic response in the individual. In one embodiment, the amount of Api m 3 polypeptide administered to an individual corresponds to the amount of Api m 3 in the venom of vespids that is injected into an individual by a sting. Dosage regimens may be adjusted to provide the optimum therapeutic response. For example, several divided doses may be administered daily.

The polypeptide of the invention can be administered alone or combination with other allergens, e.g. other Hymenoptera venom proteins or fragments thereof. In particular, combinations with bee or Hymenoptera venom phospholipase A2, hyaluronidase, glucosidase and/or mellitin are suitable, as this therapy induces generation of IgG/IgA antibodies to several venom allergens and can thus lead to full protection. The identified bee allergens are shown in Table 2.

In a specific embodiment, the present invention features a method of modulating an immune response by administering T cell epitope-containing peptides of at least 9 amino acids corresponding to a consecutive amino acid sequence within Api m 3 to a subject in need thereof in an amount sufficient to inhibit an immune reaction by the subject against the Api m 3 polypeptide. If desired, T cell epitope-containing peptides of at least 9 amino acids corresponding to a consecutive amino acid sequence within one or more additional polypeptides, e.g., within a second, third, fourth, or more honeybee venom polypeptide or polypeptides can be comprised in such peptides. The additional honeybee venom polypeptides can include, e.g., the Api m 1 polypeptide (phospholipase A2), the Api m 2 polypeptide (hyaluronidase), the Api m 4 oligopeptide (mellitin), the Api m 5 polypeptide, (allergen C, dipeptidylpeptidase), and other glycosylated or non-glycosylated IgE-binding honeybee venom proteins, or analogs or derivatives thereof.

As used herein, a decrease or modification of the T cell response of a mammal sensitive to a protein allergen is defined as non-responsiveness or diminution in symptoms to the protein allergen in the mammal, as determined by standard clinical procedures (see e.g., Varney et al 1991). As referred to herein, a diminution in symptoms to an allergen includes any reduction in the allergic response of a mammal (such as a human) to the allergen following a treatment regimen with a polypeptide as described herein. This diminution in symptoms may be determined subjectively in humans (e.g., the patient feels more comfortable upon exposure to the allergen), or clinically, such as with a standard skin test.

The polypeptide of the invention can also be used for the preparation of a diagnostical composition for diagnosing or identifying subjects allergic to the venom of an insect from the order Hymenoptera. A method of diagnosing an allergy to venom of an insect from the order Hymenoptera is thus provided, comprising the steps of a) contacting a subject with a polypeptide of the invention and b) detecting an allergic reaction, wherein detecting an allergic reaction indicates said allergy.

In vivo tests for diagnosis of an allergy can easily be adapted to the polypeptide of the invention. Typically, a suitable amount of allergen is injected subcutaneously into a subject's limb, and, after a certain amount of time, the degree of localised inflammation in comparison to controls is determined (skin prick test). Such tests are well known in the art (Hamilton 2002, Poulsen 2001, Schmid-Grendelmeier 2001, Williams et al 1999, Barbee et al 1976).

An allergy to the venom of an insect from the order Hymenoptera can also be diagnosed by an in vitro method comprising the steps of
- a) in vitro contacting a blood sample from a subject with a polypeptide of the invention and
- b) detecting binding of IgE antibodies to the polypeptide, wherein detecting IgE antibodies binding to the polypeptide indicates said allergy.

Binding of IgE antibodies to the polypeptide can, e.g., be detected in an ELISA or by an in vitro release assay employing stripped mast cells and measuring the amount of released mediator, e.g., histamine. To determine specific binding, the results are compared with a specificity control, e.g., with an unrelated antibody. The diagnostic tests can in parallel be carried out to determine the levels of specific IgG (in particular IgG1 and/or IgG4) and/or IgA. For this, an ELISA with specific secondary antibodies recognising the different isotypes can be employed. Parallel testing is particularly useful for following and evaluating a course of specific immunotherapy.

In another embodiment, the present invention provides in vitro diagnostic assays on peripheral blood lymphocytes useful for obtaining information on Api m 3-specific T cell responses, the phenotype of the T cell response, and preferably the T cell epitope(s) of Api m 3 involved in T cell responses. The immunodominant epitope(s) and the epitope(s) involved in IgE isotype class switch events can be detected, if they are not identical. In particular, the T cell epitope(s) of Api m 3 that stimulate proliferation and/or lymphokine secretion of T cells of a phenotype associated with IgE isotype class switching events can be identified for a specific individual, or for a class of individuals who share MHC haplotype or a predominant T cell receptor variable region expression, or both.

For the therapeutic and diagnostic uses and methods, it is preferred to employ the fusion polypeptides of the invention, non-glycosylated proteins or polypeptides that are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to a polypeptide selected from the group consisting of amino acid 26 to 99, 116 to 145, 153 to 158, 185 to 223, 232 to 276 or 362 to 373 of the polypeptide shown in SEQ ID NO: 2. Alternatively, the employed polypeptides are capable of binding to IgE from subjects allergic to venom of an insect from the order Hymenoptera, and comprise at least 5, preferably at least 6, 7, 8, 9, 10, 15, 20 or more amino acids of a polypeptide more than 70%, more than 80% or more than 90% homologous or identical to the polypeptide shown in SEQ ID NO: 2, except for the polypeptides from the group consisting of amino acids 1 to 34, 63 to 80, 100 to 115, 142 to 149, 168 to 176, 224-239 and 258 to 343 of the polypeptide shown in SEQ ID NO: 2 or except for the polypeptides shown in FIG. 5. Additionally, such polypeptides consisting of amino acids 1 to 25, 146 to 152, 159 to 164, 168 to 184, 224 to 231, and 277 to 361 can be used.

In one embodiment, the Api m 3 polypeptide, fragments, derivatives and/or analogs thereof, are incorporated into pharmaceutical compositions suitable for administration. Such compositions typically comprise the Api m 3 polypeptide, fragments, derivatives or analogs thereof, and a pharmaceutically acceptable carrier. As used herein, a 'pharmaceutically acceptable carrier' is intended to include any and all solvents, dispersion media, coatings, antibacterial and antifungal agents, isotonic and adsorption delaying systems, and the like, compatible with the active compound and pharmaceutical administration. The use of such media and agents for pharmaceutically active substances is well known in the art. Supplementary active compounds can also be incorporated into the composition. As used herein, the phrases 'pharmaceutical composition' and 'medicament' are interchangeable.

In another embodiment, the pharmaceutical composition includes an additional polypeptide, e.g., a second, third, fourth, or more honeybee venom polypeptide or polypeptides. The additional honeybee venom polypeptides can include, e.g., the Api m 1 polypeptide (phospholipase A2), the Api m 2 polypeptide (hyaluronidase), the Api m 4 oligopeptide (mellitin), the Api m 5 polypeptide, (allergen C, dipeptidylpeptidase), and other glycosylated or non-glycosylated IgE-binding honeybee venom proteins, or analogs or derivatives thereof.

In another embodiment, the present invention features a pharmaceutical composition comprising Api m 3 polypeptide fragments of the invention, preferably between 20-150 amino acids in length, wherein each fragment contains one or more B cell epitopes and one or more T cell epitopes, and a pharmaceutically acceptable carrier.

In another embodiment, the pharmaceutical composition includes polypeptide fragments derived from an additional polypeptide, e.g., a second, third, fourth, or more honeybee venom polypeptides or oligopeptides including, but not limited to, the Api m 1 polypeptide (phospholipase A2), the Api m 2 polypeptide (hyaluronidase), the Api m 4 oligopeptide (mellitin), the Api m 5 polypeptide, (allergen C, dipeptidylpeptidase), and other glycosylated or non-glycosylated IgE-binding honeybee venom proteins, or analogs or derivatives thereof.

In another embodiment, the pharmaceutical composition includes Api m 3 polypeptide fragments of the invention, fused to polypeptide fragments derived from an additional polypeptide, e.g., a second, third, fourth, or more honeybee venom polypeptides or oligopeptides including, but not limited to, the Api m 1 polypeptide (phospholipase A2), the Api m 2 polypeptide (hyaluronidase), the Api m 4 oligopeptide (mellitin), the Api m 5 polypeptide, (allergen C, dipeptidylpeptidase), and other glycosylated or non-glycosylated IgE-binding honeybee venom proteins, or analogs or derivatives thereof.

In another embodiment, the present invention features a pharmaceutical composition comprising T cell epitope containing peptides of at least 9 amino acids corresponding to a consecutive amino acid sequence within Api m 3 wherein the peptides are capable of stimulating T cells of subjects allergic to Api m 3. In a preferred embodiment, the composition comprises a set of T cell epitope-containing peptides capable of stimulating T cells of the great majority of subjects allergic to Api m 3.

In another embodiment, the pharmaceutical composition includes T cell epitope-containing peptides of at least 9 amino acids corresponding to a consecutive amino acid sequence within an additional polypeptide, e.g., a second, third, fourth, or more honeybee venom polypeptides or oligopeptides including, but not limited to, the Api m 1 polypeptide (phospholipase A2), the Api m 2 polypeptide (hyaluronidase), the Api m 4 oligopeptide (mellitin), the Api m 5 polypeptide, (allergen C, dipeptidylpeptidase), and other glycosylated or non-glycosylated IgE-binding honeybee venom proteins, or analogs or derivatives thereof.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents, antioxidants such as ascorbic acid or sodium bisulfate, chelating agents such as ethylenediaminetetraacetic acid, buffers such as acetates, citrates or phosphates and agents for the adjustment of toxicity such as sodium chloride or dextrose. The pH can be adjusted with acids or bases, such as hydrochloric acid or sodium hydroxide. In many cases, it will be preferable to include isotonic agents, for example, sugars, polyalcohols such as mannitol, sorbitol, sodium chloride in the composition. The composition should be fluid to the extent that easy syringability exists. The proper fluidity can be maintained, for example, by the use of a coating such as lecithin, by the maintenance of the required particle size in the case dispersion and by use of surfactants. The composition should be stable under the conditions of manufacture and storage and should be preserved against the contaminating action of microorganisms such as bacteria and fungi. Prevention of the action of microorganisms can be achieved by various antibacterial and antifungal agents such as parabens, chlorobutanol, phenol, ascorbic acid, thimoseral, and the like. Delayed absorption of the injectable compositions can be achieved by including in the composition an agent such as aluminium monostearate and gelatin. In all cases, the composition must be sterile. Sterile injectable solutions can be prepared by filtered sterilization. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The parenteral preparation can be enclosed in ampoules, disposable syringes or multiple dose vials made of glass or plastic.

Oral compositions generally include an inert diluent or an edible carrier. They can be enclosed in gelatine capsules or compressed into tablets. For the purpose of oral therapeutic administration, the active compound can be incorporated with excipients and used in the form of tablets, troches, or capsules. Oral compositions can also be prepared using a fluid carrier for use as mouthwash, wherein the active compound in the fluid carrier is swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatine; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavouring agent such as peppermint, methyl salicylate, or orange flavouring.

For administration by inhalation, the active compounds are delivered in the form of an aerosol spray from a pressured container or dispenser which contains a suitable propellant, e.g. a gas such as carbon dioxide, or a nebulizer.

For transmucosal or transdermal administration, penetrants appropriate to the barrier to be permeated are used in the formulation. Such penetrants are generally known in the art, and include for transmucosal administration, for example; detergents, bile salts, and fusidic acid derivatives. Transmucosal administration can be accomplished through the use of nasal sprays or suppositories. Suppositories can be prepared using conventional suppository base such as cocoa butter or other glycerides. For transdermal administration, the active compounds are formulated into ointments, salves, gels, or creams as generally known in the art. For rectal delivery the compounds can also be prepared in the form of retention enemas.

In a further embodiment, the active compounds are prepared with carriers that will protect the active compounds against rapid elimination from the body, such as controlled release formulation, including implants and microencapsulated delivery systems. Biodegradable, biocompatible polymers can be used, such as ethylene vinyl acetate, polyanhydrides, polyglycolic acid, collagen, polyorthoesters, and polyacetic acid. Methods for preparation of such formulations will be apparent to those skilled in the art. The materials can also be obtained commercially. Liposomal suspensions can also be used as pharmaceutically acceptable carriers. These can be prepared according to methods known to those skilled in the art.

For oral and parenteral applications it is advantageous to formulate the compositions in dosage unit form for ease of administration and uniformity of dosage. Dosage unit form as used herein refers to physically discrete units suited as unitary dosages for the subject to be treated. Each unit contains a predetermined quantity of the active compound calculated to produce the desired therapeutic effect in association with the included pharmaceutical carrier. The specification for the dosage unit forms of the invention are dependent on the unique characteristics of the active compound and the particular therapeutic effect to be achieved, and the limitations inherent in the art of compounding such an active compound for the treatment of individuals. The pharmaceutical compositions can be included in a container, pack, or dispenser together with instructions for administration.

The present invention also relates to a method of diagnosing an allergy to venom of an insect from the order Hymenoptera, comprising the steps of
  a) performing the method of producing a polypeptide encoded by the nucleic acid of the invention, wherein the host cell comprising the expression vector of the invention is cultured under appropriate conditions for expression of said polypeptide, and wherein said polypeptide is purified,
  b) contacting the polypeptide obtained by the method of step a) in vitro with a blood sample,
  c) and detecting binding of IgE antibodies to the polypeptide, wherein detecting IgE antibodies binding to the polypeptide indicates said allergy.

Furthermore, a method of diagnosing an allergy to venom of an insect from the order Hymenoptera is provided, comprising the steps of
  a) performing the method of producing a polypeptide encoded by the nucleic acid of the invention, wherein the host cell comprising the expression vector of the invention is cultured under appropriate conditions for expression of said polypeptide, and wherein said polypeptide is purified,
  b) contacting a subject with the polypeptide obtained by the method of step a) and detecting an allergic reaction, and
  c) detecting an allergic reaction, which is indicative of the allergy.

The invention also provides a method of preparing a composition for diagnosing an allergy to venom of an insect from the order Hymenoptera comprising the step of producing a polypeptide encoded by the nucleic acid of the invention, wherein the host cell comprising the expression vector of the invention is cultured under appropriate conditions for expression of said polypeptide and said polypeptide is purified and can be used as such for diagnosis. Optionally, the polypeptide is further formulated with stabilizers, such as a neutral protein (e.g., BSA) or detergents to give said composition.

In another embodiment, the invention teaches a method of preparing a composition for treating subjects allergic to the venom of an insect from the order Hymenoptera, comprising the step of performing the method of producing a polypeptide encoded by the nucleic acid of the invention, wherein the host cell comprising the expression vector of the invention is cultured under appropriate conditions for expression of said polypeptide and said polypeptide is purified and can be used as such for therapy. Optionally, the polypeptide is further formulated with appropriate excipient and/or carriers in order to provide said composition. Correspondingly, a method of treating subjects allergic to the venom of an insect from the order Hymenoptera is disclosed, comprising the steps of a) performing the method of producing a polypeptide encoded by the nucleic acid of the invention, wherein the host cell comprising the expression vector of the invention is cultured under appropriate conditions for expression of said polypeptide and said polypeptide is purified, and b) administering the polypeptide obtained by the method of step a) to a subject having such an allergy.

The present invention thus for the first time satisfies the need for a recombinantly produced Hymenoptera venom acid phosphatase or the cDNA encoding this polypeptide, which can be used for diagnostic and therapeutic applications.

EXAMPLES

Example 1

Cloning of cDNA 1.1 Total RNA Isolation

Total RNA was isolated from the separated stinger of a honey bee with attached venom sack and additional glands. The isolation of total RNA was performed using a kit according to the manual (peqGold TriFast™, peqlab Biotechnologie GmbH, Erlangen, Germany) The organ was weighed and homogenised in a solution containing guanidiniumisothiocyanate and phenol. Phase separation was induced by addition of chloroform. The aqueous phase was separated after centrifugation, and the containing RNA precipitated with isopropyl alcohol. After washing with diluted ethanol the RNA was dissolved in RNase-free sterile water and used directly in RT-PCR experiments. To prepare RNase-free sterile water cell-culture suitable water was treated with 0.1% (v/v) diethylpyrocarbonate (DEPC) overnight, and then autoclaved for 20 minutes to destroy DEPC by causing hydrolysis of DEPC.

1.2 cDNA First Strand Synthesis

Reverse transcriptase was used to synthesise first strand cDNA from the isolated RNA. For this 5 µl of total bee RNA was mixed with 2 µl (20 pmol) oligonucleotide primer and 4 µl DEPC water. An universal oligo-dT of 20 base pair length was used for the purpose of transcribing the polyadenylated portion of mRNA in the total RNA sample. The reaction mix was incubated at 70° C. for 5 minutes to break secondary structures. After this, the reaction was chilled on ice. Subsequently, 1.5 µl DEPC water, 4 µl 5× reaction buffer, 2 µl dNTP mix (10 mM), and 0.5 µl RNaseOut™ recombinant ribonuclease inhibitor (Invitrogen GmbH, Karlsruhe, Germany) were added. The reaction mix was incubated at 37° C. for 5 minutes. Then 1 µl (200 units) RevertAid™ M-MuLV Reverse Transcriptase (RT, Fermentas GmbH, St. Leon-Rot, Germany) was added and the reaction was incubated at 42° C. for 60 minutes. After this the reaction was stopped by heating to 70° C. for 10 minutes and chilled on ice.

1.3 RT-PCR

First strand cDNA from bee venom gland tissue was used as template for PCR amplification of Api m3 DNA sequences.

Known peptide fragments, public databases and bioinformatics were used to design the specific primers for Api m3. These primers have been designed to allow 5'-end blunt subcloning for native N-terminal expression and 3'-end directed Sac II restriction site subcloning. The nucleotide sequences of the oligonucleotides are:

```
Api m3 for, 21 mer, blunt end (SEQ ID NO: 3):
5'-GAA CTT AAA CAA ATA AAT GTG Api m3 back 32 mer, Sac II site (SEQ ID NO: 4):
5'-AAC CGC GGT TAC TTA CTT ATT CTC AGT ACC CG.
```

The PCR reaction contained 41 µl DEPC water, 5 µl 10× complete Pfu PCR buffer, 1 µl Api m3 for primer (100 pmol), 1 µl Api m3 back primer (100 pmol), 1 µl dNTP mix (10 mM), 0.5 µl bee venom gland tissue cDNA, and 0.5 µl recombinant Pfu DNA polymerase (Fermentas GmbH, St. Leon-Rot, Germany), to give a total reaction volume of 50 µl.

The PCR temperature program for amplification was:
Step 1: 96° C., 1 minute
Step 2: 95° C., 30 seconds
Step 3: 55° C., 30 seconds
Step 4: 72° C., 2 minutes
Repeat steps 2-4×29 times
Step 5: 72° C., 10 minutes
Step 6: 4° C., until end Part of the PCR reaction was run on a 1% agarose (peqGOLD universal agarose, peqlab GmbH, Erlangen, Germany) gel in 0.5×TAE buffer and amplified DNA products visualised with ethidium bromide and UV illumination. A band at the expected size was visible.

1.4 Subcloning for Sequencing

DNA from the PCR reaction was isolated using the QIAEX II gel extraction kit (Qiagen GmbH, Hilden, Germany). Subcloning for sequencing was done using the TOPO TA Cloning® Kit (Invitrogen GmbH, Karlsruhe, Germany) with pCR®2.1-TOPO® vector according to the manual. Due to use of Pfu DNA polymerase an initial TA-elongation reaction step with AGS Gold Taq DNA Polymerase (AGS Hybaid, Heidelberg) was introduced. The ligated DNA was transformed into E. coli of the strain TG1 by electroporation (2 mm cuvettes, EasyJect+, Hybaid, Heidelberg, Germany) and selected on ampicillin agar plates.

1.5 Sequencing

The sequencing reaction was done with BigDye® Terminator Cycle Sequencing Kit from ABI (Applied Biosystems Applera Deutschland GmbH, Darmstadt, Germany) according to the manual. 25 cycles were run with a 30 seconds denaturation step at 96° C., 15 seconds annealing step at 50° C., and 4 minutes elongation step at 57° C. Sequencing primer were:

```
M13/Uni for (SEQ ID NO: 5):
5'-GTA AAA CGA CGG CCA GTG CCA A

M13/Uni rev (SEQ ID NO: 6):
5'-CAG GAA ACA GCT ATG ACC ATG A
```

The resulting sequence is shown in FIG. 1.

Example 2

Construction of Expression Vector 2.1 Modification of the Insect Expression Vector For expression of recombinant Api m 3 with potential for native folding and posttranslational modification, the expression in insect cells was chosen. The expression vector pIB/V5-His. (Invitrogen GmbH, Karlsruhe, Germany) was modified to facilitate isolation and purification. A melittin signal sequence for secretion of the recombinant protein was added and the Kozak sequence was optimised for higher expression rates in insect cells. The melittin signal sequence was amplified from total bee RNA, synthesised as described above, using the primers:

```
melt leader for (SEQ ID NO: 7):
5'-GGA AAG CTT TCC GCC ATG GCG AAA TTC TTA GTC melt leader back (SEQ ID NO: 8):
5'-CGG GAT CCC GCA TAG ATG TAA GAA ATG.
```

Underlined are the Hind III and, respectively, BamH I restriction sites in the corresponding primer. The sequence containing the 10× histidine-tag and factor Xa cleavage site has been cloned between the BamH I and EcoR V site of the parent vector. As first template, a tag containing vector was used with the following primers:

```
10xHis for (SEQ ID NO: 9):
5'-CTG AAT AGC GCC GGA TCC GAC CAT

10xHis back (SEQ ID NO: 10):
5'-CCC TCT AGA CTC GAG CCA ATG ATG
```

Underlined are the bases for the introduction of the BamH I restriction site. The resulting fragment was used as second template and further modified to contain a EcoR V site at the 3'-end by use of overlapping primers and PCR extension of the sequence (splice-overlap-extension, SOE). The extension primer used was:

```
SOE Xa (SEQ ID NO: 11):
5'-GGG ATA TCC CTT CCC TCG ATC CCT CTA GAC TC
```

Underlined is the newly introduced EcoR V restriction site for cloning and generation of the expression vector construct. For all PCR steps Pfu DNA polymerase (Fermentas GmbH, St. Leon-Rot, Germany) was used with standard reaction conditions. The annealing temperature was 55° C. for the 10× Histidin fragment amplification and 45° C. for the SOE reaction.

2.2 Re-PCR and Subcloning

After sequencing of selected subcloned cDNA clones and verification of the sequence, the clone was used for secondary amplification with Pfu DNA polymerase. The PCR product was subcloned into the EcoR V/Sac II digested expression vector after restriction digest with Sac II.

2.3 Modification of the Bacterial Expression Vector

The verified mammalian expression vector pIB/Mel opt-H10 was used as template for the construction of insert for subcloning into the prokaryontic expression vector pET26 (+) (Novagen). The PCR program was done according to the temperature gradient given in 1.3. Pfu polymerase was used with the primers:

```
                                         (SEQ ID NO: 12)
Api 3 for pro-his    AGAATTTCATATGAAATTCTTAGTCAACG (SEQ ID NO: 13)
Api 3 back pro       AAGAGCTCTTACTTACTTATTCTCAG
```

The amplicon was digested with Sac I and Nde I. The partly digested fragment of correct size was isolated and ligated into the pre-digested vector.

Example 3

Expression of Recombinant Protein 3.1 Transfection

HighFive insect cell (Invitrogen GmbH, Karlsruhe, Germany) were used as hosts for the recombinant expression of Api m 3. DNA was purified from bacterial cultures using the E.Z.N.A. Plasmid Miniprep Kit II (peqlab GmbH, Erlangen, Germany) according to the manual. For transfection of purified DNA into cells the reagent Cellfectin® (Invitrogen GmbH, Karlsruhe, Germany) was used according to the manual.

3.2 Transformation

Vectors have been transformed into prokaryontic cell by electroporation. Cells have been prepared by standard procedures. Electroporation was done with an EasyJecT+ instrument (EquiBio, Maidstone, UK) with standard settings according to the manual of the manufacturer.

3.3 Isolation of Recombinant Protein

The protein was purified according to standard procedures.

In brief, prokaryotic cells were disrupted by sonication. Cell membranes etc. were sedimented by ultracentrifugation. The His-tagged protein was then purified from the extract by $Ni^{2T}$ affinity chromatography following the manufacturer's recommendations (e.g., His Trap™ HP Kit, Amersham Biosciences). Purification was controlled by SDS-PAGE. In the case of eukaryotic expression the supernatant medium was collected from confluent stably transfected insect cell expression cultures. The supernatant was adjusted to pH 7.8 and centrifuged at 4000×g for 5 minutes. Aliquots of 10-20 ml medium were applied to a nickel-chelating affinity matrix (NTA-agarose, Qiagen). The column was washed with 10 ml NTA-binding buffer (50 mM sodium phosphate, pH 7.6, 500 mM NaCl) and pre-eluted with NTA-binding buffer containing 20 mM imidazole. The recombinant protein was finally eluted from the matrix with 10 ml NTA-binding buffer containing 400 mM imidazole. Purification was controlled by SDS-PAGE and silver staining of protein.

Example 4

Analysis of Recombinant Api m 3

4.1 Sequence Alignment and Motif Analysis

Sequence databases were screened with BLAST algorithms for related sequences of the cloned Api m 3 in other organisms. Sequence alignment was performed with four homologous sequences found in the organisms *Drosophila melanogaster* and *Drosophila subobscura* coding for acid phosphatases. The sequences show significant homologies. The highest homology with 35% is found for Acph-1 from *D. melanogaster* Amino acids necessary for acid phosphatase activity (RHGXRXP motif) are highly conserved in the sequence. In addition, four potential N-glycosylation sites (NXS/T motif) have been identified.

4.2 Tryptic Fragment Prediction

To verify the cloned sequence matches the expressed recombinant protein a prediction of tryptic fragments was done based on the nucleic acid sequence. The purified protein was digested with sequence grade Trypsin (Sigma-Aldrich Chemie GmbH, Taufkirchen, Germany) according to the instructions of the manufacturer and the resulting peptide fragments were analysed by MALDI-TOF spectrometry using standard protocols. The predicted fragments matched the data acquired by MALDI-TOF and therefore verified the identity of the recombinant protein.

4.3 Enzymatic Activity Assay

Enzymatic activity of the recombinant enzyme was confirmed according to a described method (Barboni et al 1987).

Example 5

Immunoreactivity of Recombinant Api m 3

Recombinant Api m 3 isolated from stably transfected insect cells was used in an immunoprinting experiment with serum from honey bee venom allergic patients to evaluate IgE reactivity. Diluted honey bee venom and purified recombinant Api m 3 were examined in the same experiment. Proteins were separated on 10% SDS-PAGE gels under reducing conditions. Transfer to nitrocellulose membrane (Protran, Schleicher & Schuell BioScience GmbH, Dassel, Germany) and subsequent immunostaining for sIgE reactive allergens was done using a kit according to the manual (AlaBLOT kit, DPC Biermann GmbH, Bad Nauheim, Germany) showing the immunoreactivity of recombinant Api m 3.

Example 6

Patient Screening with Recombinant Api m 3

Immunoreactivity Assays with Sera from Individual Patients

Figure 6:
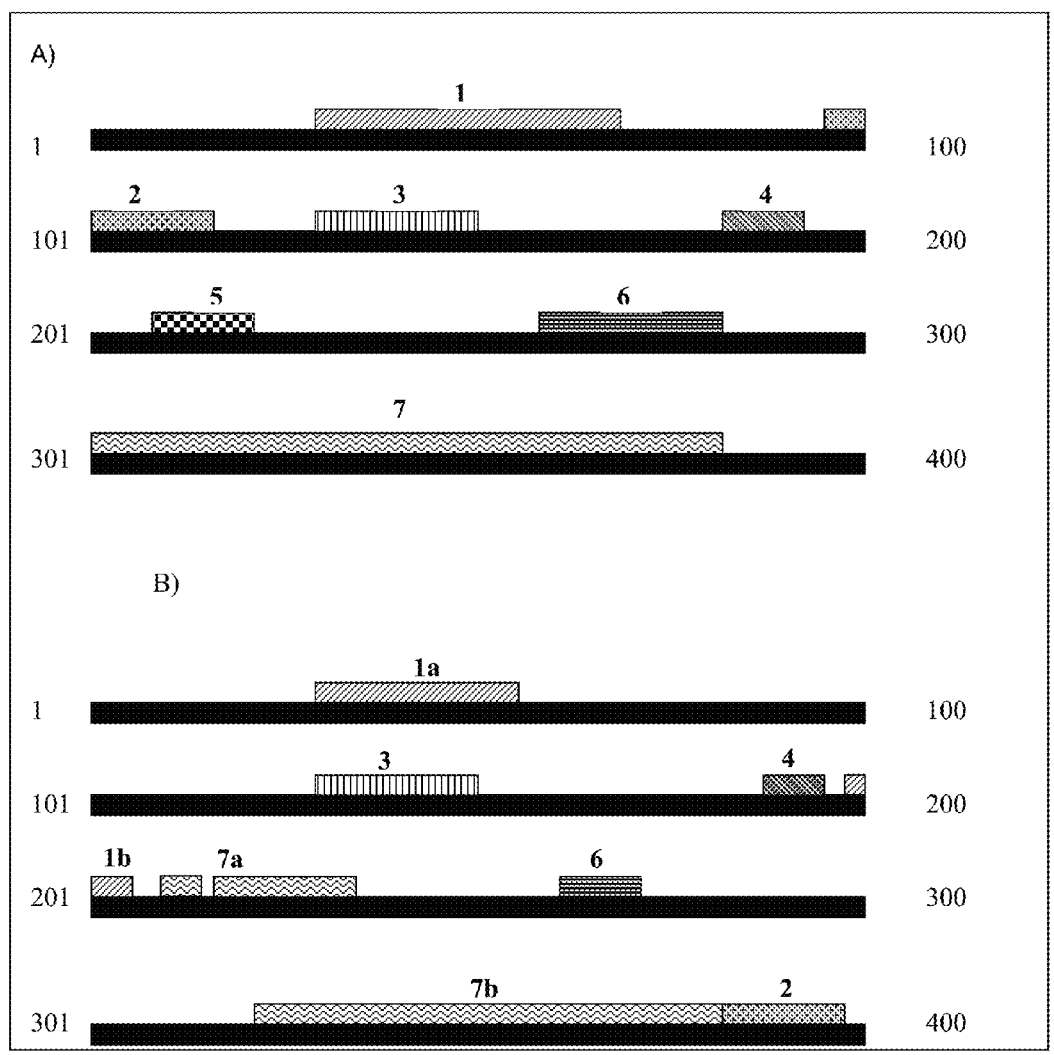
FIG. 6 shows a schematic alignment of peptides postulated by Hoffman et al. (1996) (A), in comparison to the corrected order after cloning and sequencing of the Api m 3 gene (B). It is obvious that the alignment differs from the published alignment with human and rat prostate phosphatase (Hoffman 1996). The published peptide fragments can not be aligned to match the sequence as would be expected. Firstly, the order of alignment positions is different from the publication. Secondly, some fragments, like fragments 1 and 7 partially align at different sites in the sequence, and therefore are not continuous peptides derived from a cDNA sequence. Furthermore, some published fragment sequences, like fragment 5, cannot be aligned at all. The scheme also shows the leader peptide and is not exact regarding the number of amino acids.
Figure 7:
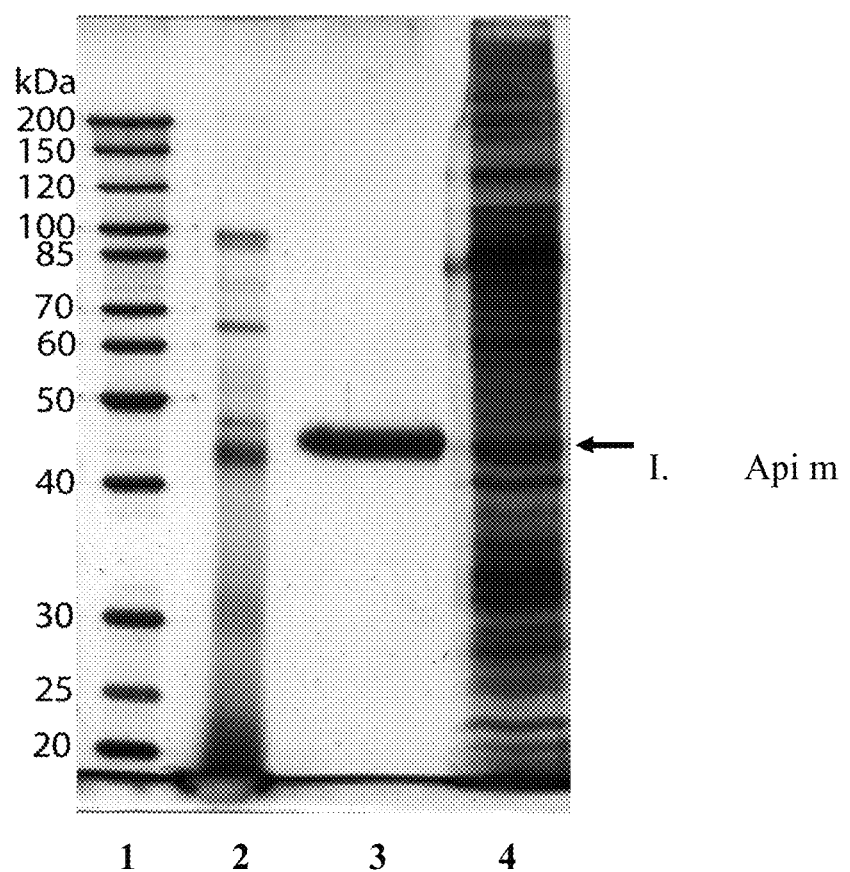
FIG. 7 depicts recombinant Api m 3 expression and purification. Shown is a 10% silver stained SDS-PAGE gel. Lane 1, protein molecular weight standards; lane 2, diluted bee venom; lane 3, purified recombinant Api m 3 derived from insect cell expression; lane 4, supernatant from cells stably transfected with recombinant Api m 3.
Figures 9, 10:
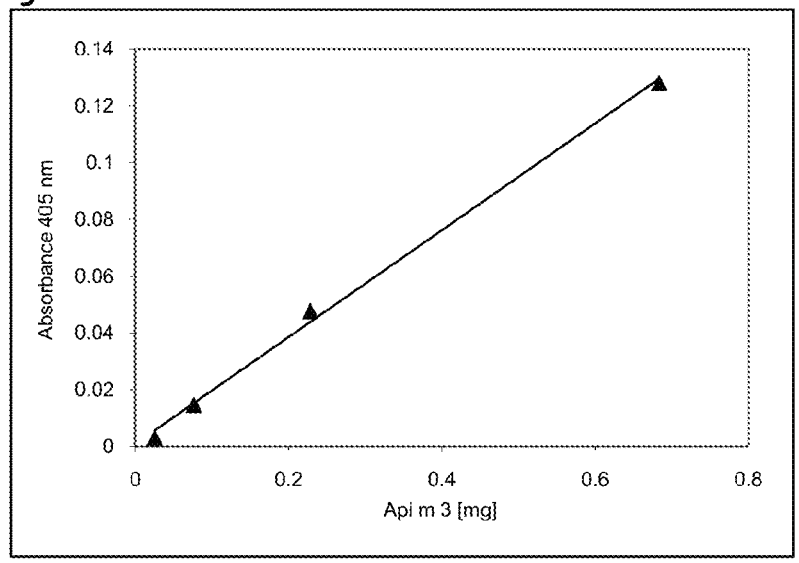
FIG. 9 Results from MALDI-TOF spectrometry in comparison with predicted tryptic fragments. Experimental data are in accordance with the prediction.
FIG. 10 shows the enzymatic activity of purified recombinant Api m 3. Shown is the acid phosphatase enzymatic activity of recombinant Api m 3 dependent on the amount of protein used. The experiment was performed according to Barboni et al (1987).

To detect specific IgE immunoreactivity of human sera with purified recombinant Api m 3, ELISA plates (NUNC GmbH & Co. KG, Wiesbaden, Germany) were coated with 100 µl of purified recombinant Api m 3 (1 µg/ml) or, as a positive control, purified natural Api m 1 (1 µg/ml) (Latoxan, Valence, France) at 4° C. overnight. For all reaction steps, an ELISA buffer reagent set was used according to the manual (BD Biosciences, Heidelberg, Germany). Appropriate dilutions (1:2; 1:5; 1:10) of the sera were made in assay diluent. Bound IgE was detected with a biotinylated mouse anti-human IgE (BD Biosciences) together with horseradish peroxidase-conjugated avidin, both diluted 1:250 in assay diluent. Color was developed with 100 µl substrate solution per well for 30 minutes in the dark. Finally, 50 µl stop solution were added and plates were read at 450/570 nm. For quality control of the assay, an 8-point human IgE standard curve was run on each plate using murine anti-IgE (10 µg/ml) as capture antibody and human myeloma IgE (Calbiochem-Merck, Darmstadt, Germany) over a concentration range of 31.25 to 4,000 pg/ml (100 µl per well, diluted in assay diluent). Secondary antibody and detection system for total IgE were identical to the one described above for the detection of Api m 1/rApi m 3 sIgE. It could be shown that approximately 37.5% (15/40) of the patient sera that were characterized by a positive sIgE test to honeybee venom had detectable sIgE to recombinant Api m 3. Of 19 patients lacking serologic reactivity to honeybee venom (sIgE <0.35 kU/L), 10 patients were highly sensitized to *Vespula* spp. venom but non-reactive towards honeybee venom (sIgE >50 kU/L, FIG. 6B) and 9 were individuals lacking serologic IgE reactivity to both hymenoptera venoms (sIgE <0.35 kU/L to both, vespid and honeybee venom). Only one serum out of the 19 sera lacking serologic reactivity to honeybee venom showed reactivity with recombinant Api m 3. This patient had a clearcut positive sIgE result in the recombinant Api m 3 ELISA. He reported to the allergy service with a history of a severe anaphylactic reaction after a hymenoptera sting. The offending insect was not identified by the patient. Despite a negative "classical" serologic result and a negative intradermal skin test, the patient was finally classified as an honey bee venom allergic patient. It can be assumed that he reacts strongly to native Api m 3 with is likely to be underrepresented in clinical test kits and therefore his allergy was not noticed.

Example 7

Figure 13:
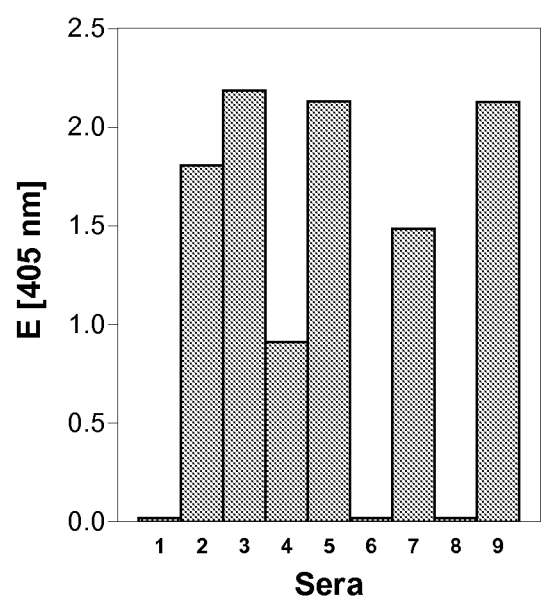
FIG. 13 shows the detection of native Api m 3 with IgE from sera of honeybee venom-allergic individuals. Experimental conditions are described in Example 7. Shown are data after subtraction of background values.

Improved differentiation between sera binding to different epitopes based on recombinantly expressed Api m 3 a) Api m3 Expressed in Bacterial Cells:

The different structural features of recombinant Api m 3 expressed in bacterial cells are documented by following experiments (experimental conditions as described in Example 6):

As shown in FIG. 13, native Api m 3 purified according to document D1 is recognized by IgE in 6 of 9 (66%) sera from patients with honeybee venom allergy. This result is in excellent accordance with data published by Kemeny et al. (1983). Using purified native Api m 3, Kemeney and coworkers demonstrated serum IgE to Api m 3 in 60% of the sera from patients with honeybee venom allergy.

In contrast, recombinant Api m 3 expressed in bacterial cells (*E. coli*) is recognized by IgE in a significantly lower number of sera from patients with honeybee venom allergy. When expressed as fusion protein with bacterial maltose bindin protein (MBP), Api m 3 is recognized by IgE in 3 of 9 (33%) sera from patients with honeybee venom allergy (see FIG. 14A). When expressed as fusion protein with eukaryotic glutathion-S-transferase (GST), Api m 3 is recognized by IgE in only 2 of 9 (22%) sera from patients with honeybee venom allergy (see FIG. 14B).

b) Api m3 Expressed in Insect Cells:

Recombinant Api m 3 molecules expressed in insect cells (HighFive cells or SF9 cells) are glycosylated, but the glycosylation pattern provided by both insect cell lines to Api m 3, exhibits significant differences. As a result, both Api m 3 molecules are recognized by IgE in different sera from patients with honeybee venom allergy.

The profound effects of different glycosylation patterns of Api m 3 expressed in different insect cells, on the binding of IgE antibodies are documented by following experiments:

Api m 3 expressed in HighFive insect cells is recognized by IgE in 6 of 9 (66%) sera from patients with honeybee venom allergy and, however, partly by different sera than native Api m 3 (see FIG. 15A). Api m 3 expressed in SF9 insect cells is recognized by IgE in only 3 of 9 (33%) sera from patients with honeybee venom allergy (see FIG. 15B).

Furthermore, FIG. 16 demonstrates that both molecules are recognized to a different extent by IgE in sera from patients allergic to both honeybee and wasp venom, which allows for an improved evaluation of carbohydrate based cross-reactivity of IgE antibodies. The data in FIG. 16 show that recombinant Api m 3 produced in HighFive insect cells is recognized by IgE in 19 of 23 (82%) sera from patients allergic to both honeybee and wasp venom. Ten of these sera contain IgE that is highly reactive with Api m 3 produced in HighFive insect cells. It should be stressed that the sera tested in FIG. 16 are obtained from patients allergic to both honeybee and wasp venom and, therefore, cannot be compared to those sera tested in FIG. 13-15 which are obtained from patients allergic only to honeybee venom.

In summary, the structural features of recombinant Api m 3 expressed in *E. coli* and insect cells differ significantly from those of native Api m 3.

REFERENCES

Arbesman C E, Reisman R E, Wypych J I. Allergenic potency of bee antigens measured by RAST inhibition, Clin. Allergy 6, 587-94 (1976).

Barbee R A, Lebowitz M D, Thompson H C, Burrows B Immediate Skin-Test Reactivity in a General Population Sample, Ann. Int. Med. 84, 129-133 (1976).

Barboni E, Kemeny D M, Campos S, Vernon C A, The purification of acid phosphatase from honey bee venom (*Apis mellifica*), Toxicon 25(10), 1097-103 (1987).

Bauer L. et al. Modulation of the allergenic immune response in BALB/c mice by subcutaneous injection of high doses of the dominant T cell epitope from the major birch pollen allergen Bet v 1. Clin. Exp. Immunol. 107, 536-541 (1997).

Benjamin D C et al. The Antigenic Structure of Proteins: A Reappraisal. Ann. Rev. Immunol. 2, 67-101 (1984).

Boel E. et al. Functional human monoclonal antibodies of all isotypes constructed from phage display library-derived single-chain Fv antibody fragments J. Immunol. Meth. 26, 153-166 (2000).

Briner et al. Peripheral T-cell tolerance induced in naive and primed mice by subcutaneous injection of peptides from the major cat allergen Fel d I. Proc. Natl. Acad. Sci. USA 90, 7608-7612 (1993).

Carballido J. M. et al. T Cell Epitope Specificity in Human Allergic and Nonallergic Subjects to Bee Venom Phospholipase A2. J. Immunol. 150, 3582-3591 (1993).

Castro F F M, Palma M S, Brochetto-Braga M R, Malaspina O, Lazaretti J, Baldo M A B. Biochemical properties and study of antigenic cross-reactivity between Africanized honey bee and wasp venom, J Invest Allergol Clin Immunol 4, 37-41 (1994).

Dhillon M. et al. Mapping human T cell epitopes on phospholipase A2: The major bee-venom allergen. J. Allergy Clin. Immunol. 90, 42-51 (1992).

Dotimas E M, Hider R C, Honeybee venom, Bee World 68(2) 51-70 (1987).

Edwards M. R. et al. Analysis of IgE Antibodies from a Patient with Atopic Dermatitis: Biased V Gene Usage and Evidence for Polyreactive IgE Heavy Chain Complementary-Determining Region 3. J Immunol 168, 6305-6313 (2002).

Eich-Wanger C, Müller U R. Bee sting allergy in beekeepers. Clin Exp Allergy 28, 1292-98 (1998).

Elbein A D. The role of N-linked oligosaccharides in glycoprotein function, Trends in Biotech 91, 346-352(1991).

Fraternali F. and Cavallo L. Parameter optimized surfaces (POPS): analysis of interactions and conformational changes in the ribosome. Nucleic Acids Res. 30, 2950-2960 (2002).

Ganglberger E. et al. Allergen mimotopes for 3-dimensional epitope search and induction of antibodies inhibiting human IgE. FASEB J. 14, 2177-2184 (2000).

Gmachl M, Kreil G, Bee venom hyaluronidase is homologous to a membrane protein of mammalian sperm; Proc. Natl. Acad. Sci. U.S.A. 90, 3569-3573 (1993).

Habermann, E, Bienen- and Wespenstiche aus medizinischer Sicht, Allgemeine Deutsche Imkerzeitung (ADIZ) 11 p., 301-304 (1974).

Hamilton R G. Diagnosis of Hymenoptera venom sensitivity, Curr Opin Allergy Clin Immunol 2, 347-351 (2002).

Helbling A et al., Incidence of anaphylaxis with circulatory symptoms: a study over a 3-year period comprising 940,000 inhabitants of the Swiss Canton Bern, Clin Exp Allergy 34, 285-290 (2004).

Hemmer W et al. Identification by immunoblot of venom glycoproteins displaying immunoglobulin E-binding N-glycans as cross-reactive allergens in honeybee and yellow jacket venom, Clin Exp Allergy 34, 460-469 (2004).

Hoffman D R, Hymenoptera venom proteins, in Natural Toxins 2, Edts. Singh B R and Tu A T, Plenum Press, New York 169-186 (1996).

Hoffman D R, Dove D E, Moffitt J E, Stafford C T. Allergens in Hymenoptera venom XII. Cross-reativity and multiple reactivity between fire ant venom, bee and wasp venoms, J Allergy Clin Immunol 82, 828-34 (1988).

Hoffman D R, Shipman W H, Allergens in bee venom. I. Separation and identification of the major allergen, J Allergy Clin Immunol 58, 551-62 (1976).

Hoffman D R, Shipman W H, Babin D, Allergens in bee venom II. Two new high molecular weight allergenic specificities, J Allergy Clin Immunol. 59(2), 147-53 (1977).

Hoyne G F et al. Inhibition of T Cell and Antibody Response to House Dust Mite Allergen by Inhalation of the Dominant T Cell Epitope in Naive and Sensitized Mice. J. Exp. Med. 178, 1783-1788 (1993).

Huby R D J et al. Why are Some Proteins Allergens ? Tox Sci 55 235-246 (2000).

Hunt K J, Valentine M D, Sobotka A K, Benton A W, Lichtenstein L M. A controlled study of immunotherapy in insect hypersensitivity. New Engl. J. Med. 229, 157 (1978).

Jacobson R S and Hoffman D R. Honey-bee venom acid phosphatase is a member of the prostatic acid phosphatase family, J Allergy Immunol 95, 372 (1995).

Jenkins N et al. Getting the glycosylation right: Implications for the biotechnology industry, Nature Biotech 14, 975-981 (1996).

Jutel M. et al. Mechanism of allergen specific immunotherapy—T-cell tolerance and more. Allergy 61, 796-807 (2006).

Karamloo F. et al. Prevention of allergy by a recombinant multi-allergen vaccine with reduced IgE binding and preserved T cell epitopes. Eur. J. Immunol. 35, 3268-3276 (2005).

Kemeny D M, MacKenzie-Mills M, Harries M G, Youlten U, Lessof M H. Antibodies to purified bee venom proteins and peptides. II. A detailed study of changes in IgE and IgG antibodies to individual bee venom antigens. J Allergy Clin Immunol. 72, 376-85(1983).

Kettner A, Hughes G J, Frutiger S, Astori M, Roggero M, Spertini F, Corradin G. Api m 6: a new bee venom allergen, *J. Allergy Clin. Immunol.* 107, 914-920 (2001).

Kettner A, Henry H, Hyghes G, Corradin G, Spertini F. IgE and T-cell responses to high-molecular weight allergens from bee venom, Clin Exp Allergy 29, 394-401 (1999).

King T P. Insect venom allergens. Monogr. Allergy 28, 84-100 (1990).

King T P, Spangfort M D. Structure and Biology of Stinging Insect Venom Allergens, Int Arch Allergy Immunol 123, 99-106 (2000).

Kuchler K, Gmachl M, Sippl M J, Kreil G, Analysis of the cDNA for phospholipase A2 from honeybee venom glands. The deduced amino acid sequence reveals homology to the corresponding vertebrate enzymes, Eur. J. Biochem. 184, 249-254 (1989).

Kulike, H. Zur Struktur und Funktionsweise des Hymenopterenstachels, Amts-und Mitteilungsblatt der Bundesanstalt für Materialpriifung 16 p., 519-550 (1986).

Lebecque S et al Immunologic characterization of monoclonal antibodies that modulate human IgE binding to the major birch pollen allergen Bet v 1. J. Allergy Clin. Immunol. 99, 374-384 (1997).

MacKenzie T and Dosch H-M. Clonal and Molecular Characterization of the Human IgE-Committed B Cell Subset. J. Exp. Med. 169, 407-430 (1989)

Mirza O et al. Dominant Epitopes and Allergic Cross-Reactivity: Complex Formation Between a Fab Fragment of a Monoclonal Murine IgG Antibody and the Major Allergen from Birch Pollen Bet v 1. J. Immunol. 165, 331-338 (2000).

Müller U et al. Successful immunotherapy with T-cell epitope peptides of bee venom phospholipase A2 induces specific T-cell anergy in patients allergic to bee venom. J. Allergy Clin. Immunol. 101, 747-754 (1998).

Müller U R, Recombinant Hymenoptera venom allergens, Allergy 57, 570-576 (2002).

Müller U R, New Developments in the Diagnosis and Treatment of Hymenoptera Venom Allergy, Int. Arch Allergy Immunol, 124, 447-453 (2001).

Niederberger V et al. Vaccination with genetically engineered allergens prevents progression of allergic disease. Proc. Natl. Acad. Sci. USA 101, 14677-14682 (2004).

Petersen A, Mundt C. Investigations on the carbohydrate moieties of glycoprotein allergens, J Chromat B 756, 141-150 (2001).

Poulsen L K. In-vitro diagnosis: serum-based methods used for risk assessment in allergenic food, Curr. Opin. Allery Clin. Immunol. 1, 249-254 (2001).

Powers D. B. et al. Expression of single-chain Fv-Fc fusions in *Pichia pastoris* J Immunol Meth. 251, 123-135 (2001).

Schiavino D, Nucera E, Pollastrini E, De Pasquale T, Buonomo A, Bartolozzi F, Lombardo C, Roncallo C, Patriarca G. Specific ultrarush desensitization in Hymenoptera venom-allergic patients. Ann Allergy Asthma Immunol, 92(4):409-13 (2004).

Schmid-Grendelmeier P, Cameri R, Recombinant Allergens for Skin Testing, Int Arch Allergy Immunol 125, 96-111 (2001).

Sobotka A, Franklin R, Valentine M, Adkinson N F, Lichtenstein L M, Honey bee venom: Phospholipase A as the major allergen, J Clin Allergy Clin Immunol 53, 103 (1974).

Sobotka A K, Franklin R M, Adkinson N F, Valentine M D, Baer H, Lichtenstein L M. Allergy to insect stings. II. Phospholipase A: The major allergen in honeybee venom, J Allergy Clin Immunol 57, 29-40 (1976).

Soldatova L N, Bakst J B, Hoffman D R, Slater J E, Molecular cloning of a new honey bee allergen, acid phosphatase, J. Allergy Clin. Immunol. 105, 5378 (2000).

Steinberger P. et al. Construction of a Combinatorial IgE Library from a Allergic Patient. J. Biol. Chem. 271, 10967-10972 (1996).

Sudowe S, Montermann E, Steitz J, Tüting T, Knop J, Reske-Kunz A B. Efficacy of recombinant adenovirus as vector for allergen gene therapy in a mouse model of type I allergy. Gene Ther 9, 147-56 (2002).

Tretter V et al. Fucose alpha1,3-Linked to the Core Region of Glycoprotein N-Glycans Creates an Important Epitope for IgE from Honeybee Venom Allergic Individuals, Int Arch Allergy Immunol 102, 259-266 (1993).

Valenta R. et al. The Immunoglobulin E-Allergen Interaction: A Target for Therapy of Type I Allergic Diseases. Int. Arch. Immunol. 116, 167-176 (1998).

Varney V. A. et al. Usefulness of immunotherapy in patients with severe summer hay fever uncontrolled by antiallergic drugs. British Medical J. 302, 265-269 (1991).

Vlasak R, Unger-Ullmann C, Kreil G, Frischauf A-M, Nucleotide sequence of cloned cDNA coding for honeybee prepromelittin, *Eur. J. Biochem* 135, 123-126 (1983).

Williams L W, Bock S A. Skin Testin and Food Challenges in Allergy and Immunology Practice, Clin. Rev. Allergy Immunol. 17, 323-338 (1999).

Wypych J I, Abeyounis C J, Reisman R E, Analysis of differing patterns of cross-reactivity of Honeybee and Yellow jacket venom-specific-IgE: Use of purified venom fractions. Int Arch Allergy Appl Immunol 89, 60-6 (1989).

Zhang Q. Immune epitope database analysis resource (IEDB-AR) Nucleic Acid Res. 36, W513-W518 (2008).

TABLE 1

Bee venom components

| Component type | name | % weight of dry mass |
|---|---|---|
| Proteins | Phospholipase A2 (Api m 1) | 10-12 |
|  | Hyaluronidase (Api m 2) | 1-3 |
|  | Phosphatase, Glucosidase | 1-2 |
| Peptides | Melittin (Api m 4) | 50-55 |
|  | Secapin, MCD-peptide | 1.5-4 |
|  | Tertiapamin, Apamin, Procamin | 2-5 |
|  | Other small peptides | 13-15 |
| Biogene amines | Histamine | 0.5-2 |
|  | Dopamine | 0.2-1 |
|  | Norepinephrine | 0.1-0.5 |
|  | Sugars (Glucose, Fructose) | 2 |
| Phospholipids |  | 5 |
| Amino acids |  | — |
| Volatile substances | Pheromones | 4-8 |
| Minerals |  | 3-4 |

TABLE 2

Identified bee allergens

| Allergen | Common name | Size (processed) | Weight | SwissProt | Reference |
|---|---|---|---|---|---|
| Api m 1 | Phospholipase A2 | 134 aa | 15.2 kDa | P00630 | Kuchler et al 1989 |
| Api m 2 | Hyaluronidase | 349 aa | 40.7 kDa | Q08169 | Gmachl and Kreil 1993 |
| Api m 3 | Acid Phosphatase | nd | 45 kDa | — | Barboni et al 1987 |
| Api m 4 | Melittin | 26 aa | 2.8 kDa | P01501 | Vlasak et al 1983 |
| Api m 5 | Allergen C | nd | 105 kDa | — | Hoffman et al 1977 |
| Api m 6 | — | 71 aa | 7.5 kDa | P83563 | Kettner et al 2001 |

TABLE 3

NetMHCII 1.0 predicted T cell epitopes in Api m 3 (only strong and weak binders)

| Allele | Peptide No. | Start No.* nucleic acid | End No.* nucleic acid | Start No.** amino acid | End No.** amino acid | Length amino acid |
|---|---|---|---|---|---|---|
| DRB1*0101 | 1 | 307 | 351 | 103 | 117 | 15 |
| | 2 | 310 | 354 | 104 | 118 | 15 |
| | 3 | 313 | 357 | 105 | 119 | 15 |
| | 4 | 316 | 360 | 106 | 120 | 15 |
| | 5 | 319 | 363 | 107 | 121 | 15 |
| | 6 | 523 | 567 | 175 | 189 | 15 |
| | 7 | 526 | 570 | 176 | 190 | 15 |
| | 8 | 514 | 558 | 172 | 186 | 15 |
| | 9 | 517 | 561 | 173 | 187 | 15 |
| | 10 | 520 | 564 | 174 | 188 | 15 |
| | 11 | 655 | 699 | 219 | 233 | 15 |
| | 12 | 661 | 705 | 221 | 235 | 15 |
| | 13 | 658 | 702 | 220 | 234 | 15 |
| | 14 | 652 | 696 | 218 | 232 | 15 |
| | 15 | 664 | 708 | 222 | 236 | 15 |
| | 16 | 889 | 933 | 297 | 311 | 15 |
| | 17 | 880 | 924 | 294 | 308 | 15 |
| | 18 | 883 | 927 | 295 | 309 | 15 |
| | 19 | 886 | 930 | 296 | 310 | 15 |
| | 20 | 892 | 936 | 298 | 312 | 15 |
| | 21 | 532 | 576 | 178 | 192 | 15 |
| | 22 | 529 | 573 | 177 | 191 | 15 |
| | 23 | 322 | 366 | 108 | 122 | 15 |
| | 24 | 325 | 369 | 109 | 123 | 15 |
| | 25 | 667 | 711 | 223 | 237 | 15 |
| | 26 | 670 | 714 | 224 | 238 | 15 |
| | 27 | 622 | 666 | 208 | 222 | 15 |
| | 28 | 535 | 579 | 179 | 193 | 15 |
| | 29 | 184 | 228 | 62 | 76 | 15 |
| | 30 | 190 | 234 | 64 | 78 | 15 |
| | 31 | 187 | 231 | 63 | 77 | 15 |
| | 32 | 193 | 237 | 65 | 79 | 15 |
| | 33 | 247 | 291 | 83 | 97 | 15 |
| | 34 | 253 | 297 | 85 | 99 | 15 |
| | 35 | 895 | 939 | 299 | 313 | 15 |
| | 36 | 250 | 294 | 84 | 98 | 15 |
| | 37 | 625 | 669 | 209 | 223 | 15 |
| | 38 | 628 | 672 | 210 | 224 | 15 |
| | 39 | 244 | 288 | 82 | 96 | 15 |
| | 40 | 181 | 225 | 61 | 75 | 15 |
| | 41 | 241 | 285 | 81 | 95 | 15 |
| | 42 | 898 | 942 | 300 | 314 | 15 |
| | 43 | 1066 | 1110 | 356 | 370 | 15 |
| | 44 | 619 | 663 | 207 | 221 | 15 |
| | 45 | 1069 | 1113 | 357 | 371 | 15 |
| | 46 | 616 | 660 | 206 | 220 | 15 |
| | 47 | 1063 | 1107 | 355 | 369 | 15 |
| | 48 | 1060 | 1104 | 354 | 368 | 15 |
| | 49 | 256 | 300 | 86 | 100 | 15 |
| | 50 | 793 | 837 | 265 | 279 | 15 |
| | 51 | 259 | 303 | 87 | 101 | 15 |
| | 52 | 541 | 585 | 181 | 195 | 15 |
| | 53 | 754 | 798 | 252 | 266 | 15 |
| | 54 | 796 | 840 | 266 | 280 | 15 |
| | 55 | 751 | 795 | 251 | 265 | 15 |
| | 56 | 775 | 819 | 259 | 273 | 15 |
| | 57 | 784 | 828 | 262 | 276 | 15 |
| | 58 | 802 | 846 | 268 | 282 | 15 |
| | 59 | 778 | 822 | 260 | 274 | 15 |

TABLE 3-continued

NetMHCII 1.0 predicted T cell epitopes in Api m 3 (only strong and weak binders)

| Allele | Peptide No. | Start No.* nucleic acid | End No.* nucleic acid | Start No.** amino acid | End No.** amino acid | Length amino acid |
|---|---|---|---|---|---|---|
| | 60 | 745 | 789 | 249 | 263 | 15 |
| | 61 | 748 | 792 | 250 | 264 | 15 |
| | 62 | 1072 | 1116 | 358 | 372 | 15 |
| | 63 | 787 | 831 | 263 | 277 | 15 |
| | 64 | 781 | 825 | 261 | 275 | 15 |
| | 65 | 799 | 843 | 267 | 281 | 15 |
| | 66 | 805 | 849 | 269 | 283 | 15 |
| | 67 | 742 | 786 | 248 | 262 | 15 |
| | 68 | 235 | 279 | 79 | 93 | 15 |
| | 69 | 238 | 282 | 80 | 94 | 15 |
| | 70 | 196 | 240 | 66 | 80 | 15 |
| | 71 | 631 | 675 | 211 | 225 | 15 |
| | 72 | 538 | 582 | 180 | 194 | 15 |
| | 73 | 634 | 678 | 212 | 226 | 15 |
| | 74 | 1075 | 1119 | 359 | 373 | 15 |
| | 75 | 199 | 243 | 67 | 81 | 15 |
| | 76 | 610 | 654 | 204 | 218 | 15 |
| | 77 | 547 | 591 | 183 | 197 | 15 |
| | 78 | 613 | 657 | 205 | 219 | 15 |
| | 79 | 550 | 594 | 184 | 198 | 15 |
| | 80 | 1057 | 1101 | 353 | 367 | 15 |
| | 81 | 553 | 597 | 185 | 199 | 15 |
| | 82 | 544 | 588 | 182 | 196 | 15 |
| | 83 | 301 | 345 | 101 | 115 | 15 |
| | 84 | 304 | 348 | 102 | 116 | 15 |
| | 85 | 262 | 306 | 88 | 102 | 15 |
| | 86 | 385 | 429 | 129 | 143 | 15 |
| | 87 | 388 | 432 | 130 | 144 | 15 |
| | 88 | 673 | 717 | 225 | 239 | 15 |
| | 89 | 382 | 426 | 128 | 142 | 15 |
| | 90 | 379 | 423 | 127 | 141 | 15 |
| | 91 | 685 | 729 | 229 | 243 | 15 |
| | 92 | 265 | 309 | 89 | 103 | 15 |
| | 93 | 679 | 723 | 227 | 241 | 15 |
| | 94 | 808 | 852 | 270 | 284 | 15 |
| | 95 | 562 | 606 | 188 | 202 | 15 |
| | 96 | 760 | 804 | 254 | 268 | 15 |
| | 97 | 757 | 801 | 253 | 267 | 15 |
| | 98 | 682 | 726 | 228 | 242 | 15 |
| | 99 | 688 | 732 | 230 | 244 | 15 |
| | 100 | 91 | 135 | 31 | 45 | 15 |
| | 101 | 232 | 276 | 78 | 92 | 15 |
| | 102 | 94 | 138 | 32 | 46 | 15 |
| | 103 | 676 | 720 | 226 | 240 | 15 |
| | 104 | 556 | 600 | 186 | 200 | 15 |
| | 105 | 790 | 834 | 264 | 278 | 15 |
| | 106 | 229 | 273 | 77 | 91 | 15 |
| | 107 | 877 | 921 | 293 | 307 | 15 |
| | 108 | 226 | 270 | 76 | 90 | 15 |
| | 109 | 1021 | 1065 | 341 | 355 | 15 |
| | 110 | 394 | 438 | 132 | 146 | 15 |
| | 111 | 1015 | 1059 | 339 | 353 | 15 |
| | 112 | 1018 | 1062 | 340 | 354 | 15 |
| | 113 | 1024 | 1068 | 342 | 356 | 15 |
| | 114 | 811 | 855 | 271 | 285 | 15 |
| | 115 | 511 | 555 | 171 | 185 | 15 |
| | 116 | 391 | 435 | 131 | 145 | 15 |
| | 117 | 691 | 735 | 231 | 245 | 15 |
| | 118 | 1012 | 1056 | 338 | 352 | 15 |
| | 119 | 508 | 552 | 170 | 184 | 15 |
| | 120 | 958 | 1002 | 320 | 334 | 15 |
| | 121 | 568 | 612 | 190 | 204 | 15 |
| | 122 | 565 | 609 | 189 | 203 | 15 |
| | 123 | 574 | 618 | 192 | 206 | 15 |
| | 124 | 571 | 615 | 191 | 205 | 15 |
| | 125 | 955 | 999 | 319 | 333 | 15 |
| | 126 | 82 | 126 | 28 | 42 | 15 |
| | 127 | 85 | 129 | 29 | 43 | 15 |
| | 128 | 874 | 918 | 292 | 306 | 15 |
| | 129 | 88 | 132 | 30 | 44 | 15 |
| | 130 | 505 | 549 | 169 | 183 | 15 |
| DRB1*0401 | 131 | 616 | 660 | 206 | 220 | 15 |
| | 132 | 622 | 666 | 208 | 222 | 15 |
| | 133 | 619 | 663 | 207 | 221 | 15 |
| | 134 | 613 | 657 | 205 | 219 | 15 |

TABLE 3-continued

NetMHCII 1.0 predicted T cell epitopes in Api m 3 (only strong and weak binders)

| Allele | Peptide No. | Start No.* nucleic acid | End No.* nucleic acid | Start No.** amino acid | End No.** amino acid | Length amino acid |
|---|---|---|---|---|---|---|
| | 135 | 610 | 654 | 204 | 218 | 15 |
| | 136 | 625 | 669 | 209 | 223 | 15 |
| | 137 | 628 | 672 | 210 | 224 | 15 |
| | 138 | 190 | 234 | 64 | 78 | 15 |
| | 139 | 187 | 231 | 63 | 77 | 15 |
| | 140 | 193 | 237 | 65 | 79 | 15 |
| | 141 | 181 | 225 | 61 | 75 | 15 |
| | 142 | 184 | 228 | 62 | 76 | 15 |
| | 143 | 745 | 789 | 249 | 263 | 15 |
| | 144 | 742 | 786 | 248 | 262 | 15 |
| | 145 | 748 | 792 | 250 | 264 | 15 |
| | 146 | 754 | 798 | 252 | 266 | 15 |
| | 147 | 196 | 240 | 66 | 80 | 15 |
| | 148 | 199 | 243 | 67 | 81 | 15 |
| | 149 | 751 | 795 | 251 | 265 | 15 |
| | 150 | 880 | 924 | 294 | 308 | 15 |
| | 151 | 883 | 927 | 295 | 309 | 15 |
| | 152 | 514 | 558 | 172 | 186 | 15 |
| | 153 | 886 | 930 | 296 | 310 | 15 |
| | 154 | 889 | 933 | 297 | 311 | 15 |
| | 155 | 517 | 561 | 173 | 187 | 15 |
| | 156 | 511 | 555 | 171 | 185 | 15 |
| | 157 | 520 | 564 | 174 | 188 | 15 |
| | 158 | 892 | 936 | 298 | 312 | 15 |
| DRB1*0404 | 159 | 703 | 747 | 235 | 249 | 15 |
| | 160 | 697 | 741 | 233 | 247 | 15 |
| | 161 | 691 | 735 | 231 | 245 | 15 |
| | 162 | 700 | 744 | 234 | 248 | 15 |
| | 163 | 694 | 738 | 232 | 246 | 15 |
| | 164 | 667 | 711 | 223 | 237 | 15 |
| | 165 | 679 | 723 | 227 | 241 | 15 |
| | 166 | 676 | 720 | 226 | 240 | 15 |
| | 167 | 670 | 714 | 224 | 238 | 15 |
| | 168 | 673 | 717 | 225 | 239 | 15 |
| | 169 | 706 | 750 | 236 | 250 | 15 |
| | 170 | 709 | 753 | 237 | 251 | 15 |
| | 171 | 562 | 606 | 188 | 202 | 15 |
| | 172 | 685 | 729 | 229 | 243 | 15 |
| | 173 | 682 | 726 | 228 | 242 | 15 |
| | 174 | 565 | 609 | 189 | 203 | 15 |
| | 175 | 568 | 612 | 190 | 204 | 15 |
| | 176 | 841 | 885 | 281 | 295 | 15 |
| | 177 | 838 | 882 | 280 | 294 | 15 |
| DRB1*0405 | 178 | 301 | 345 | 101 | 115 | 15 |
| | 179 | 556 | 600 | 186 | 200 | 15 |
| | 180 | 553 | 597 | 185 | 199 | 15 |
| | 181 | 967 | 1011 | 323 | 337 | 15 |
| | 182 | 289 | 333 | 97 | 111 | 15 |
| | 183 | 292 | 336 | 98 | 112 | 15 |
| | 184 | 307 | 351 | 103 | 117 | 15 |
| | 185 | 304 | 348 | 102 | 116 | 15 |
| | 186 | 559 | 603 | 187 | 201 | 15 |
| | 187 | 970 | 1014 | 324 | 338 | 15 |
| | 188 | 973 | 1017 | 325 | 339 | 15 |
| | 189 | 562 | 606 | 188 | 202 | 15 |
| | 190 | 76 | 120 | 26 | 40 | 15 |
| | 191 | 73 | 117 | 25 | 39 | 15 |
| | 192 | 475 | 519 | 159 | 173 | 15 |
| | 193 | 514 | 558 | 172 | 186 | 15 |
| | 194 | 79 | 123 | 27 | 41 | 15 |
| | 195 | 82 | 126 | 28 | 42 | 15 |
| | 196 | 976 | 1020 | 326 | 340 | 15 |
| | 197 | 295 | 339 | 99 | 113 | 15 |
| | 198 | 478 | 522 | 160 | 174 | 15 |
| | 199 | 517 | 561 | 173 | 187 | 15 |
| | 200 | 979 | 1023 | 327 | 341 | 15 |
| | 201 | 511 | 555 | 171 | 185 | 15 |
| | 202 | 298 | 342 | 100 | 114 | 15 |
| | 203 | 508 | 552 | 170 | 184 | 15 |
| | 204 | 565 | 609 | 189 | 203 | 15 |
| | 205 | 310 | 354 | 104 | 118 | 15 |
| | 206 | 481 | 525 | 161 | 175 | 15 |
| | 207 | 484 | 528 | 162 | 176 | 15 |
| | 208 | 883 | 927 | 295 | 309 | 15 |
| | 209 | 313 | 357 | 105 | 119 | 15 |

TABLE 3-continued

NetMHCII 1.0 predicted T cell epitopes in Api m 3 (only strong and weak binders)

| Allele | Peptide No. | Start No.* nucleic acid | End No.* nucleic acid | Start No.** amino acid | End No.** amino acid | Length amino acid |
|---|---|---|---|---|---|---|
| | 210 | 880 | 924 | 294 | 308 | 15 |
| | 211 | 487 | 531 | 163 | 177 | 15 |
| | 212 | 70 | 114 | 24 | 38 | 15 |
| | 213 | 394 | 438 | 132 | 146 | 15 |
| | 214 | 397 | 441 | 133 | 147 | 15 |
| | 215 | 886 | 930 | 296 | 310 | 15 |
| | 216 | 391 | 435 | 131 | 145 | 15 |
| | 217 | 889 | 933 | 297 | 311 | 15 |
| | 218 | 385 | 429 | 129 | 143 | 15 |
| | 219 | 388 | 432 | 130 | 144 | 15 |
| | 220 | 625 | 669 | 209 | 223 | 15 |
| | 221 | 505 | 549 | 169 | 183 | 15 |
| DRB1*0701 | 222 | 622 | 666 | 208 | 222 | 15 |
| | 223 | 625 | 669 | 209 | 223 | 15 |
| | 224 | 628 | 672 | 210 | 224 | 15 |
| | 225 | 619 | 663 | 207 | 221 | 15 |
| | 226 | 616 | 660 | 206 | 220 | 15 |
| | 227 | 631 | 675 | 211 | 225 | 15 |
| | 228 | 634 | 678 | 212 | 226 | 15 |
| | 229 | 553 | 597 | 185 | 199 | 15 |
| | 230 | 316 | 360 | 106 | 120 | 15 |
| | 231 | 313 | 357 | 105 | 119 | 15 |
| | 232 | 556 | 600 | 186 | 200 | 15 |
| | 233 | 319 | 363 | 107 | 121 | 15 |
| | 234 | 559 | 603 | 187 | 201 | 15 |
| | 235 | 598 | 642 | 200 | 214 | 15 |
| | 236 | 601 | 645 | 201 | 215 | 15 |
| | 237 | 604 | 648 | 202 | 216 | 15 |
| | 238 | 595 | 639 | 199 | 213 | 15 |
| | 239 | 562 | 606 | 188 | 202 | 15 |
| DRB1*0901 | 240 | 514 | 558 | 172 | 186 | 15 |
| | 241 | 622 | 666 | 208 | 222 | 15 |
| | 242 | 517 | 561 | 173 | 187 | 15 |
| | 243 | 628 | 672 | 210 | 224 | 15 |
| | 244 | 625 | 669 | 209 | 223 | 15 |
| | 245 | 511 | 555 | 171 | 185 | 15 |
| | 246 | 814 | 858 | 272 | 286 | 15 |
| | 247 | 817 | 861 | 273 | 287 | 15 |
| DRB1*1101 | 248 | 514 | 558 | 172 | 186 | 15 |
| | 249 | 517 | 561 | 173 | 187 | 15 |
| | 250 | 520 | 564 | 174 | 188 | 15 |
| | 251 | 523 | 567 | 175 | 189 | 15 |
| | 252 | 526 | 570 | 176 | 190 | 15 |
| | 253 | 565 | 609 | 189 | 203 | 15 |
| | 254 | 562 | 606 | 188 | 202 | 15 |
| | 255 | 568 | 612 | 190 | 204 | 15 |
| | 256 | 574 | 618 | 192 | 206 | 15 |
| | 257 | 571 | 615 | 191 | 205 | 15 |
| DRB1*1302 | 258 | 622 | 666 | 208 | 222 | 15 |
| | 259 | 625 | 669 | 209 | 223 | 15 |
| | 260 | 628 | 672 | 210 | 224 | 15 |
| | 261 | 619 | 663 | 207 | 221 | 15 |
| | 262 | 616 | 660 | 206 | 220 | 15 |
| | 263 | 631 | 675 | 211 | 225 | 15 |
| | 264 | 1066 | 1110 | 356 | 370 | 15 |
| | 265 | 1069 | 1113 | 357 | 371 | 15 |
| | 266 | 634 | 678 | 212 | 226 | 15 |
| | 267 | 1063 | 1107 | 355 | 369 | 15 |
| | 268 | 1072 | 1116 | 358 | 372 | 15 |
| | 269 | 1075 | 1119 | 359 | 373 | 15 |
| | 270 | 1060 | 1104 | 354 | 368 | 15 |
| | 271 | 610 | 654 | 204 | 218 | 15 |
| | 272 | 613 | 657 | 205 | 219 | 15 |
| | 273 | 247 | 291 | 83 | 97 | 15 |
| | 274 | 253 | 297 | 85 | 99 | 15 |
| | 275 | 250 | 294 | 84 | 98 | 15 |
| | 276 | 964 | 1008 | 322 | 336 | 15 |
| | 277 | 259 | 303 | 87 | 101 | 15 |
| | 278 | 568 | 612 | 190 | 204 | 15 |
| | 279 | 256 | 300 | 86 | 100 | 15 |
| | 280 | 562 | 606 | 188 | 202 | 15 |
| | 281 | 571 | 615 | 191 | 205 | 15 |
| | 282 | 565 | 609 | 189 | 203 | 15 |
| | 283 | 1057 | 1101 | 353 | 367 | 15 |
| | 284 | 574 | 618 | 192 | 206 | 15 |

TABLE 3-continued

NetMHCII 1.0 predicted T cell epitopes in Api m 3 (only strong and weak binders)

| Allele | Peptide No. | Start No.* nucleic acid | End No.* nucleic acid | Start No.** amino acid | End No.** amino acid | Length amino acid |
|---|---|---|---|---|---|---|
|  | 285 | 967 | 1011 | 323 | 337 | 15 |
|  | 286 | 679 | 723 | 227 | 241 | 15 |
|  | 287 | 970 | 1014 | 324 | 338 | 15 |
|  | 288 | 682 | 726 | 228 | 242 | 15 |
|  | 289 | 958 | 1002 | 320 | 334 | 15 |
|  | 290 | 637 | 681 | 213 | 227 | 15 |
|  | 291 | 676 | 720 | 226 | 240 | 15 |
|  | 292 | 961 | 1005 | 321 | 335 | 15 |
|  | 293 | 871 | 915 | 291 | 305 | 15 |
|  | 294 | 955 | 999 | 319 | 333 | 15 |
|  | 295 | 874 | 918 | 292 | 306 | 15 |
|  | 296 | 973 | 1017 | 325 | 339 | 15 |
|  | 297 | 670 | 714 | 224 | 238 | 15 |
|  | 298 | 673 | 717 | 225 | 239 | 15 |
|  | 299 | 877 | 921 | 293 | 307 | 15 |
|  | 300 | 106 | 150 | 36 | 50 | 15 |
|  | 301 | 103 | 147 | 35 | 49 | 15 |
| DRB1*1501 | 302 | 880 | 924 | 294 | 308 | 15 |
|  | 303 | 883 | 927 | 295 | 309 | 15 |
|  | 304 | 886 | 930 | 296 | 310 | 15 |
|  | 305 | 889 | 933 | 297 | 311 | 15 |
|  | 306 | 892 | 936 | 298 | 312 | 15 |
|  | 307 | 874 | 918 | 292 | 306 | 15 |
|  | 308 | 877 | 921 | 293 | 307 | 15 |
|  | 309 | 253 | 297 | 85 | 99 | 15 |
| DRB4*0101 | 310 | 553 | 597 | 185 | 199 | 15 |
|  | 311 | 556 | 600 | 186 | 200 | 15 |
|  | 312 | 559 | 603 | 187 | 201 | 15 |
|  | 313 | 565 | 609 | 189 | 203 | 15 |
|  | 314 | 562 | 606 | 188 | 202 | 15 |
|  | 315 | 334 | 378 | 112 | 126 | 15 |
|  | 316 | 331 | 375 | 111 | 125 | 15 |
|  | 317 | 337 | 381 | 113 | 127 | 15 |
|  | 318 | 340 | 384 | 114 | 128 | 15 |
|  | 319 | 343 | 387 | 115 | 129 | 15 |
|  | 320 | 568 | 612 | 190 | 204 | 15 |
|  | 321 | 571 | 615 | 191 | 205 | 15 |
|  | 322 | 256 | 300 | 86 | 100 | 15 |
|  | 323 | 262 | 306 | 88 | 102 | 15 |
|  | 324 | 259 | 303 | 87 | 101 | 15 |
|  | 325 | 265 | 309 | 89 | 103 | 15 |
|  | 326 | 784 | 828 | 262 | 276 | 15 |
|  | 327 | 787 | 831 | 263 | 277 | 15 |
|  | 328 | 793 | 837 | 265 | 279 | 15 |
|  | 329 | 796 | 840 | 266 | 280 | 15 |
|  | 330 | 349 | 393 | 117 | 131 | 15 |
|  | 331 | 346 | 390 | 116 | 130 | 15 |
|  | 332 | 268 | 312 | 90 | 104 | 15 |
|  | 333 | 790 | 834 | 264 | 278 | 15 |
|  | 334 | 826 | 870 | 276 | 290 | 15 |
|  | 335 | 829 | 873 | 277 | 291 | 15 |
|  | 336 | 832 | 876 | 278 | 292 | 15 |
|  | 337 | 835 | 879 | 279 | 293 | 15 |
| DRB5*0101 | 338 | 316 | 360 | 106 | 120 | 15 |
|  | 339 | 310 | 354 | 104 | 118 | 15 |
|  | 340 | 319 | 363 | 107 | 121 | 15 |
|  | 341 | 313 | 357 | 105 | 119 | 15 |
|  | 342 | 553 | 597 | 185 | 199 | 15 |
|  | 343 | 82 | 126 | 28 | 42 | 15 |
|  | 344 | 802 | 846 | 268 | 282 | 15 |
|  | 345 | 805 | 849 | 269 | 283 | 15 |
|  | 346 | 307 | 351 | 103 | 117 | 15 |

*Numbering according to SEQ ID NO: 1
**Numbering according to SEQ ID NO: 2

TABLE 4

NetMHCIIPAN predicted T cell epitopes in Api m 3 (only strong binders)

| Allele | Peptide No. | Start No.* nucleic acid | End No.* Nucleic acid | Start No.** amino acid | End No.** amino acid | Length amino acid |
|---|---|---|---|---|---|---|
| DRB1*0101 | 1 | 523 | 567 | 175 | 189 | 15 |
| | 2 | 625 | 669 | 209 | 223 | 15 |
| | 3 | 511 | 555 | 171 | 185 | 15 |
| | 4 | 316 | 360 | 106 | 120 | 15 |
| | 5 | 889 | 933 | 297 | 311 | 15 |
| | 6 | 652 | 696 | 218 | 232 | 15 |
| | 7 | 1066 | 1110 | 356 | 370 | 15 |
| | 8 | 751 | 795 | 251 | 265 | 15 |
| | 9 | 961 | 1005 | 321 | 335 | 15 |
| | 10 | 250 | 294 | 84 | 98 | 15 |
| | 11 | 535 | 579 | 179 | 193 | 15 |
| | 12 | 742 | 786 | 248 | 262 | 15 |
| | 13 | 1018 | 1062 | 340 | 354 | 15 |
| | 14 | 871 | 915 | 291 | 305 | 15 |
| | 15 | 610 | 654 | 204 | 218 | 15 |
| | 16 | 676 | 720 | 226 | 240 | 15 |
| | 17 | 664 | 708 | 222 | 236 | 15 |
| | 18 | 190 | 234 | 64 | 78 | 15 |
| | 19 | 772 | 816 | 258 | 272 | 15 |
| DRB1*0102 | 20 | 523 | 567 | 175 | 189 | 15 |
| | 21 | 652 | 696 | 218 | 232 | 15 |
| | 22 | 529 | 573 | 177 | 191 | 15 |
| | 23 | 889 | 933 | 297 | 311 | 15 |
| | 24 | 511 | 555 | 171 | 185 | 15 |
| | 25 | 625 | 669 | 209 | 223 | 15 |
| | 26 | 1075 | 1119 | 359 | 373 | 15 |
| | 27 | 1066 | 1110 | 356 | 370 | 15 |
| | 28 | 316 | 360 | 106 | 120 | 15 |
| | 29 | 250 | 294 | 84 | 98 | 15 |
| | 30 | 742 | 786 | 248 | 262 | 15 |
| | 31 | 262 | 306 | 88 | 102 | 15 |
| | 32 | 751 | 795 | 251 | 265 | 15 |
| | 33 | 877 | 921 | 293 | 307 | 15 |
| | 34 | 772 | 816 | 258 | 272 | 15 |
| | 35 | 664 | 708 | 222 | 236 | 15 |
| DRB1*0103 | 36 | 316 | 360 | 106 | 120 | 15 |
| | 37 | 625 | 669 | 209 | 223 | 15 |
| | 38 | 652 | 696 | 218 | 232 | 15 |
| | 39 | 1066 | 1110 | 356 | 370 | 15 |
| | 40 | 511 | 555 | 171 | 185 | 15 |
| | 41 | 529 | 573 | 177 | 191 | 15 |
| | 42 | 676 | 720 | 226 | 240 | 15 |
| | 43 | 250 | 294 | 84 | 98 | 15 |
| | 44 | 961 | 1005 | 321 | 335 | 15 |
| DRB1*0104 | 45 | 523 | 567 | 175 | 189 | 15 |
| | 46 | 529 | 573 | 177 | 191 | 15 |
| | 47 | 889 | 933 | 297 | 311 | 15 |
| | 48 | 652 | 696 | 218 | 232 | 15 |
| | 49 | 625 | 669 | 209 | 223 | 15 |
| | 50 | 250 | 294 | 84 | 98 | 15 |
| | 51 | 511 | 555 | 171 | 185 | 15 |
| | 52 | 1075 | 1119 | 359 | 373 | 15 |
| | 53 | 751 | 795 | 251 | 265 | 15 |
| | 54 | 1066 | 1110 | 356 | 370 | 15 |
| | 55 | 742 | 786 | 248 | 262 | 15 |
| | 56 | 262 | 306 | 88 | 102 | 15 |
| | 57 | 316 | 360 | 106 | 120 | 15 |
| DRB1*0105 | 58 | 523 | 567 | 175 | 189 | 15 |
| | 59 | 625 | 669 | 209 | 223 | 15 |
| | 60 | 511 | 555 | 171 | 185 | 15 |
| | 61 | 316 | 360 | 106 | 120 | 15 |
| | 62 | 889 | 933 | 297 | 311 | 15 |
| | 63 | 652 | 696 | 218 | 232 | 15 |
| | 64 | 1066 | 1110 | 356 | 370 | 15 |
| | 65 | 751 | 795 | 251 | 265 | 15 |
| | 66 | 961 | 1005 | 321 | 335 | 15 |
| | 67 | 250 | 294 | 84 | 98 | 15 |
| | 68 | 535 | 579 | 179 | 193 | 15 |
| | 69 | 742 | 786 | 248 | 262 | 15 |
| | 70 | 1018 | 1062 | 340 | 354 | 15 |
| | 71 | 871 | 915 | 291 | 305 | 15 |
| | 72 | 610 | 654 | 204 | 218 | 15 |
| | 73 | 676 | 720 | 226 | 240 | 15 |
| | 74 | 664 | 708 | 222 | 236 | 15 |

TABLE 4-continued

NetMHCIIPAN predicted T cell epitopes in Api m 3 (only strong binders)

| Allele | Peptide No. | Start No.* nucleic acid | End No.* Nucleic acid | Start No.** amino acid | End No.** amino acid | Length amino acid |
|---|---|---|---|---|---|---|
| | 75 | 190 | 234 | 64 | 78 | 15 |
| | 76 | 772 | 816 | 258 | 272 | 15 |
| DRB1*0106 | 77 | 529 | 573 | 177 | 191 | 15 |
| | 78 | 652 | 696 | 218 | 232 | 15 |
| | 79 | 316 | 360 | 106 | 120 | 15 |
| | 80 | 523 | 567 | 175 | 189 | 15 |
| | 81 | 511 | 555 | 171 | 185 | 15 |
| | 82 | 889 | 933 | 297 | 311 | 15 |
| | 83 | 625 | 669 | 209 | 223 | 15 |
| | 84 | 742 | 786 | 248 | 262 | 15 |
| | 85 | 1066 | 1110 | 356 | 370 | 15 |
| | 86 | 250 | 294 | 84 | 98 | 15 |
| | 87 | 1075 | 1119 | 359 | 373 | 15 |
| | 88 | 880 | 924 | 294 | 308 | 15 |
| | 89 | 262 | 306 | 88 | 102 | 15 |
| DRB1*0107 | 90 | 523 | 567 | 175 | 189 | 15 |
| | 91 | 625 | 669 | 209 | 223 | 15 |
| | 92 | 511 | 555 | 171 | 185 | 15 |
| | 93 | 316 | 360 | 106 | 120 | 15 |
| | 94 | 889 | 933 | 297 | 311 | 15 |
| | 95 | 652 | 696 | 218 | 232 | 15 |
| | 96 | 1066 | 1110 | 356 | 370 | 15 |
| | 97 | 751 | 795 | 251 | 265 | 15 |
| | 98 | 961 | 1005 | 321 | 335 | 15 |
| | 99 | 250 | 294 | 84 | 98 | 15 |
| | 100 | 535 | 579 | 179 | 193 | 15 |
| | 101 | 742 | 786 | 248 | 262 | 15 |
| | 102 | 1018 | 1062 | 340 | 354 | 15 |
| | 103 | 871 | 915 | 291 | 305 | 15 |
| | 104 | 610 | 654 | 204 | 218 | 15 |
| | 105 | 676 | 720 | 226 | 240 | 15 |
| | 106 | 664 | 708 | 222 | 236 | 15 |
| | 107 | 190 | 234 | 64 | 78 | 15 |
| | 108 | 772 | 816 | 258 | 272 | 15 |
| DRB1*0108 | 109 | 523 | 567 | 175 | 189 | 15 |
| | 110 | 625 | 669 | 209 | 223 | 15 |
| | 111 | 511 | 555 | 171 | 185 | 15 |
| | 112 | 316 | 360 | 106 | 120 | 15 |
| | 113 | 889 | 933 | 297 | 311 | 15 |
| | 114 | 652 | 696 | 218 | 232 | 15 |
| | 115 | 1066 | 1110 | 356 | 370 | 15 |
| | 116 | 751 | 795 | 251 | 265 | 15 |
| | 117 | 961 | 1005 | 321 | 335 | 15 |
| | 118 | 250 | 294 | 84 | 98 | 15 |
| | 119 | 535 | 579 | 179 | 193 | 15 |
| | 120 | 742 | 786 | 248 | 262 | 15 |
| | 121 | 1018 | 1062 | 340 | 354 | 15 |
| | 122 | 871 | 915 | 291 | 305 | 15 |
| | 123 | 610 | 654 | 204 | 218 | 15 |
| | 124 | 676 | 720 | 226 | 240 | 15 |
| | 125 | 664 | 708 | 222 | 236 | 15 |
| | 126 | 190 | 234 | 64 | 78 | 15 |
| | 127 | 772 | 816 | 258 | 272 | 15 |
| DRB1*0109 | 128 | 523 | 567 | 175 | 189 | 15 |
| | 129 | 316 | 360 | 106 | 120 | 15 |
| | 130 | 511 | 555 | 171 | 185 | 15 |
| | 131 | 625 | 669 | 209 | 223 | 15 |
| | 132 | 529 | 573 | 177 | 191 | 15 |
| | 133 | 652 | 696 | 218 | 232 | 15 |
| | 134 | 532 | 576 | 178 | 192 | 15 |
| | 135 | 889 | 933 | 297 | 311 | 15 |
| | 136 | 1066 | 1110 | 356 | 370 | 15 |
| | 137 | 535 | 579 | 179 | 193 | 15 |
| | 138 | 751 | 795 | 251 | 265 | 15 |
| | 139 | 1018 | 1062 | 340 | 354 | 15 |
| | 140 | 742 | 786 | 248 | 262 | 15 |
| | 141 | 250 | 294 | 84 | 98 | 15 |
| | 142 | 961 | 1005 | 321 | 335 | 15 |
| | 143 | 610 | 654 | 204 | 218 | 15 |
| | 144 | 676 | 720 | 226 | 240 | 15 |
| | 145 | 871 | 915 | 291 | 305 | 15 |
| | 146 | 664 | 708 | 222 | 236 | 15 |
| DRB1*0110 | 147 | 523 | 567 | 175 | 189 | 15 |
| | 148 | 625 | 669 | 209 | 223 | 15 |
| | 149 | 511 | 555 | 171 | 185 | 15 |

TABLE 4-continued

NetMHCIIPAN predicted T cell epitopes in Api m 3 (only strong binders)

| Allele | Peptide No. | Start No.* nucleic acid | End No.* Nucleic acid | Start No.** amino acid | End No.** amino acid | Length amino acid |
|---|---|---|---|---|---|---|
| | 150 | 316 | 360 | 106 | 120 | 15 |
| | 151 | 889 | 933 | 297 | 311 | 15 |
| | 152 | 619 | 663 | 207 | 221 | 15 |
| | 153 | 652 | 696 | 218 | 232 | 15 |
| | 154 | 751 | 795 | 251 | 265 | 15 |
| | 155 | 1066 | 1110 | 356 | 370 | 15 |
| | 156 | 1018 | 1062 | 340 | 354 | 15 |
| | 157 | 535 | 579 | 179 | 193 | 15 |
| | 158 | 961 | 1005 | 321 | 335 | 15 |
| | 159 | 250 | 294 | 84 | 98 | 15 |
| | 160 | 676 | 720 | 226 | 240 | 15 |
| | 161 | 871 | 915 | 291 | 305 | 15 |
| | 162 | 193 | 237 | 65 | 79 | 15 |
| | 163 | 739 | 783 | 247 | 261 | 15 |
| | 164 | 190 | 234 | 64 | 78 | 15 |
| | 165 | 664 | 708 | 222 | 236 | 15 |
| DRB1*0111 | 166 | 523 | 567 | 175 | 189 | 15 |
| | 167 | 889 | 933 | 297 | 311 | 15 |
| | 168 | 625 | 669 | 209 | 223 | 15 |
| | 169 | 751 | 795 | 251 | 265 | 15 |
| | 170 | 511 | 555 | 171 | 185 | 15 |
| | 171 | 652 | 696 | 218 | 232 | 15 |
| | 172 | 535 | 579 | 179 | 193 | 15 |
| | 173 | 316 | 360 | 106 | 120 | 15 |
| | 174 | 1018 | 1062 | 340 | 354 | 15 |
| | 175 | 1066 | 1110 | 356 | 370 | 15 |
| | 176 | 250 | 294 | 84 | 98 | 15 |
| | 177 | 961 | 1005 | 321 | 335 | 15 |
| | 178 | 610 | 654 | 204 | 218 | 15 |
| | 179 | 190 | 234 | 64 | 78 | 15 |
| | 180 | 676 | 720 | 226 | 240 | 15 |
| | 181 | 871 | 915 | 291 | 305 | 15 |
| | 182 | 193 | 237 | 65 | 79 | 15 |
| | 183 | 91 | 135 | 31 | 45 | 15 |
| | 184 | 1075 | 1119 | 359 | 373 | 15 |
| DRB1*0112 | 185 | 523 | 567 | 175 | 189 | 15 |
| | 186 | 625 | 669 | 209 | 223 | 15 |
| | 187 | 511 | 555 | 171 | 185 | 15 |
| | 188 | 316 | 360 | 106 | 120 | 15 |
| | 189 | 889 | 933 | 297 | 311 | 15 |
| | 190 | 652 | 696 | 218 | 232 | 15 |
| | 191 | 1066 | 1110 | 356 | 370 | 15 |
| | 192 | 751 | 795 | 251 | 265 | 15 |
| | 193 | 961 | 1005 | 321 | 335 | 15 |
| | 194 | 250 | 294 | 84 | 98 | 15 |
| | 195 | 535 | 579 | 179 | 193 | 15 |
| | 196 | 742 | 786 | 248 | 262 | 15 |
| | 197 | 1018 | 1062 | 340 | 354 | 15 |
| | 198 | 871 | 915 | 291 | 305 | 15 |
| | 199 | 610 | 654 | 204 | 218 | 15 |
| | 200 | 676 | 720 | 226 | 240 | 15 |
| | 201 | 664 | 708 | 222 | 236 | 15 |
| | 202 | 190 | 234 | 64 | 78 | 15 |
| | 203 | 772 | 816 | 258 | 272 | 15 |
| DRB1*0113 | 204 | 523 | 567 | 175 | 189 | 15 |
| | 205 | 889 | 933 | 297 | 311 | 15 |
| | 206 | 625 | 669 | 209 | 223 | 15 |
| | 207 | 619 | 663 | 207 | 221 | 15 |
| | 208 | 751 | 795 | 251 | 265 | 15 |
| | 209 | 511 | 555 | 171 | 185 | 15 |
| | 210 | 316 | 360 | 106 | 120 | 15 |
| | 211 | 535 | 579 | 179 | 193 | 15 |
| | 212 | 652 | 696 | 218 | 232 | 15 |
| | 213 | 1066 | 1110 | 356 | 370 | 15 |
| | 214 | 742 | 786 | 248 | 262 | 15 |
| | 215 | 250 | 294 | 84 | 98 | 15 |
| | 216 | 1075 | 1119 | 359 | 373 | 15 |
| | 217 | 190 | 234 | 64 | 78 | 15 |
| | 218 | 676 | 720 | 226 | 240 | 15 |
| | 219 | 661 | 705 | 221 | 235 | 15 |
| | 220 | 955 | 999 | 319 | 333 | 15 |
| | 221 | 961 | 1005 | 321 | 335 | 15 |
| | 222 | 1021 | 1065 | 341 | 355 | 15 |
| | 223 | 871 | 915 | 291 | 305 | 15 |
| | 224 | 208 | 252 | 70 | 84 | 15 |

TABLE 4-continued

NetMHCIIPAN predicted T cell epitopes in Api m 3 (only strong binders)

| Allele | Peptide No. | Start No.* nucleic acid | End No.* Nucleic acid | Start No.** amino acid | End No.** amino acid | Length amino acid |
|---|---|---|---|---|---|---|
| | 225 | 847 | 891 | 283 | 297 | 15 |
| | 226 | 91 | 135 | 31 | 45 | 15 |
| DRB1*0114 | 227 | 523 | 567 | 175 | 189 | 15 |
| | 228 | 625 | 669 | 209 | 223 | 15 |
| | 229 | 316 | 360 | 106 | 120 | 15 |
| | 230 | 511 | 555 | 171 | 185 | 15 |
| | 231 | 652 | 696 | 218 | 232 | 15 |
| | 232 | 751 | 795 | 251 | 265 | 15 |
| | 233 | 889 | 933 | 297 | 311 | 15 |
| | 234 | 1018 | 1062 | 340 | 354 | 15 |
| | 235 | 535 | 579 | 179 | 193 | 15 |
| | 236 | 1066 | 1110 | 356 | 370 | 15 |
| | 237 | 961 | 1005 | 321 | 335 | 15 |
| | 238 | 250 | 294 | 84 | 98 | 15 |
| | 239 | 1075 | 1119 | 359 | 373 | 15 |
| | 240 | 871 | 915 | 291 | 305 | 15 |
| | 241 | 739 | 783 | 247 | 261 | 15 |
| | 242 | 823 | 867 | 275 | 289 | 15 |
| | 243 | 610 | 654 | 204 | 218 | 15 |
| | 244 | 193 | 237 | 65 | 79 | 15 |
| | 245 | 676 | 720 | 226 | 240 | 15 |
| | 246 | 385 | 429 | 129 | 143 | 15 |
| | 247 | 772 | 816 | 258 | 272 | 15 |
| DRB1*0115 | 248 | 316 | 360 | 106 | 120 | 15 |
| | 249 | 625 | 669 | 209 | 223 | 15 |
| | 250 | 652 | 696 | 218 | 232 | 15 |
| | 251 | 511 | 555 | 171 | 185 | 15 |
| | 252 | 529 | 573 | 177 | 191 | 15 |
| | 253 | 523 | 567 | 175 | 189 | 15 |
| | 254 | 1066 | 1110 | 356 | 370 | 15 |
| | 255 | 1018 | 1062 | 340 | 354 | 15 |
| | 256 | 751 | 795 | 251 | 265 | 15 |
| | 257 | 250 | 294 | 84 | 98 | 15 |
| | 258 | 742 | 786 | 248 | 262 | 15 |
| | 259 | 889 | 933 | 297 | 311 | 15 |
| | 260 | 676 | 720 | 226 | 240 | 15 |
| | 261 | 961 | 1005 | 321 | 335 | 15 |
| | 262 | 610 | 654 | 204 | 218 | 15 |
| DRB1*0116 | 263 | 625 | 669 | 209 | 223 | 15 |
| | 264 | 529 | 573 | 177 | 191 | 15 |
| | 265 | 523 | 567 | 175 | 189 | 15 |
| | 266 | 1021 | 1065 | 341 | 355 | 15 |
| | 267 | 751 | 795 | 251 | 265 | 15 |
| | 268 | 889 | 933 | 297 | 311 | 15 |
| DRB1*0117 | 269 | 523 | 567 | 175 | 189 | 15 |
| | 270 | 625 | 669 | 209 | 223 | 15 |
| | 271 | 511 | 555 | 171 | 185 | 15 |
| | 272 | 316 | 360 | 106 | 120 | 15 |
| | 273 | 652 | 696 | 218 | 232 | 15 |
| | 274 | 889 | 933 | 297 | 311 | 15 |
| | 275 | 751 | 795 | 251 | 265 | 15 |
| | 276 | 1066 | 1110 | 356 | 370 | 15 |
| | 277 | 1018 | 1062 | 340 | 354 | 15 |
| | 278 | 250 | 294 | 84 | 98 | 15 |
| | 279 | 535 | 579 | 179 | 193 | 15 |
| | 280 | 961 | 1005 | 321 | 335 | 15 |
| | 281 | 610 | 654 | 204 | 218 | 15 |
| | 282 | 871 | 915 | 291 | 305 | 15 |
| | 283 | 739 | 783 | 247 | 261 | 15 |
| | 284 | 193 | 237 | 65 | 79 | 15 |
| | 285 | 676 | 720 | 226 | 240 | 15 |
| | 286 | 91 | 135 | 31 | 45 | 15 |
| | 287 | 550 | 594 | 184 | 198 | 15 |
| DRB1*0118 | 288 | 523 | 567 | 175 | 189 | 15 |
| | 289 | 511 | 555 | 171 | 185 | 15 |
| | 290 | 652 | 696 | 218 | 232 | 15 |
| | 291 | 316 | 360 | 106 | 120 | 15 |
| | 292 | 625 | 669 | 209 | 223 | 15 |
| | 293 | 889 | 933 | 297 | 311 | 15 |
| | 294 | 1066 | 1110 | 356 | 370 | 15 |
| | 295 | 619 | 663 | 207 | 221 | 15 |
| | 296 | 742 | 786 | 248 | 262 | 15 |
| | 297 | 250 | 294 | 84 | 98 | 15 |
| | 298 | 1075 | 1119 | 359 | 373 | 15 |
| | 299 | 961 | 1005 | 321 | 335 | 15 |

TABLE 4-continued

NetMHCIIPAN predicted T cell epitopes in Api m 3 (only strong binders)

| Allele | Peptide No. | Start No.* nucleic acid | End No.* Nucleic acid | Start No.** amino acid | End No.** amino acid | Length amino acid |
|---|---|---|---|---|---|---|
|  | 300 | 751 | 795 | 251 | 265 | 15 |
|  | 301 | 535 | 579 | 179 | 193 | 15 |
|  | 302 | 871 | 915 | 291 | 305 | 15 |
|  | 303 | 664 | 708 | 222 | 236 | 15 |
|  | 304 | 1018 | 1062 | 340 | 354 | 15 |
|  | 305 | 676 | 720 | 226 | 240 | 15 |
| DRB1*0119 | 306 | 523 | 567 | 175 | 189 | 15 |
|  | 307 | 625 | 669 | 209 | 223 | 15 |
|  | 308 | 511 | 555 | 171 | 185 | 15 |
|  | 309 | 316 | 360 | 106 | 120 | 15 |
|  | 310 | 889 | 933 | 297 | 311 | 15 |
|  | 311 | 652 | 696 | 218 | 232 | 15 |
|  | 312 | 1066 | 1110 | 356 | 370 | 15 |
|  | 313 | 751 | 795 | 251 | 265 | 15 |
|  | 314 | 961 | 1005 | 321 | 335 | 15 |
|  | 315 | 250 | 294 | 84 | 98 | 15 |
|  | 316 | 535 | 579 | 179 | 193 | 15 |
|  | 317 | 742 | 786 | 248 | 262 | 15 |
|  | 318 | 1018 | 1062 | 340 | 354 | 15 |
|  | 319 | 871 | 915 | 291 | 305 | 15 |
|  | 320 | 610 | 654 | 204 | 218 | 15 |
|  | 321 | 676 | 720 | 226 | 240 | 15 |
|  | 322 | 664 | 708 | 222 | 236 | 15 |
|  | 323 | 190 | 234 | 64 | 78 | 15 |
|  | 324 | 772 | 816 | 258 | 272 | 15 |

*Numbering according to SEQ ID NO: 1
**Numbering according to SEQ ID NO: 2

TABLE 5

Calculation of putative surface epitopes per protein size ratio

| Antigen | Size | Surface ($Å^2$) | Surface epitopes* | Surface epitopes/kDa |
|---|---|---|---|---|
| Amb t 5 | 4.3 kDa | 2438.3 | 2.57 | 0.6 |
| Api m 1 | 16-20 kDa | 7606.4 | 8.0 | 0.4 |
| Api m 2 | 43 kDa | 15905.5 | 16.74 | 0.39 |
| Api m 4 | 3 kDa | 3885.7 | 4.09 | 1.36 |
| Ara t 8 | 14.2 kDa | 7080.1 | 7.45 | 0.52 |
| Asp f 1 | 16.8 kDa | 16037.6 | 16.88 | 1.0 |
| Asp f 6 | 23.3 kDa | 8793.2 | 9.26 | 0.4 |
| Bet v 1 | 17.4 kDa | 5215.3 | 5.49 | 0.32 |
| Bet v 2 | 14.3 kDa | 6493.9 | 6.84 | 0.48 |
| Bos d 4 | 14.2 kDa | 7246.9 | 7.63 | 0.54 |
| Bos d 5 | 18.2 kDa | 9546.5 | 10.05 | 0.55 |
| Bos d 5 | 18.2 kDa | 9618.4 | 10.12 | 0.56 |
| Der f2 | 15.8 kDa | 7785.2 | 8.19 | 0.52 |
| Der p2 | 16 kDa | 7588.8 | 7.99 | 0.5 |
| Equ c 1 | 20 kDa | 8907.4 | 9.38 | 0.47 |
| Gal d 3 | 75.8 kDa | 15952.9 | 16.79 | 0.22 |
| Gal d 4 | 16.2 kDa | 6951.3 | 7.32 | 0.45 |
| Hev b 8 | 14 kDa | 11982 | 12.61 | 0.9 |
| Mus m 1 | 18.7 kDa | 8943.5 | 9.41 | 0.5 |
| Phl p 1 | 26.1 kDa | 12145.6 | 12.78 | 0.49 |
| Phl p 2 | 10.8 kDa | 6099.5 | 6.42 | 0.59 |
| Phl p 6 | 11.8 kDa | 5429.5 | 5.72 | 0.48 |
| Pru av 1 | 17.7 kDa | 9742.8 | 10.26 | 0.58 |
| Ves v 5 | 25.8 kDa | 11657.1 | 12.27 | 0.47 |
| Zea m14 | 11.7 kDa | 5099.5 | 5.37 | 0.46 |
| Average value |  |  |  | 0.55 +/− 0.23 |

*Estimated IgE epitope area: 950 $Å^2$

TABLE 6

Calculation of the average number of IgE epitopes on allergens

| Antigen | Protein | Organism | Common | PDB code | Size (kDa) | Surface ($Å^2$) | Size/ Surface | Possible B-cell epitopes | Identified IgE binding peptides |
|---|---|---|---|---|---|---|---|---|---|
| Alt a 1 | — | *Alt. alternata* | Fungi | — | 15.2 | — | — | — | 2 |
| Ara h 1 | Vicilin | *Arachis hypogaea* | Peanut | — | 67.7 | — | — | — | 21 |
| Ara h 2 | Conglutin | *Arachis hypogaea* | Peanut | — | 17.5 | — | — | — | 10 |
| Asp f 1 | Mitogillin | *Asp. fumigatus* | Fungi | 1AQZ | 16.8 | 16037.6 | 1.0 | 16-17 | 13 |
| Asp f 2 | — | *Asp. fumigatus* | Fungi | — | 31.2 | — | — | — | 9 |
| Asp f 3 | Peroximal protein | *Asp. fumigatus* | Fungi | — | 18.4 | — | — | — | 7 |

TABLE 6-continued

Calculation of the average number of IgE epitopes on allergens

| Antigen | Protein | Organism | Common | PDB code | Size (kDa) | Surface (Å²) | Size/ Surface | Possible B-cell epitopes | Identified IgE binding peptides |
|---|---|---|---|---|---|---|---|---|---|
| Asp f 13 | Oryzin | *Asp. fumigatus* | Fungi | — | 28.7 | — | — | — | 5 |
| Bet v 1 | PR10 | *Betulla verrucosa* | Birch | 1BV1 | 17.4 | 5215.3 | 3.3 | 5-6 | |
| Bet v 2 | Profilin | *Betulla verrucosa* | Birch | 1CQA | 14.3 | 6493.9 | 2.2 | 6-7 | 3 |
| Bos d 5 | b-Lactoglobulin | *Bos domesticus* | Cow | 1B8E | 18.2 | 9546.5 | 1.9 | 9-10 | 7 |
| Bos d 5 | b-Lactoglobulin | *Bos domesticus* | Cow | 1QG5 | 18.2 | 9618.4 | 1.9 | 9-10 | 7 |
| Cry j 2 | Pectinase | *Cryp. japonica* | Sugi | — | 42.2 | — | — | — | 4 |
| Gal d 1 | Ovomucoid | *Gallus domesticus* | Chicken | — | 20.1 | — | — | — | 9 (8 IgG) |
| Hev b 1 | Elongaton factor | *Hevea brasiliensis* | Latex | — | 14.6 | — | — | — | 8 |
| Hev b 3 | SRPP | *Hevea brasiliensis* | Latex | — | 22.3 | — | — | — | 11 |
| Hev b 5 | — | *Hevea brasiliensis* | Latex | — | 15.9 | — | — | — | 11 |
| Jun a 1 | Pectate lyase | *Juniperus ashei* | Cedar | — | 37.6 | — | — | — | 4 |
| Jun a 3 | — | *Juniperus ashei* | Cedar | — | 21 | — | — | — | 5 |
| Par j 1 | Lipid transfer prot. 1 | *Parietaria judaica* | Weed | — | 15 | — | — | — | 5 |
| Par j 2 | Lipid transfer prot. 2 | *Parietaria judaica* | Weed | — | 11.3 | — | — | — | 8 |
| Pen n18 | Serine protease | *Pen. notatum* | Fungi | — | 52.4 | — | — | — | 9 |

The invention claimed is:

1. A recombinant polypeptide capable of binding to an IgE from subjects allergic to venom of an insect from the order Hymenoptera, wherein said polypeptide is expressed in *E. Coli*, High5 or Sf9 cells and has the amino acid sequence of SEQ ID NO: 2.

2. The polypeptide of claim 1, which is encoded by a naturally occurring nucleic acid of an insect from the order Hymenoptera.

3. The polypeptide of claim 1, wherein one or more glycosylation sites of the sequence Asn-Xaa-Ser/Thr has been mutated to a non-glycosylation site.

4. The polypeptide of claim 1, wherein the insect is a bee from the genus *Apis*.

5. The polypeptide of claim 4, wherein the bee is *Apis mellifera*.

6. The polypeptide of claim 1 having acid phosphatase activity.

7. The polypeptide of claim 1, wherein the polypeptide is non-glycosylated.

8. The polypeptide of claim 1, wherein the polypeptide is expressed in bacterial or insect cells.

9. The polypeptide of claim 1, wherein the glycosylation pattern of said polypeptide differs from the glycosylation pattern of natural acid phosphatase isolated from bee venom.

10. A pharmaceutical or diagnostic composition comprising the polypeptide of claim 1.

11. The composition of claim 10, further comprising a suitable adjuvant or excipient or further polypeptides from the venom of an insect from the order Hymenoptera.

12. A polypeptide selected from the group consisting of polypeptides consisting of amino acids 1 to 25, 146 to 152, 159 to 164, 168 to 184, 224 to 231, and 277 to 361 of the polypeptide of SEQ ID NO: 2.

13. A method of treating a subject allergic to the venom of an insect from the order Hymenoptera, comprising the step of administering the polypeptide of claim 1 to said subject.

14. A method of diagnosing an allergy to the venom of an insect from the order Hymenoptera, comprising the steps of
   a) in vitro contacting a blood sample from a subject with the polypeptide of claim 1, and
   b) detecting binding of IgE antibodies to the polypeptide, wherein specific binding can be determined by comparing with a specificity control, e.g., with an unrelated antibody; and wherein detecting IgE antibodies binding to the polypeptide indicates said allergy.

* * * * *

SEQUENCE LISTING

```
<160> NUMBER OF SEQ ID NOS: 41

<210> SEQ ID NO 1
<211> LENGTH: 1122
<212> TYPE: DNA
<213> ORGANISM: Apis mellifera

<400> SEQUENCE: 1
gaacttaaac aaataaatgt gatattccgg cacggcgata ggatacccga tgagaaaaac     60
gaaatgtatc cgaaagatcc ttatttgtat tatgattttt atccactgga gcgtggcgaa    120
ttgactaact caggtaaaat gcgagaatat caattggggc aattcttgag agagagatat    180
ggtgactttt tgggagacat ttacacgaaa gaatccgtct cggctctcag ctcgttctac    240
gataggacga aaatgtctct gcaactcgta ctcgcggcgc tctatccgcc aaataaattg    300
caacaatgga acgaagatct gaactggcaa ccgatcgcca cgaaatattt gcgccgctac    360
gaggacaata tcttttttgcc agaagattgt ttgttattta ccatcgaact tgatagagta    420
ttggaatcac cgcgtggaaa gtatgaattc tcgaaatatg acaaattgaa gaaaaaattg    480
gaagaatgga ccggaaaaaa tatcactacg ccatgggatt attattacat atatcataca    540
ctggtggctg aacaatcgta cggtcttact ctgccatctt ggacaaataa tatattcccg    600
agaggagaat tgttcgatgc gacggtattt acgtacaaca taaccaattc gactcctttg    660
ttgaaaaaac tttatggagg tccgcttctt cgaatattca ccaagcatat gttagacgtg    720
gtatcgggta cgcaaaagaa aaagcgaaag atatacttgt tcagtggaca tgaaagtaat    780
```

```
atcgcctctg tgttgcacgc tcttcaactt tattatcctc acgttcctga atattccagt    840
tctattataa tggagcttca caatatcgaa ggcactcact acgtaaagat cgtttactac    900
ttgggtatcc cgtctgaagc gagagaactt caattacccg gctgcgaggt actttgccct    960
ttgtacaaat atttcaatt gatagagaac gtgataccat cgaacgaaga gttgatctgc   1020
gataaaagat tcgtcgacga atcggcaaac aatttgtcga tcgaagaatt agatttcgtg   1080
aaattgaacc taataaggat agcgggtact gagaataagt aa                     1122
```

<210> SEQ ID NO 2
<211> LENGTH: 373
<212> TYPE: PRT
<213> ORGANISM: Apis mellifera

<400> SEQUENCE: 2

```
Glu Leu Lys Gln Ile Asn Val Ile Phe Arg His Gly Asp Arg Ile Pro
1               5                   10                  15

Asp Glu Lys Asn Glu Met Tyr Pro Lys Asp Pro Tyr Leu Tyr Tyr Asp
                20                  25                  30

Phe Tyr Pro Leu Glu Arg Gly Glu Leu Thr Asn Ser Gly Lys Met Arg
            35                  40                  45

Glu Tyr Gln Leu Gly Gln Phe Leu Arg Glu Arg Tyr Gly Asp Phe Leu
    50                  55                  60

Gly Asp Ile Tyr Thr Glu Glu Ser Val Ser Ala Leu Ser Ser Phe Tyr
65                  70                  75                  80

Asp Arg Thr Lys Met Ser Leu Gln Leu Val Leu Ala Ala Leu Tyr Pro
                85                  90                  95

Pro Asn Lys Leu Gln Gln Trp Asn Glu Asp Leu Asn Trp Gln Pro Ile
            100                 105                 110

Ala Thr Lys Tyr Leu Arg Arg Tyr Glu Asp Asn Ile Phe Leu Pro Glu
        115                 120                 125

Asp Cys Leu Leu Phe Thr Ile Glu Leu Asp Arg Val Leu Glu Ser Pro
    130                 135                 140

Arg Gly Lys Tyr Glu Phe Ser Lys Tyr Asp Lys Leu Lys Lys Lys Leu
145                 150                 155                 160

Glu Glu Trp Thr Gly Lys Asn Ile Thr Thr Pro Trp Asp Tyr Tyr Tyr
                165                 170                 175

Ile Tyr His Thr Leu Val Ala Glu Gln Ser Tyr Gly Leu Thr Leu Pro
            180                 185                 190

Ser Trp Thr Asn Asn Ile Phe Pro Arg Gly Glu Leu Phe Asp Ala Thr
        195                 200                 205

Val Phe Thr Tyr Asn Ile Thr Asn Ser Thr Pro Leu Leu Lys Lys Leu
    210                 215                 220

Tyr Gly Gly Pro Leu Leu Arg Ile Phe Thr Lys His Met Leu Asp Val
225                 230                 235                 240

Val Ser Gly Thr Gln Lys Lys Arg Lys Ile Tyr Leu Phe Ser Gly
                245                 250                 255

His Glu Ser Asn Ile Ala Ser Val Leu His Ala Leu Gln Leu Tyr Tyr
            260                 265                 270

Pro His Val Pro Glu Tyr Ser Ser Ile Ile Met Glu Leu His Asn
        275                 280                 285

Ile Glu Gly Thr His Tyr Val Lys Ile Val Tyr Tyr Leu Gly Ile Pro
    290                 295                 300

Ser Glu Ala Arg Glu Leu Gln Leu Pro Gly Cys Glu Val Leu Cys Pro
305                 310                 315                 320
```

```
Leu Tyr Lys Tyr Leu Gln Leu Ile Glu Asn Val Ile Pro Ser Asn Glu
            325                 330                 335

Glu Leu Ile Cys Asp Lys Arg Phe Val Asp Glu Ser Ala Asn Asn Leu
        340                 345                 350

Ser Ile Glu Glu Leu Asp Phe Val Lys Leu Asn Leu Ile Arg Ile Ala
    355                 360                 365

Gly Thr Glu Asn Lys
    370

<210> SEQ ID NO 3
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 3
gaacttaaac aaataaatgt g                                         21

<210> SEQ ID NO 4
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 4
aaccgcggtt acttacttat tctcagtacc cg                             32

<210> SEQ ID NO 5
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 5
gtaaaacgac ggccagtgcc aa                                        22

<210> SEQ ID NO 6
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 6
caggaaacag ctatgaccat ga                                        22

<210> SEQ ID NO 7
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 7
ggaaagcttt ccgccatggc gaaattctta gtc                            33

<210> SEQ ID NO 8
<211> LENGTH: 27
<212> TYPE: DNA
<213> ORGANISM: Artificial Sequence
<220> FEATURE:
```

-continued

<223> OTHER INFORMATION: oligonucleotide primer

<400> SEQUENCE: 8
cgggatcccg catagatgta agaaatg                                27

<210> SEQ ID NO 9
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 9
ctgaatagcg ccggatccga ccat                                   24

<210> SEQ ID NO 10
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 10
ccctctagac tcgagccaat gatg                                   24

<210> SEQ ID NO 11
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 11
gggatatccc ttccctcgat ccctctagac tc                          32

<210> SEQ ID NO 12
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 12
agaatttcat atgaaattct tagtcaacg                              29

<210> SEQ ID NO 13
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 13
aagagctctt acttacttat tctcag                                 26

<210> SEQ ID NO 14
<211> LENGTH: 15
<212> TYPE: PRT
<213> ORGANISM: Artificial Sequence
<220> FEATURE:
<223> OTHER INFORMATION: alanine added to N-terminal sequence

<400> SEQUENCE: 14

Ala Ala Gly Cys Thr Thr Ala Thr Gly Ala Ala Thr Thr Cys
1               5                   10                  15

```
<210> SEQ ID NO 15
<211> LENGTH: 24
<212> TYPE: PRT
<213> ORGANISM: Artificial Sequence
<220> FEATURE:
<223> OTHER INFORMATION: alanine added to N-terminal sequence

<400> SEQUENCE: 15

Ala Ala Gly Cys Thr Thr Thr Cys Cys Gly Cys Cys Ala Thr Gly Gly
1               5                   10                  15

Cys Gly Ala Ala Ala Thr Thr Cys
            20

<210> SEQ ID NO 16
<211> LENGTH: 4
<212> TYPE: PRT
<213> ORGANISM: Artificial Sequence
<220> FEATURE:
<223> OTHER INFORMATION: alanine added to N-terminal sequence

<400> SEQUENCE: 16

Met Ala Lys Phe
1

<210> SEQ ID NO 17
<211> LENGTH: 33
<212> TYPE: PRT
<213> ORGANISM: Homo sapiens

<400> SEQUENCE: 17

Glu Leu Lys Gln Ile Asn Val Ile Phe Arg His Gly Asp Arg Ile Pro
1               5                   10                  15

Asp Glu Lys Asn Glu Met Tyr Pro Lys Lys Leu Glu Glu Trp Thr Asp
            20                  25                  30

Lys

<210> SEQ ID NO 18
<211> LENGTH: 18
<212> TYPE: PRT
<213> ORGANISM: Homo sapiens

<400> SEQUENCE: 18

Phe Val Asp Glu Ser Ala Asn Asn Leu Ser Ile Glu Glu Ile Asp Phe
1               5                   10                  15

Val Lys

<210> SEQ ID NO 19
<211> LENGTH: 16
<212> TYPE: PRT
<213> ORGANISM: Homo sapiens

<400> SEQUENCE: 19

Leu Gln Gln Trp Asn Glu Asp Leu Asn Trp Gln Pro Ile Ala Thr Lys
1               5                   10                  15

<210> SEQ ID NO 20
<211> LENGTH: 8
<212> TYPE: PRT
<213> ORGANISM: Homo sapiens

<400> SEQUENCE: 20

Gly Lys Tyr Glu Phe Ser Lys Arg
1               5
```

```
<210> SEQ ID NO 21
<211> LENGTH: 9
<212> TYPE: PRT
<213> ORGANISM: Homo sapiens

<400> SEQUENCE: 21

Tyr Asn Ile Phe Ala Gly Thr Trp Lys
1               5

<210> SEQ ID NO 22
<211> LENGTH: 16
<212> TYPE: PRT
<213> ORGANISM: Homo sapiens

<400> SEQUENCE: 22

Leu Tyr Gly Gly Pro Leu Leu Arg Asp Asn Tyr Val Gly Asp Glu Arg
1               5                   10                  15

<210> SEQ ID NO 23
<211> LENGTH: 86
<212> TYPE: PRT
<213> ORGANISM: Homo sapiens

<400> SEQUENCE: 23

Asp Ile Thr Thr Pro Lys Asp Tyr Tyr Ile Tyr His Thr Leu Val
1               5                   10                  15

Ala Glu Asn Glu Tyr Ser Ser Cys Ile Ile Met Glu Tyr His Asn Ile
                20                  25                  30

Glu Gly Thr His Tyr Val Lys Ile Val Tyr Tyr Leu Gly Ile Pro Ser
            35                  40                  45

Glu Ala Arg Glu Leu Gln Leu Pro Gly Cys Val Leu Cys Pro Leu
        50                  55                  60

Glu Lys Tyr Leu Gln Leu Ile Glu Asn Val Ile Pro Ser Asn Glu Glu
65                  70                  75                  80

Leu Ile Cys Asp Lys Arg
                85

<210> SEQ ID NO 24
<211> LENGTH: 373
<212> TYPE: PRT
<213> ORGANISM: Apis mellifera

<400> SEQUENCE: 24

Glu Leu Lys Gln Ile Asn Val Ile Phe Arg His Gly Asp Arg Ile Pro
1               5                   10                  15

Asp Glu Lys Asn Glu Met Tyr Pro Lys Asp Pro Tyr Leu Tyr Tyr Asp
                20                  25                  30

Phe Tyr Pro Leu Glu Arg Gly Glu Leu Thr Asn Ser Gly Lys Met Arg
            35                  40                  45

Glu Tyr Gln Leu Gly Gln Phe Leu Arg Glu Arg Tyr Gly Asp Phe Leu
        50                  55                  60

Gly Asp Ile Tyr Thr Glu Glu Ser Val Ser Ala Leu Ser Ser Phe Tyr
65                  70                  75                  80

Asp Arg Thr Lys Met Ser Leu Gln Leu Val Leu Ala Ala Leu Tyr Pro
                85                  90                  95

Pro Asn Lys Leu Gln Gln Trp Asn Glu Asp Leu Asn Trp Gln Pro Ile
            100                 105                 110

Ala Thr Lys Tyr Leu Arg Arg Tyr Glu Asp Asn Ile Phe Leu Pro Glu
```

```
            115                 120                 125
Asp Cys Leu Leu Phe Thr Ile Glu Leu Asp Arg Val Leu Glu Ser Pro
    130                 135                 140

Arg Gly Lys Tyr Glu Phe Ser Lys Tyr Asp Lys Leu Lys Lys Lys Leu
145                 150                 155                 160

Glu Glu Trp Thr Gly Lys Asn Ile Thr Thr Pro Trp Asp Tyr Tyr Tyr
                165                 170                 175

Ile Tyr His Thr Leu Val Ala Glu Gln Ser Tyr Gly Leu Thr Leu Pro
            180                 185                 190

Ser Trp Thr Asn Asn Ile Phe Pro Arg Gly Glu Leu Phe Asp Ala Thr
        195                 200                 205

Val Phe Thr Tyr Asn Ile Thr Asn Ser Thr Pro Leu Leu Lys Lys Leu
    210                 215                 220

Tyr Gly Gly Pro Leu Leu Arg Ile Phe Thr Lys His Met Leu Asp Val
225                 230                 235                 240

Val Ser Gly Thr Gln Lys Lys Arg Lys Ile Tyr Leu Phe Ser Gly
                245                 250                 255

His Glu Ser Asn Ile Ala Ser Val Leu His Ala Leu Gln Leu Tyr Tyr
            260                 265                 270

Pro His Val Pro Glu Tyr Ser Ser Ile Ile Met Glu Leu His Asn
        275                 280                 285

Ile Glu Gly Thr His Tyr Val Lys Ile Val Tyr Tyr Leu Gly Ile Pro
    290                 295                 300

Ser Glu Ala Arg Glu Leu Gln Leu Pro Gly Cys Glu Val Leu Cys Pro
305                 310                 315                 320

Leu Tyr Lys Tyr Leu Gln Leu Ile Glu Asn Val Ile Pro Ser Asn Glu
                325                 330                 335

Glu Leu Ile Cys Asp Lys Arg Phe Val Asp Glu Ser Ala Asn Asn Leu
            340                 345                 350

Ser Ile Glu Glu Leu Asp Phe Val Lys Leu Asn Leu Ile Arg Ile Ala
        355                 360                 365

Gly Thr Glu Asn Lys
    370

<210> SEQ ID NO 25
<211> LENGTH: 392
<212> TYPE: PRT
<213> ORGANISM: Drosophila melanogaster

<400> SEQUENCE: 25

Gln Leu Lys Phe Val His Val Ile Tyr Arg His Gly Asp Arg Thr Pro
1               5                   10                  15

Val Asp Pro Tyr Pro Thr Asp Pro Trp Gly Asp Arg Lys Phe Trp Pro
            20                  25                  30

Thr Gly Trp Gly Asp Leu Thr Asn Leu Gly Lys Gln Glu His Tyr Asp
        35                  40                  45

Leu Gly Lys Trp Leu Arg Asn Arg Tyr Ser Asn Leu Leu Pro Pro Ile
    50                  55                  60

Tyr Ser Asn Glu Asn Ile Tyr Val Gln Ser Thr Asp Val Asp Arg Thr
65                  70                  75                  80

Leu Met Ser Ala Gln Ser Asn Leu Ala Gly Leu Tyr Glu Pro Gln Gly
                85                  90                  95

Glu Asp Ile Trp Asn Thr Asp Ile Asn Trp Gln Pro Ile Pro Ile His
            100                 105                 110
```

Thr Ser Pro Glu Arg Glu Asp Pro Ile Leu Ala Ala Lys Ala Pro Cys
            115                 120                 125

Pro Ala Tyr Asp Tyr Glu Leu Ala Ser Leu Ser Ser Pro Glu Phe
        130                 135                 140

Lys Ala Leu Thr Glu Lys His Arg Asn Leu Phe Ala Tyr Leu Ser Glu
145                 150                 155                 160

Lys Gly Gly Arg Pro Val Lys Thr Phe Ile Asp Ala Gln Tyr Leu Asn
                165                 170                 175

Asn Thr Leu Phe Ile Glu Asn Leu Tyr Asn Met Thr Leu Pro Lys Trp
            180                 185                 190

Thr Lys Lys Val Tyr Gly Arg Glu Leu Thr Tyr Val Ser Asn Phe
        195                 200                 205

Ala Phe Ala Ile Ser Ser Tyr Thr Arg Lys Leu Ala Arg Leu Lys Ala
210                 215                 220

Gly Pro Leu Leu Lys Asp Ile Phe Gln Arg Phe Lys Glu Lys Ser Ser
225                 230                 235                 240

Gly Ser Leu Lys Pro Asp Arg Ser Met Trp Val Tyr Ser Ala His Asp
                245                 250                 255

Thr Thr Val Ala Ser Val Leu Asn Ala Leu Lys Leu Phe Glu Leu His
            260                 265                 270

Ser Pro Pro Tyr Thr Ala Cys Ile Met Met Glu Leu Arg Val Asp Glu
        275                 280                 285

Thr Asn Thr Pro Leu Val Ser Ile Phe Tyr Lys Asn Thr Thr Ala Glu
290                 295                 300

Pro Leu Pro Leu Asp Ile Pro Gly Cys Gly Pro Ser Cys Pro Leu Thr
305                 310                 315                 320

Lys Leu Met Asn Ile Tyr Glu Asp Val Leu Pro Val Asp Trp Glu Arg
                325                 330                 335

Glu Cys Lys Leu Ser Thr Met Met Met Thr Tyr Glu Glu Ala Asn Leu
            340                 345                 350

Gly Thr Ala Thr Gly Ile Leu Ile Leu Ile Val Ile Ala Leu Leu Phe
        355                 360                 365

Ala Ser Tyr Gly Leu Met Ile Tyr Tyr Arg Arg Arg Asn Tyr Lys Leu
370                 375                 380

Tyr Ser Ser Tyr Ser Gln Met Ala
385                 390

<210> SEQ ID NO 26
<211> LENGTH: 392
<212> TYPE: PRT
<213> ORGANISM: Drosophila melanogaster

<400> SEQUENCE: 26

Gln Leu Lys Phe Val His Val Ile Tyr Arg His Gly Asp Arg Thr Pro
1               5                   10                  15

Val Asp Pro Tyr Pro Thr Asp Pro Trp Gly Asp Arg Lys Phe Trp Pro
            20                  25                  30

Thr Gly Trp Gly Asp Leu Thr Asn Leu Gly Lys Gln Glu His Tyr Asp
        35                  40                  45

Leu Gly Lys Trp Leu Arg Asn Arg Tyr Ser Asn Leu Leu Pro Pro Ile
    50                  55                  60

Tyr Ser Asn Glu Asn Ile Tyr Val Gln Ser Thr Asp Val Asp Arg Thr
65                  70                  75                  80

Leu Met Ser Ala Gln Ser Asn Leu Ala Gly Leu Tyr Glu Pro Gln Gly
                85                  90                  95

```
Glu Asp Ile Trp Asn Thr Asp Ile Asn Trp Gln Pro Ile Pro Ile His
                100                 105                 110

Thr Ser Pro Glu Arg Glu Asp Pro Ile Leu Ala Ala Lys Ala Pro Cys
            115                 120                 125

Pro Ala Tyr Asp Tyr Glu Leu Ala Ser Leu Glu Ser Ser Pro Glu Phe
        130                 135                 140

Lys Ala Leu Thr Glu Lys His Arg Asn Leu Phe Ala Tyr Leu Ser Glu
145                 150                 155                 160

Lys Gly Gly Arg Pro Val Lys Thr Phe Ile Asp Ala Gln Tyr Leu Asn
                165                 170                 175

Asn Thr Leu Phe Ile Glu Asn Leu Tyr Asn Met Thr Leu Pro Lys Trp
            180                 185                 190

Thr Lys Met Val Tyr Gly Arg Glu Glu Leu Thr Tyr Val Ser Asn Phe
        195                 200                 205

Ala Phe Ala Ile Ser Ser Tyr Thr Arg Lys Leu Ala Arg Leu Lys Ala
210                 215                 220

Gly Pro Leu Leu Lys Asp Ile Phe Gln Arg Phe Lys Glu Lys Ser Ser
225                 230                 235                 240

Gly Ser Leu Lys Pro Asp Arg Ser Met Trp Val Tyr Ser Ala His Asp
                245                 250                 255

Thr Thr Val Ala Ser Val Leu Asn Ala Leu Lys Leu Phe Glu Leu His
            260                 265                 270

Ser Pro Pro Tyr Thr Ala Cys Ile Met Met Glu Leu Arg Val Asp Glu
        275                 280                 285

Thr Asn Thr Pro Leu Val Ser Ile Phe Tyr Lys Asn Thr Thr Ala Glu
290                 295                 300

Pro Leu Pro Leu Asp Ile Pro Gly Cys Gly Pro Ser Cys Pro Leu Thr
305                 310                 315                 320

Lys Leu Met Asn Ile Tyr Glu Asp Val Leu Pro Val Asp Trp Glu Arg
                325                 330                 335

Glu Cys Lys Leu Ser Thr Met Met Met Thr Tyr Glu Glu Ala Asn Leu
            340                 345                 350

Gly Thr Ala Thr Gly Ile Leu Ile Leu Ile Val Ile Ala Leu Leu Phe
        355                 360                 365

Ala Ser Tyr Gly Leu Met Ile Tyr Tyr Arg Arg Arg Asn Tyr Lys Leu
370                 375                 380

Tyr Ser Ser Tyr Ser Gln Met Ala
385                 390

<210> SEQ ID NO 27
<211> LENGTH: 392
<212> TYPE: PRT
<213> ORGANISM: Drosophila subobscura

<400> SEQUENCE: 27

Glu Leu Lys Phe Ala His Val Ile Phe Arg His Gly Asp Arg Thr Pro
1               5                   10                  15

Val Asp Pro Tyr Pro Thr Asp Pro Trp Asn Asn Arg Lys Phe Trp Pro
            20                  25                  30

Thr Gly Trp Gly Gln Leu Thr Asn Leu Gly Lys Glu Gln His Tyr Glu
        35                  40                  45

Leu Gly Lys Trp Leu Arg Asn Arg Tyr Lys Ser Leu Leu Gly Ser Arg
50                  55                  60

Tyr Thr Asn Glu Asp Ile Phe Val Gln Ser Thr Asp Val Asp Arg Thr
```

```
                65                  70                  75                  80
Leu Met Ser Ala Gln Ser Asp Leu Ala Gly Leu Tyr Glu Pro Gln Gly
                    85                  90                  95

Asp Asp Ile Trp Asn Pro Arg Ile Asp Trp Gln Pro Val Pro Val His
                100                 105                 110

Thr Val Pro Glu Lys Asp Asp Ser Ile Leu Ala Ala Lys Ala Ser Cys
                115                 120                 125

Pro Ala Tyr Asp Tyr Glu Leu Ala Thr Leu Glu Ala Ser Ser Glu Phe
130                 135                 140

Gln Ala Leu Tyr Val Arg Tyr Arg Glu Leu Leu Ser Tyr Leu Thr Gln
145                 150                 155                 160

Asn Ser Gly Arg Leu Val Lys Ser Phe Ile Asp Ala Gln Tyr Leu Asn
                165                 170                 175

Asn Thr Leu Phe Ile Glu Lys Leu Tyr Asn Met Thr Leu Pro Val Trp
                180                 185                 190

Ala Glu Lys Val Tyr Gly Lys Glu Leu Thr Tyr Val Ser Asn Phe
                195                 200                 205

Ala Phe Ser Ile Ala Thr Phe Thr Arg Ser Met Ala Arg Leu Lys Thr
210                 215                 220

Gly Pro Leu Leu Lys Asp Ile Phe Glu Arg Phe Asp Lys Lys Leu Asn
225                 230                 235                 240

Asn Gln Leu Lys Pro Asp Arg Ser Leu Trp Ile Tyr Ser Ala His Asp
                245                 250                 255

Thr Thr Ile Ala Asn Val Leu Asn Ser Leu Lys Leu Phe Glu Leu His
                260                 265                 270

Ser Pro Pro Tyr Ala Ala Cys Ile Met Leu Glu Met Arg Val Asp Asp
                275                 280                 285

Ser Asn Thr Pro Leu Val Ser Val Phe Tyr Lys Asn Thr Thr Ala Glu
                290                 295                 300

Pro Leu Pro Leu Asp Ile Pro Gly Cys Gly Leu Ser Cys Pro Leu Lys
305                 310                 315                 320

Thr Leu Val Lys Leu Tyr Gln Asp Val Leu Pro Gly Asn Trp Glu Arg
                325                 330                 335

Glu Cys Lys Arg Ser Thr Met Met Met Thr Tyr Glu Ala Asn Leu
                340                 345                 350

Gly Ala Ala Thr Gly Ile Leu Ile Phe Ile Thr Val Leu Leu Cys
                355                 360                 365

Ala Ser Tyr Gly Leu Met Val Tyr Tyr Arg Arg Arg His Tyr Asn Leu
370                 375                 380

Tyr Thr Ser Tyr Ser Gln Met Ala
385                 390

<210> SEQ ID NO 28
<211> LENGTH: 356
<212> TYPE: PRT
<213> ORGANISM: Drosophila melanogaster

<400> SEQUENCE: 28

Thr Leu Lys Leu Val His Val Leu Phe Arg His Gly Pro Arg Thr Pro
1               5                   10                  15

Val Ser Thr Tyr Pro Asn Asp Pro Tyr Ile Asn Glu Thr Tyr Glu Pro
                20                  25                  30

Phe Gly Trp Gly Ala Leu Thr Asn Gly Ala Lys Val Glu Leu Tyr Lys
                35                  40                  45
```

```
Ile Gly Lys Gln Leu Arg Gln Arg Tyr Lys Asp Phe Leu Pro Ala Tyr
 50                  55                  60

Tyr Gln Pro Asp Ala Ile Arg Ala Gln Ser Ser Glu Ser Pro Arg Thr
 65                  70                  75                  80

Leu Met Ser Met Gln Met Val Leu Ala Gly Leu Phe Pro Pro Glu Asn
                 85                  90                  95

Thr Pro Met Glu Trp Asn Gln Leu Leu Asn Trp Gln Pro Ile Pro Ile
            100                 105                 110

Val Met Glu Pro Glu Thr Asp Val His Ile Arg Met Lys Ala Pro
        115                 120                 125

Cys Pro Arg Tyr Asp Gly Ser Val Leu Glu Val Ile Glu Leu Pro Glu
130                 135                 140

Val Lys Lys Leu His Ala Glu Ser Ser Asp Leu Leu Arg Glu Leu Thr
145                 150                 155                 160

Thr His Thr Gly Leu Asn Ile Thr His Ala His Asp Val Thr Asn Val
                165                 170                 175

Phe Ile Thr Leu Leu Cys Glu Gln Thr Phe Gly Leu Gln Leu Pro Ser
                180                 185                 190

Trp Thr Asn Asp Tyr Phe Pro Glu Lys Met Leu Pro Leu Ala Glu Lys
                195                 200                 205

Ser Tyr Val Tyr Asp Ala Tyr Thr Thr Glu Gln Arg Lys Met Lys Gly
    210                 215                 220

Gly Phe Phe Val Glu Leu Leu Lys Gln Met Gln Asp Arg Ile Ser
225                 230                 235                 240

Gly Ala Leu Lys Pro Ala Asn Arg Lys Met Phe Leu Ser Cys Gly His
                245                 250                 255

Asp Trp Thr Ile Thr Asn Val Leu Ser Ala Leu Asn Val Trp Glu Ala
            260                 265                 270

Gln Met Pro Arg Phe Ser Ser Leu Ile Ala Phe Glu Leu His Gln Asn
        275                 280                 285

Pro Gln Thr Gly Glu Tyr Phe Leu Glu Ile Tyr Phe Gln Asn Asp Pro
    290                 295                 300

His Lys Glu Pro Gln Gln Leu Gln Ile Pro Gly Cys Glu Lys Gln Cys
305                 310                 315                 320

Pro Ile Gly Lys Leu Leu Glu Leu Thr Lys Asp Ile Ile Pro Asp Ala
                325                 330                 335

Pro Tyr Ala Glu Leu Cys Lys Ala Lys Gly Thr Gln Gly Gly Ala Lys
                340                 345                 350

Ile Ser Tyr His
        355

<210> SEQ ID NO 29
<211> LENGTH: 7
<212> TYPE: PRT
<213> ORGANISM: Apis mellifera

<400> SEQUENCE: 29

Gln Ile Asn Val Ile Phe Arg
1               5

<210> SEQ ID NO 30
<211> LENGTH: 13
<212> TYPE: PRT
<213> ORGANISM: Apis mellifera

<400> SEQUENCE: 30
```

```
Asp Pro Tyr Leu Tyr Tyr Asp Phe Tyr Pro Leu Glu Arg
1               5                   10

<210> SEQ ID NO 31
<211> LENGTH: 9
<212> TYPE: PRT
<213> ORGANISM: Apis mellifera

<400> SEQUENCE: 31

Glu Tyr Gln Leu Gly Gln Phe Leu Arg
1               5

<210> SEQ ID NO 32
<211> LENGTH: 8
<212> TYPE: PRT
<213> ORGANISM: Apis mellifera

<400> SEQUENCE: 32

Leu Tyr Gly Gly Pro Leu Leu Arg
1               5

<210> SEQ ID NO 33
<211> LENGTH: 11
<212> TYPE: PRT
<213> ORGANISM: Apis mellifera

<400> SEQUENCE: 33

His Met Leu Asp Val Val Ser Gly Thr Gln Lys
1               5                   10

<210> SEQ ID NO 34
<211> LENGTH: 12
<212> TYPE: PRT
<213> ORGANISM: Apis mellifera

<400> SEQUENCE: 34

Ile Val Tyr Tyr Leu Gly Ile Pro Ser Glu Ala Arg
1               5                   10

<210> SEQ ID NO 35
<211> LENGTH: 25
<212> TYPE: PRT
<213> ORGANISM: Apis mellifera

<400> SEQUENCE: 35

Glu Leu Lys Gln Ile Asn Val Ile Phe Arg His Gly Asp Arg Ile Pro
1               5                   10                  15
Asp Glu Lys Asn Glu Met Tyr Pro Lys
            20                  25

<210> SEQ ID NO 36
<211> LENGTH: 15
<212> TYPE: PRT
<213> ORGANISM: Apis mellifera

<400> SEQUENCE: 36

Gln Gln Trp Asn Glu Asp Leu Asn Trp Gln Pro Ile Ala Thr Lys
1               5                   10                  15

<210> SEQ ID NO 37
<211> LENGTH: 7
<212> TYPE: PRT
<213> ORGANISM: Apis mellifera
```

```
<400> SEQUENCE: 37

Gly Lys Tyr Glu Phe Ser Lys
1               5

<210> SEQ ID NO 38
<211> LENGTH: 23
<212> TYPE: PRT
<213> ORGANISM: Apis mellifera

<400> SEQUENCE: 38

Lys Leu Glu Glu Trp Thr Ile Thr Thr Pro Lys Asp Tyr Tyr Tyr Ile
1               5                   10                  15

Tyr His Thr Leu Val Ala Glu
            20

<210> SEQ ID NO 39
<211> LENGTH: 8
<212> TYPE: PRT
<213> ORGANISM: Apis mellifera

<400> SEQUENCE: 39

Leu Tyr Gly Gly Pro Leu Leu Arg
1               5

<210> SEQ ID NO 40
<211> LENGTH: 67
<212> TYPE: PRT
<213> ORGANISM: Apis mellifera

<400> SEQUENCE: 40

Glu Tyr Ser Ser Cys Ile Ile Met Glu Tyr His Asn Ile Gly Thr
1               5                   10                  15

His Tyr Val Lys Ile Val Tyr Tyr Leu Gly Ile Pro Ser Glu Ala Arg
            20                  25                  30

Glu Leu Gln Leu Pro Gly Cys Glu Val Leu Cys Pro Leu Glu Lys Tyr
        35                  40                  45

Leu Gln Leu Ile Glu Asn Val Ile Pro Ser Asn Glu Glu Leu Ile Cys
    50                  55                  60

Asp Lys Phe
65

<210> SEQ ID NO 41
<211> LENGTH: 7
<212> TYPE: PRT
<213> ORGANISM: Artificial Sequence
<220> FEATURE:
<223> OTHER INFORMATION: RHGXRXP motif
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 41

Arg His Gly Xaa Arg Xaa Pro
1               5
```